(12) United States Patent
Bae et al.

(10) Patent No.: US 10,228,337 B2
(45) Date of Patent: Mar. 12, 2019

(54) DEVICE AND METHODS FOR ANALYSIS OF BIOMOLECULE STRUCTURE, DYNAMICS AND ACTIVITY

(71) Applicant: NYMIRUM, INC., Ann Arbor, MI (US)

(72) Inventors: Sung-Hun Bae, Gyeonggi-do (SK); Aaron Terrence Frank, Ann Arbor, MI (US); Andrew Corbet Stelzer, San Diego, CA (US); Hashim M. Al-Hashimi, Chapel Hill, NC (US); Joshua Paul Fairbank, Chicago, IL (US); Michael Edward Pape, Ann Arbor, MI (US)

(73) Assignee: Nymirum, Inc., Ann Arbor, MI (US)

( * ) Notice: Subject to any disclaimer, the term of this patent is extended or adjusted under 35 U.S.C. 154(b) by 553 days.

(21) Appl. No.: 14/650,087

(22) PCT Filed: Dec. 5, 2013

(86) PCT No.: PCT/US2013/073330
§ 371 (c)(1),
(2) Date: Jun. 5, 2015

(87) PCT Pub. No.: WO2014/089301
PCT Pub. Date: Jun. 12, 2014

(65) Prior Publication Data
US 2015/0300968 A1    Oct. 22, 2015

Related U.S. Application Data

(60) Provisional application No. 61/733,784, filed on Dec. 5, 2012.

(51) Int. Cl.
*G01N 24/08* (2006.01)
*G01R 33/30* (2006.01)
(Continued)

(52) U.S. Cl.
CPC ......... *G01N 24/087* (2013.01); *G01N 24/088* (2013.01); *G01R 33/465* (2013.01); *G01R 33/302* (2013.01); *G06F 19/16* (2013.01)

(58) Field of Classification Search
CPC ............... G01N 24/088; G01N 24/087; C01H 21/00–21/04; G01R 33/465
See application file for complete search history.

(56) References Cited

U.S. PATENT DOCUMENTS 7,704,923 B2   4/2010   Xiang et al.
8,498,823 B2   7/2013   Al-Hashimi et al.
(Continued)

OTHER PUBLICATIONS

Bodenhausen et al. (Chem. Phy. Let., 1980, 69:185-189) (Year: 1980).*

(Continued)

*Primary Examiner* — Jeremy C Flinders
(74) *Attorney, Agent, or Firm* — Wagenknecht IP Law Group PC

(57) ABSTRACT

The present invention provides a method for determining the 3-dimensional or 3-D atomic resolution structure of a biomolecule using chemical shift data obtained from the biomolecule having one or more selectively isotopically labeled biomolecule monomers and interrogation of same using an NMR device. Methods also comprise use of a low-field NMR device and structure determination method to determine the 2-D and 3-D structure of the biomolecule, for example, a polynucleotide.

16 Claims, 10 Drawing Sheets

(51) Int. Cl.
*G01R 33/465* (2006.01)
*G06F 19/16* (2011.01)

(56) References Cited

U.S. PATENT DOCUMENTS

| | | |
|---|---|---|
| 2004/0038216 A1 | 2/2004 | Hajduk et al. |
| 2005/0234652 A1 | 10/2005 | Sem et al. |
| 2007/0166730 A1 | 7/2007 | Menon et al. |
| 2012/0212224 A1 | 8/2012 | Burns et al. |
| 2017/0032078 A1 | 2/2017 | Stelzer et al. |

OTHER PUBLICATIONS

Tian et al. (J. Biomol. NMR, 2012, 54:237-243) (Year: 2012).*
EP13860225.5 European Search Report dated Oct. 21, 2016.
Gray et al. "Easy, Robust and Accurate NMR Analysis of Biomolecules using Biopack—Technical Overview." Agilent Technologies Inc., 2011, Retrieved from internet http://www.agilent.com/cs/library/technicaloverviews/public/5990-9067en_lo.pdf [retrieved on Nov. 11, 2016].
Kalbitzer et al. "Structure Determination of Polypeptides and Proteins by Two-Dimensional Nuclear Magnetic Resonance Spectroscopy." Physica B Condensed Matter, Jun. 1990, 164(1-2)180-192, Amsterdam, NL.
Oholenschlaeger et al. "Nuclear Magnetic Resonance Studies of Ribonucleic Acids." Spectroscopy, Jan. 2003, 17(2-3)537-547.
International Search Report of PCT/US2013/073330, dated May 13, 2014.
Bryce, David L., et al., Am. Chem. Soc., "Measurement of Ribose Carbon Chemical Shift Tensors for A-form RNA by Liquid Crystal NMR Spectroscopy," 2005, vol. 127, pp. 7387-7396.
Arun, K., et al., Carnegie Mellon University, Computer Science Department "Structure Based Chemical Shift Prediction Using Random Forests Non-Linear Regression," 2005, Paper 1071.

* cited by examiner 0.84 & 0.20   0.88 & 0.21   0.97 & 0.22   0.98 & 0.21   1.00 & 0.23

DEVICE AND METHODS FOR ANALYSIS OF BIOMOLECULE STRUCTURE, DYNAMICS AND ACTIVITY

CROSS REFERENCE TO RELATED APPLICATIONS

This application is a 35 U.S.C. § 371(c) U.S. National Phase filing of International Patent Application Serial No. PCT/US2013/073330, filed Dec. 5, 2013, which claims the benefit of priority to U.S. Provisional Application Ser. No. 61/733,784, filed Dec. 5, 2012. The entire contents of the aforementioned disclosures are incorporated herein by reference in their entirety.

FIELD

The present invention is directed to methods, devices and systems for characterizing and analyzing biomolecule structure with high sensitivity and high fidelity.

BACKGROUND

Ribonucleic acid or RNA is a complex biomolecule made from ribonucleotide building blocks. A ribonucleotide comprises a nucleobase, a 5 carbon ribose sugar and one phosphate group. RNA contains four building blocks, these include: adenylate, guanylate, cytidylate and uridylate. These four RNA nucleotides contain the four RNA nucleosides adenosine, guanosine, cytidine and uridine respectively. RNA transcripts can be found in many cellular forms, including: messenger RNA (mRNA), transfer RNA (tRNA), ribosomal RNA (rRNA), micro RNAs (miRNAs), small interfering RNAs (siRNAs), and mitochondrial RNA. In cells, various RNA molecules play critical roles, for example, they control gene expression, sense and communicate responses to cellular signals, catalyze biological reactions, among many others.

There has been an intense effort to decipher the structure, function, and regulatory networks of the human genome. After sequencing the human genome, scientists have undertaken an immense task of identifying the information present in the genome and in particular, to identify and characterize the functional DNA sequences that are implicated in disease and genetic diversity. The project termed Encyclopedia of DNA Elements (ENCODE) has enlisted 32 groups around the world to identify regions of the human genome that are responsible for gene regulation. One of the valuable contributions of the ENCODE project will be to help make sense of Genome Wide Association Studies (GWAS). Several well documented GWAS studies have shown that specific genetic mutations are linked with disease risk. However, until the ENCODE project, many of these mutations were found in non-protein coding DNA regions (90%) leaving the researchers guessing as to how the mutations can be counteracted or what might cause the disease. The ENCODE project has revealed that many of the disease-linked regions of the genome include enhancers and other functional sequences and scientists are now beginning to understand the role of these enhancers and functional sequences in disease. Some of these important "non-coding" regions are ultimately transcribed into RNA, some of which are now known to be important regulators of gene expression. This regulation often occurs through structural elements that affect recognition by specific RNA binding proteins.

However, the predominant source of cells used to gather results in the ENCODE project have come from a very few select number of cell lines. There are literally thousands of additional cell types that will need to be interrogated and orders of magnitude higher genetic sequences, particularly RNA that will need to be examined once their significance in gene expression regulation has been determined. As yet, there are very few techniques to rapidly and sensitively map the topography of RNA structures for determination of function in gene regulation. The lag in RNA structure characterization techniques will further retard the discovery process that will lead to the understanding of RNA function and its regulatory elements impacting gene expression across the entire genome.

Protein-nucleic acid interactions are involved in many cellular functions, including transcription, RNA splicing, mRNA decay, and mRNA translation. Readily accessible synthetic molecules that can bind with high affinity to specific sequences of single- or double-stranded nucleic acids have the potential to interfere with these interactions in a controllable way, making them attractive tools for molecular biology and medicine. Successful approaches for blocking function of target nucleic acids include the use of duplex-forming antisense oligonucleotides or chemically modified oligonucleotide-like derivatives. In addition to specific RNA structures, the accessibility of different regions of the RNA was recently shown to be important in several processes such as the ability of microRNAs to bind their targets, control of translation speed and control of translation initiation. Gaining knowledge and an appreciation of the RNA structure in three dimensions may also be critical for the development and understanding of RNA-based molecules which may find great utility in a wide range of biotechnological applications, including rational design of biological and molecular sensors that may be useful in the treatment and monitoring of disease. Some of these applications may also provide a greater understanding of the interrelationship between nucleic acid structure and the effects of pH, analytes and proteins.

Nuclear Magnetic Resonance (NMR) spectroscopy is a powerful analytical technique used to determine qualitative and quantitative information about organic molecules. NMR has been used to solve and provide valuable information about the structure of a variety of chemical and biological molecules, ranging from small organic compounds to complex polymers such as proteins and nucleic acids. In NMR, a sample is placed in a magnetic field and is subjected to radiofrequency (RF) excitation at a characteristic frequency called Larmor frequency (f):

$$f = \frac{\gamma}{2\pi} B_0$$

where $\gamma$ is the gyromagnetic ratio of nuclei and $B_0$ is the magnetic field strength. The nuclei in the magnetic field absorb the energy provided and become energized. The frequency of the radiation necessary for absorption depends on the type of nuclei to be excited, (e.g. $^1H$ or $^{13}C$, or $^{15}N$), the frequency will typically also depend on the chemical environment of the nucleus (e.g., the presence of various chemical electronegative groups, salts, pH of solution, and the presence of binding agents), and lastly, the frequency may also depend on the spatial location in the magnetic field if the magnetic field is not uniform, i.e. the field is not homogeneous.

The use of chemical shifts as a new abundant source of structure and dynamics information is arguably more important for nucleic acid structure determination as compared to proteins. NMR structure determination of nucleic acids traditionally suffers from a shortage of accessible interproton NOE-derived distance constraints that can be applied towards structure characterization. This problem is compounded by a high degree of flexibility, particularly in RNA, which can complicate the interpretation of NOE-derived distance constraints.

An inherent obstacle in NMR structure characterization of biomolecules is the relatively poor sensitivity of the NMR procedure. The NMR signal-to-noise (S/N) ratio of biomolecules is impacted by the relatively low abundance of $^{15}N$ (0.365%) and $^{13}C$ (1.108%) and their gyromagnetic ratios (6.73 and −2.71 ($10^7$rad $s^{-1}$ $T^{-1}$) for $^{13}C$ and $^{15}N$, respectively) being markedly lower than that of protons (26.75 ($10^7$ rad $s^{-1}$ $T^{-1}$)). The S/N can be approximated by the equation:

$$S/N \propto n\gamma_e \sqrt{\gamma_d^3 B_0^3 t}$$

where n is the number of nuclear spins being observed, $\gamma_e$ is the gyromagnetic ratio of the spin being excited, $\gamma_d$ is the gyromagnetic ratio of the spin being detected, B0 is the magnetic field strength, and t is the experiment acquisition time. Other factors that are involved in S/N are the probe filling factor (e.g., the fraction of the coil detection volume filled with sample), and various other probe and receiver factors that are typically approximately equivalent for equipment built in the same period of time. It is obvious to users that the highest field instrument available provides the best sensitivity. For fixed t, 20.5 times as much material with a 100 MHz NMR spectrometer than compared to a 750 MHz spectrometer would be needed to obtain an NMR spectra with identical S/N: N300/N750=[750/100]3/2=20.5. In high resolution (i.e. atomic resolution of approximately 1-5 Å) NMR mapping and structure characterization of biological molecules, such as RNA and DNA, the only feasible way to obtain a sufficiently resolved spectrum using chemical shift data is to increase the applied field (i.e. magnetic field strength and radiofrequency excitation). The NMR experiment consists of multiple cycles of pulsing, detection, and repetition delay. At high magnetic fields (600 MHz and higher), the repetition delay of a few seconds is necessary for typical biomolecules of interest to restore perturbed nuclei magnetization back to initial state for the next cycle. Since pulsing and detection combined is normally 80-150 milli-seconds, most of NMR time is spent on repetition delay.

The ENCODE project data to date indicates that a simple, high-throughput nucleic acid structure analysis method and device may help to alleviate the pressing need to link RNA structure to cellular function within the plethora of identified and as yet unidentified RNA molecules that may hold the key to resolving the pathogenesis of many important diseases. There remains a long-felt and unmet need to resolve these nucleic acid dynamic conformations as a means to yield structural information which may lead to the rational design of targeted, biologically-active compounds. One of the barriers to rapid dissemination of RNA structure resides in the lack of customizable, relatively inexpensive and high-throughput processes and devices for NMR analysis of RNA molecules. The understanding of three-dimensional structure of RNA and DNA will certainly apply to drug discovery, but still perhaps more significant applications such as identifying effects of nucleic acid mutations on structure and function and downstream gene regulation tantalizingly await.

The statements in this section merely provide background information related to the present disclosure and may not constitute prior art.

SUMMARY

The present invention provides methods for determining the secondary and 3-D atomic resolution structure of biomolecules using a nuclear magnetic resonance (NMR) based approach, wherein the NMR experiment(s) are conducted at low resonance frequencies, i.e. 300 MHz or less. Devices employing an NMR based structure characterization approach using automated and high-throughput liquid handling components are also provided. The present NMR device also known as a structural genomics imager, employs a unique combination of sample preparation and a bench-top low-field NMR device linked to a database of chemical shifts measured from structurally diverse nucleic acids permitting rapid and cost effective analysis of nucleic acids for structure determination, target drug-ability, toxicology, sequencing, drug discovery and determination of atomic force fields.

In a first aspect, the present invention provides a method for determining the 2-D or 3-D atomic resolution structure of a polynucleotide, the method comprising:
(a) providing a polynucleotide sample comprising a polynucleotide, the polynucleotide comprising at least one nucleotide isotopically labeled with one or more atomic labels selected from the group consisting of $^2H$, $^{13}C$, $^{15}N$, $^{19}F$ and $^{31}P$;
(b) obtaining a NMR spectrum of the polynucleotide sample using a NMR device;
(c) determining a chemical shift of the one or more atomic labels; and
(d) determining a 2-D or a 3-D atomic resolution structure of the polynucleotide from the chemical shifts determined in step (c).

In some embodiments, the method to determine the 2-D or 3-D structure of a polynucleotide requires interrogation of multiple polynucleotides having the same nucleotide sequence, but differing from each other in that each polynucleotide is isotopically labeled on a different nucleotide. In other words, the method determines the chemical shifts of multiple polynucleotides, each polynucleotide having the identical nucleotide sequence as the first polynucleotide analyzed, and each polynucleotide is synthesized with a different nucleotide labeled with the one or more atomic labels. For example, if the polynucleotide has 5 nucleotides, the method would require 5 polynucleotide samples, each polynucleotide labeled with the one or more atomic labels on a different nucleotide. In this same 5 mer polynucleotide example, the method may utilize a smaller number of distinct polynucleotides that the number of nucleotides present in the nucleotide sequence, by strategically labeling one or more nucleotides in the polynucleotide with one or more atomic labels as described herein. In some embodiments, the polynucleotide sample has only one polynucleotide with one nucleotide labeling pattern. In other embodiments, the polynucleotide sample may contain two or more polynucleotides, each having a different nucleotide labeled with one or more atomic labels.

In some of these aspects, the method proceeds to obtain a NMR spectrum of the polynucleotide sample by interrogating the polynucleotide sample with a NMR spectrometer frequency ranging from about 900 MHz to about 20 MHz.

In one of these aspects, the NMR spectrometer frequency is 300 MHz or less, for example, from about 20 MHz to about 100 MHz.

In a second aspect, the present invention provides methods for determining the structure of a target biomolecule when mixed with a small molecule, biomolecule, ligand or other chemical entity (collectively referred to as a ligand) that could interact with the biomolecule of interest. Chemical shift changes on the addition of the ligand indicates that the biomolecule may be interacting with the ligand. The chemical shifts in the presence of the ligand can be collected and used to determine the bimolecular structure of the biomolecule and the bound ligand. In one embodiment of this aspect, the method includes the steps: (a). providing a polynucleotide sample comprising a plurality of polynucleotides, the plurality of polynucleotides having an identical nucleotide sequence, wherein each polynucleotide comprises at least one nucleotide isotopically labeled with one or more atomic labels selected from the group consisting of $^2$H, $^{13}$C, $^{15}$N, $^{19}$F and $^{31}$P; (b). admixing the polynucleotide sample with the ligand forming a plurality of bound complexes; (c). obtaining a NMR spectrum of the bound complexes using a NMR device; (d). determining a chemical shift of the one or more atomic labels; and (e). determining the 3-D atomic resolution structure of the polynucleotides from the chemical shifts determined in step (d).

In some embodiments of the present methods, the target polynucleotide is analyzed by creating a plurality of polynucleotides all having the same nucleotide sequence but differing in the location(s) of isotopically labeled nucleotide(s). In one embodiment, the secondary structure of the polynucleotide is used to determine the placement of the labeled nucleotide or nucleotides to reduce the number of polynucleotide samples. Taking the primary sequence of the polynucleotide, the secondary structure is predicted. Then a plurality of secondary structure predictions can be computed using a secondary structure prediction algorithm (e.g. nearest neighbor algorithm) or computer program. The method then uses an alignment step with the top 10 or so secondary structure predictions and then determines the sites that exhibit the greatest variance in secondary structure. Then the site or sites in the polynucleotide sequence that exhibit largest variance are labeled isotopically for NMR detection or a derivative, wherein one or more nucleotides are labeled per polynucleotide. The labeling scheme can be informed from the chemical shift database whereby multiple isotopic labels can be incorporated into a polynucleotide while maximizing chemical shift dispersion.

In one embodiment, the present invention provides a method for determining one or more specific isotopic labeling positions of one or more nucleotides within a polynucleotide sequence for the determination of 3-D atomic resolution structure or collecting other NMR interaction data of a polynucleotide, the method comprising: (a) providing one or more polynucleotides each of the one or more polynucleotides having an identical polynucleotide sequence, wherein each of the one or more polynucleotides comprises one or more nucleotides labeled with an isotopic label comprising, $^2$H, $^{13}$C, $^{15}$N, $^{19}$F or $^{31}$P; (b) predicting a plurality of structures of the polynucleotide sequence using a computational algorithm (e.g. MC-Sym); (c) identifying one or more region(s) on each of the plurality of polynucleotide structures that exhibit a large structural variation using metrics comprising an S2<0.8 and/or RMSF>0.5 Å; (d) calculating a plurality of chemical shifts from regions of the predicted structures having a large structural variation using a chemical shift predictor; such as Nymirum's RANDOM FOREST™ Predictors (RAMSEY), SHIFTS, NUCHEMICS, and QM methods from the predicted structures and (e) determining one or more specific isotopic labeling positions on each of the polynucleotide sample(s) such that the chemical shift dispersion is maximized and the number of samples is minimized. The MC-Fold|MC-Sym pipeline is a web-hosted service for RNA secondary and tertiary structure prediction. The pipeline means that the input sequence to MC-Fold outputs secondary structures that are directly inputted to MC-Sym, which outputs tertiary structures See generally, Parisien, M. and Major, F. *Nature* 2008, 452 (7183):51-55, which is incorporated herein by reference in its entirety.

In a third aspect, the present invention provides a NMR device that is small enough to sit on top of a standard laboratory bench. In one embodiment of the second aspect, the NMR device comprises (a) a housing; (b) a sample handling device operable to receive a sample comprising a polynucleotide; and (c) an NMR module comprising: (i) a sample conduit comprising an analysis volume operable to receive at least a portion of the sample from the sample handling device; (ii) a plurality of radiofrequency coils disposed proximately to the analysis volume, each coil operable to generate a distinct excitation frequency pulse across the analysis volume to generate nuclear magnetic resonance of the nuclei of the polynucleotide in the analysis volume; (iii) at least one magnet operable to provide a static magnetic field across the analysis volume and the radiofrequency coils; wherein the NMR module has a $^1$H Larmor frequency of 300 MHz or less and the RF coils are operable to transmit the excitation frequency pulse to the analysis volume and detect signals from NMR produced by the nuclei of the polynucleotide contained in the analysis volume. Optionally, the device further comprises a heating and cooling device in thermal coupling with the analysis volume. In this regard, the NMR device can employ the use of a sample conduit or analysis volume heating and cooling device for heating the sample containing the biomolecule, for example a protein or a nucleic acid, for example, an RNA polynucleotide to anneal the polynucleotide and bring the polynucleotide into a relaxed or stable conformation prior to acquisition of NMR spectra.

In one embodiment of the NMR device, the NMR module, further includes a spectrometer heating or cooling device which maintains the analysis volume at a predetermined temperature during acquisition of NMR spectra. In still a further embodiment, the NMR device also employs a signal processing device, which may include one or more of an analog to digital converter, a signal amplifier, a signal conditioner and combinations thereof.

In another aspect, the present invention provides a method for determining the specific isotopic labeling positions of nucleotides within a polynucleotide sequence for the determination of 3-D atomic resolution structure of a polynucleotide, the method comprising:

(a) providing one or more polynucleotides each polynucleotide having an identical polynucleotide sequence, wherein each of the one or more polynucleotides comprises one or more nucleotides labeled with an isotopic label comprising, $^2$H, $^{13}$C, $^{15}$N, $^{19}$F or $^{31}$P;

(b) predicting a plurality of putative structures of the polynucleotide sequence using a computational algorithm;

(c) computing one or more predicted NMR chemical shifts for each putative structure;

(d) determining a predicted chemical shift overlap for all of the plurality of putative structures; and identifying one or more structural regions of the plurality of putative structures that give rise to a large variation of predicted chemical shifts;

(f) determining one or more specific isotopic labeling positions that minimize chemical shift overlap while focusing on the positions with large variation in predicted chemical shifts and maximizing the number of labelings per sample at these positions;

(g) determining a plurality of predicted 2-D structures to identify regions of the polynucleotide structure with large variations and designing an optimum labeling scheme that minimizes spectral overlap wherein more than one nucleotide within the polynucleotide sequence is labeled; and (h) using the predicted chemical shift dispersion profiles to provide an optimum labeling scheme that minimizes spectral overlap wherein more than one nucleotide within the polynucleotide sequence is labeled.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

Figure 7:
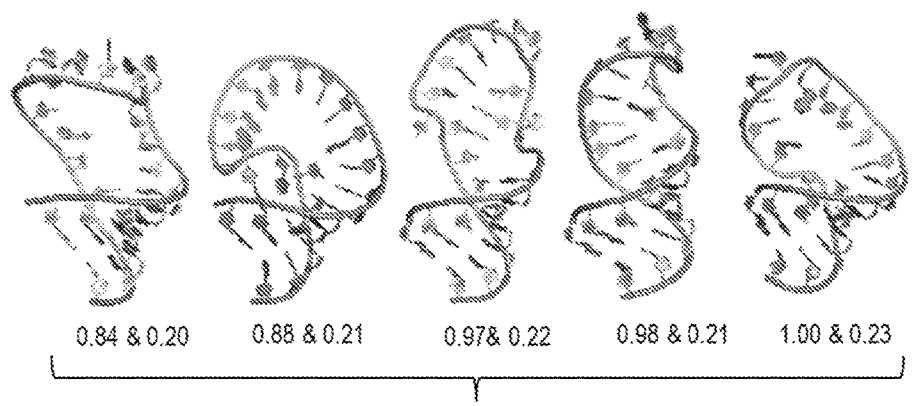

FIG. 7 depicts schematic representations of the output of structural models of human pre-miR 122 apical loop RNA that were obtained by modeling the structures against experimental chemical shift data. The numbers below each model indicate the $^{13}C$ and $^{1}H$ chemical shift RMSD between measured chemical shift versus predicted chemical shift using the methods in accordance with the teachings of the present disclosure.

Figure 8:
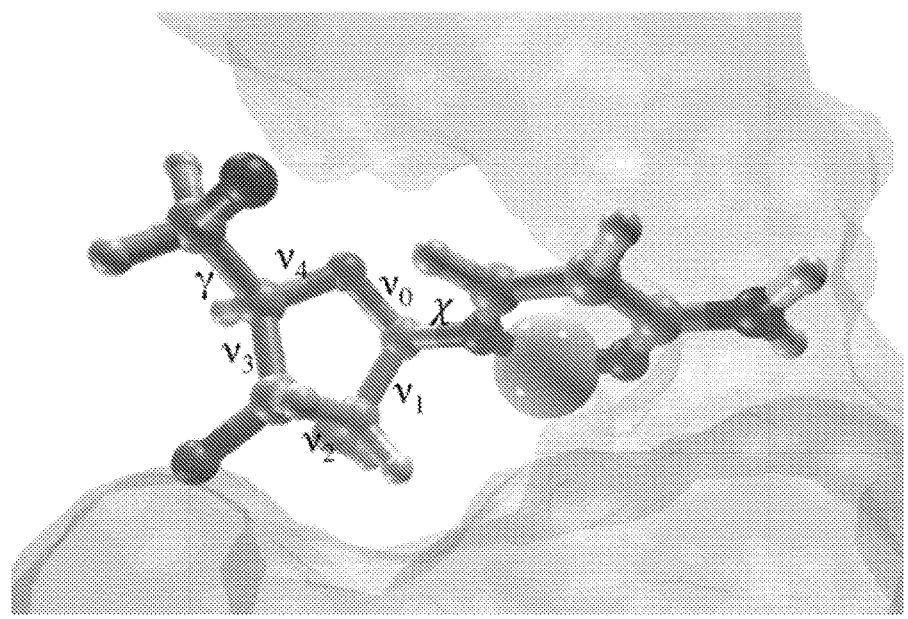

FIG. 8 depicts the structural features used in one example of RNA to describe the local structure surrounding carbon nuclei. Shown are the torsion angles $\chi$, $\gamma$, $\nu_0$, $\nu_1$, $\nu_2$, $\nu_3$, and $\nu_4$ associate with a given carbon nucleus (yellow). Also shown is the representative surface of neighboring atoms would contribute to contact strength (Eq. 1) and local electrostatic potential (Eq. 2).

Figure 9A:
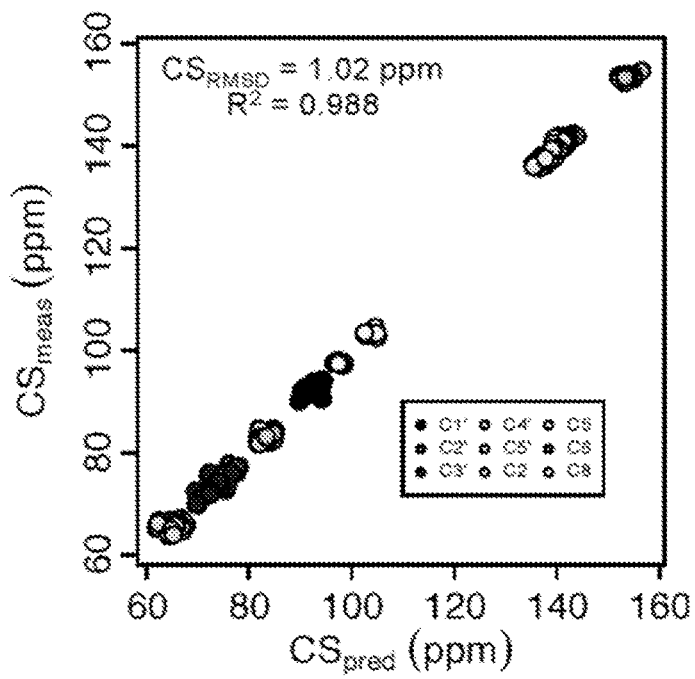

FIG. 9A depicts Measured vs. RAMSEY predicted $^{13}C$ chemical shifts. (a) Correlations plots comparing measured and predicted $C_1'$, $C_2'$, $C_3'$, $C_4'$, $C_5'$, $C_2$, $C_5$, $C_6$ and $C_8$ chemical shifts in the validation set. The $CS_{RMSD}$ and $R^2$ are 1.02 ppm and 0.988, respectively.

Figure 9B:
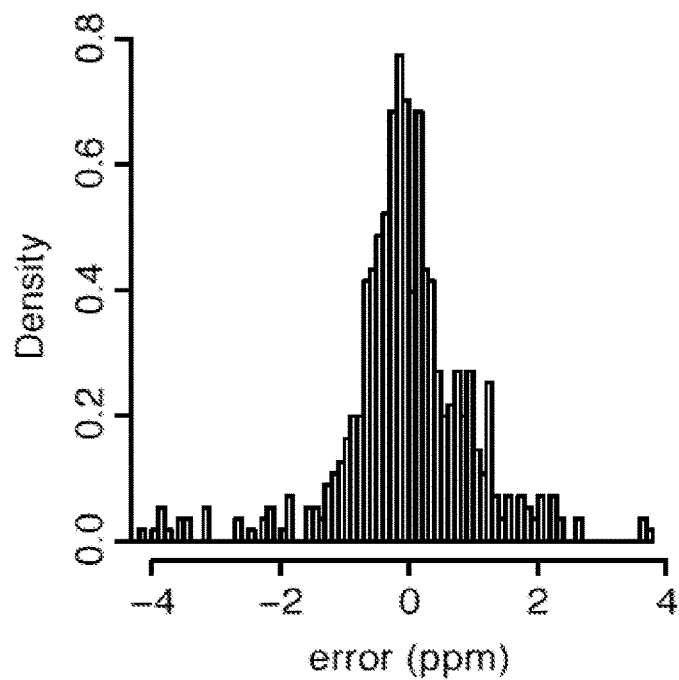

FIG. 9B depicts a histogram of prediction errors.

Figure 10A:
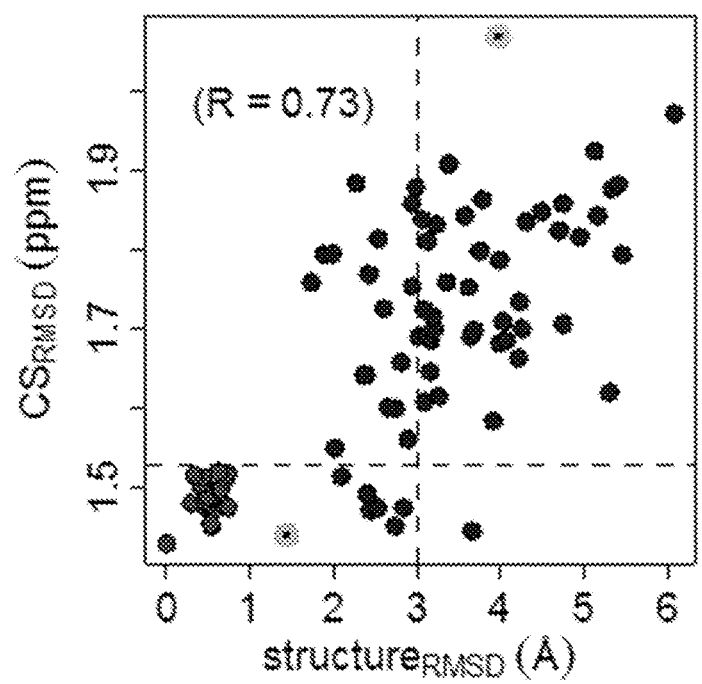

FIG. 10A depicts a correlation plot between $CS_{RMSD}$ and structure$_{RMSD}$. Data from the native NMR ensemble and MC-Sym models are shown in red and blue, respectively. Data points corresponding to MC-Sym models with the lowest and highest $CS_{RMSD}$ are highlighted in orange and green, respectively.

Figure 10B:
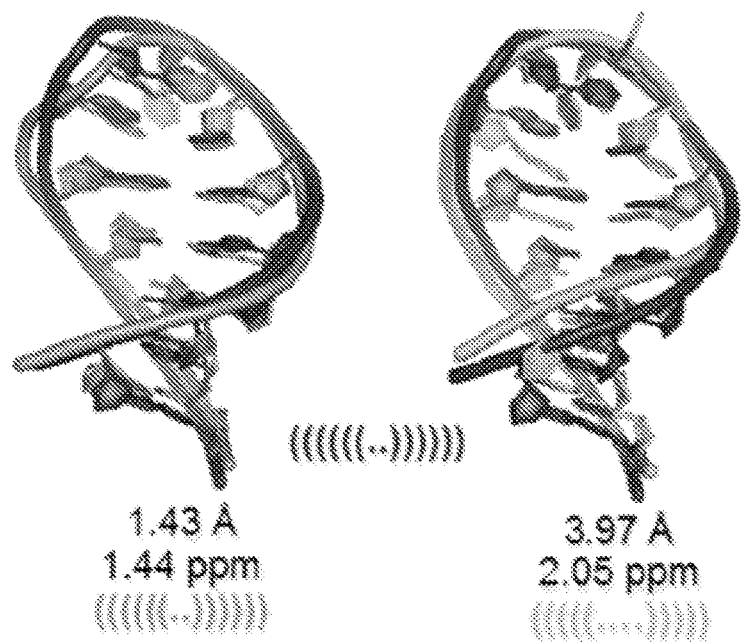

FIG. 10B depicts a schematic diagram overlay of the NMR model 1 (red) with MC-Sym models that exhibited the lowest (orange) and the highest (green) $CS_{RMSD}$. Included below each figure are the structure$_{RMSD}$, $CS_{RMSD}$ and the corresponding 2-D structure of the MC-Sym models.

Figure 11:
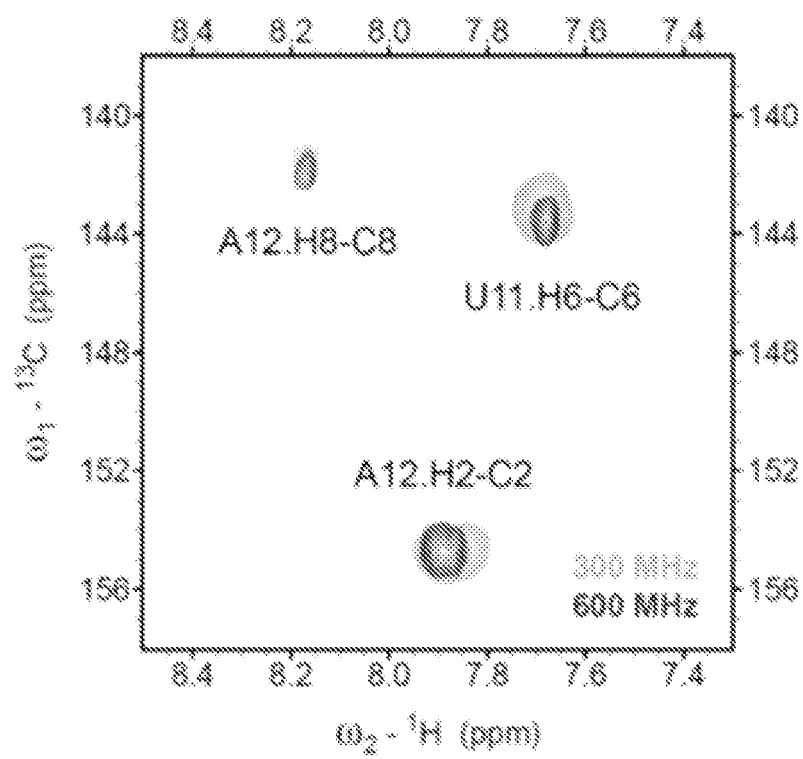

FIG. 11 depicts a comparison of 2-D $^{13}C$—$^{1}H$ HMQC (heteronuclear multiple quantum correlation) NMR spectra acquired at 300 (green) and 600 (red) MHz.

DETAILED DESCRIPTION

The following description is merely exemplary in nature and is not intended to limit the present disclosure, application, or uses.

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. The following definitions and non-limiting guidelines must be considered in reviewing the description of the technology set forth herein.

The headings (such as "Introduction" and "Summary") and sub-headings used herein are intended only for general organization of topics within the present technology, and are not intended to limit the disclosure of the present technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The citation of references herein does not constitute an admission that those references are prior art or have any relevance to the patentability of the technology disclosed herein. Any discussion of the content of references cited in the Introduction is intended merely to provide a general summary of assertions made by the authors of the references, and does not constitute an admission as to the accuracy of the content of such references. All references cited in the "Description" section of this specification are hereby incorporated by reference in their entirety.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it is also envisioned that Parameter X may have other ranges of values including 1-9, 2-9, 3-8, 1-8, 1-3, 1-2, 2-10, 2.5-7.8, 2-8, 2-3, 3-10, and 3-9.

Although the open-ended term "comprising," as a synonym of terms such as including, containing, or having, is use herein to describe and claim the present invention, the invention, or embodiments thereof, may alternatively be described using more limiting terms such as "consisting of" or "consisting essentially of" the recited ingredients.

The terminology used herein is for the purpose of describing particular example embodiments only and is not intended to be limiting. As used herein, the singular forms "a", "an" and "the" may be intended to include the plural forms as well, unless the context clearly indicates otherwise. Thus, for example, reference to "a ligand" includes mixtures of ligands; reference to "an NMR resonance" includes more than one resonance, and the like. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

As used herein, the term "biomolecule" refers to any organic molecule that is part of or from a living organism. Biomolecules can include nucleic acids, a nucleotide, a polynucleotide, an oligonucleotide, a peptide, a protein, a ligand, a receptor, among others.

As used herein, the term "peptide" is a polymer in which the monomers are amino acids and which are joined together through amide bonds and alternatively referred to as a polypeptide. In the context of this specification it should be appreciated that the amino acids may be the L-optical isomer or the D-optical isomer. Peptides are two or more amino acid monomers long, and often more than 20 amino acid monomers long.

As used herein, the term "protein" as used herein, refers to a long polymer of amino acids linked via peptide bonds and which may be composed of two or more polypeptide chains. More specifically, the term "protein" refers to a molecule composed of one or more chains of amino acids in a specific order; for example, the order as determined by the base sequence of nucleotides in the gene coding for the protein. Proteins are essential for the structure, function, and regulation of the body's cells, tissues, and organs, and each protein has unique functions. Examples are hormones, enzymes, and antibodies.

As used herein, the term "sequence" refers to the particular ordering of monomers within a biomolecule and it may be referred to herein as the sequence of the biomolecule.

As used herein, the term "polynucleotide" or "nucleic acid" as used herein refer to any polyribonucleotide or polydeoxribonucleotide polymer comprising nucleotides of any length, and are made up of ribonucleotides or deoxyribonucleotides, that comprise purine or pyrimidine nucleobases, sugars and covalent internucleoside (backbone) linkages or other natural, chemically, or biochemically modified, or non-naturally or derivatized nucleotide bases. Thus, the term "polynucleotide" as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions and may include modified nucleotides. The terms "nucleic acid," "nucleic acid sequence," or "oligonucleotide" also encompass a polynucleotide as defined above. In some embodiments, a polynucleotide is a short interfering RNA (siRNA), a microRNA (miRNA), a plasmid DNA (pDNA), a short hairpin RNA (shRNA), messenger RNA (mRNA), antisense RNA (asRNA), to name a few, and encompasses both the nucleotide sequence and any structural embodiments thereof, such as single stranded, double stranded, triple stranded, helical, hairpin, etc.

A "modified polynucleotide" in one embodiment, can include a polynucleotide containing one or more modified nucleotides. A modified nucleotide can include a nucleotide which comprises an altered base and/or altered sugar and/or altered internucleotide linkage but which can still incorporate into a nucleic acid molecule via an internucleotide linkage and form Watson Crick bonds with another nucleotide. In some illustrative examples, modified nucleotides can include, methylated cytosine (5-methylcytosine), adenine methylation, 5-hydroxymethylcytosine, glycosylation of uracil, 5-position pyrimidine modifications, 8-position purine modifications, modifications at cytosine exocyclic amines, and substitution of 5-bromo-uracil; and 2'-position sugar modifications, including but not limited to, sugar-modified ribonucleotides in which the 2'-OH is replaced by a group such as an H, OR, R, halo, SH, SR, $NH_2$, NHR, $NR_2$, or CN, wherein R is an alkyl moiety. Modified nucleotides can also include nucleotides with bases such as inosine, queuosine, xanthine, sugars such as 2'-methyl ribose, non-natural phosphodiester internucleotide linkages such as methylphosphonates, phosphorothioates and peptides. In some embodiments, the pentafuronosyl ring may be replaced with acyclic derivatives lacking the C2'-C3'-bond of the pentafuronosyl ring. For example, acyclonucleotides may substitute a 2-hydroxyethoxymethyl group for-the 2'-deoxyribofuranosyl sugar normally present in dNMPs The nucleoside subunits of the nucleic acid disclosed herein may be linked to each other by phosphodiester bond. The phosphodiester bond may be optionally substituted with other linkages. For example, phosphorothioate, thiophosphate-D-ribose entities, triester, thioate, 2'-5' bridged backbone (may also be referred to as 5'-2'), PACE, 3'- (or -5')deoxy-3'- (or -5')thio-phosphorothioate, phosphorodithioate, phosphoroselenates, 3'- (or -5')deoxy phosphinates, borano phosphates, 3'- (or -5')deoxy-3'- (or 5'-)amino phosphoramidates, hydrogen phosphonates, phosphonates, borano phosphate esters, phosphoramidates, alkyl or aryl phosphonates and phosphotriester modifications such as alkylphosphotriesters, phosphotriester phosphorus linkages, 5'-ethoxyphosphodiester, P-alkyloxyphosphotriester, methylphosphonate, and nonphosphorus containing linkages for example, carbonate, carbamate, silyl, sulfur, sulfonate, sulfonamide, formacetal, thioformacetyl, oxime, methyleneimino, methylenemethylimino, methylenehydrazo, methylenedimethylhydrazo and methyleneoxymethylimino linkages. In some embodiments, modified polynucleotides can include polynucleotides having a peptide nucleic acid (PNA) backbone. The PNA backbone can include repeating N-(2-aminoethyl)-glycine units linked by peptide bonds. The various bases such as purine, pyrimidine, natural and synthetic bases are linked to the backbone by methylene carbonyl bonds.

In some embodiments, altered inter nucleotide linkages can include modifications made at terminal phosphate groups. Non-limiting examples of different stabilization chemistries can be used, e.g., to stabilize the 3'-end of nucleic acid sequences, including (1) [3-3']-inverted deoxyribose; (2) deoxyribonucleotide; (3) [5'-3']-3'-deoxyribonucleotide; (4) [5'-3']-ribonucleotide; (5) [5'-3']-3'-O-methyl ribonucleotide; (6) 3'-glyceryl; (7) [3'-5']-3'-deoxyribonucleotide; (8) [3'-3']-deoxyribonucleotide; (9) [5'-2']-deoxyribonucleotide; and (10) [5-3']-dideoxyribonucleotide. In addition to unmodified backbone chemistries, polynucleotides of the present invention can include conventional backbone chemistries combined with one or more different backbone modifications described herein. The nucleoside subunits of the nucleic acid disclosed herein may be linked to each other by phosphodiester bond. The phosphodiester bond may be optionally substituted with other linkages. For example, phosphorothioate, thiophosphate-D-ribose entities, triester, thioate, 2'-5' bridged backbone (may also be referred to as 5'-2'), PACE, 3'- (or -5')deoxy-3'- (or -5')thio-phosphorothioate, phosphorodithioate, phosphoroselenates, 3'- (or -5')deoxy phosphinates, borano phosphates, 3'- (or -5')deoxy-3'- (or 5'-)amino phosphoramidates, hydrogen phosphonates, phosphonates, borano phosphate esters, phosphoramidates, alkyl or aryl phosphonates and phosphotriester modifications such as alkylphosphotriesters, phosphotriester phosphorus linkages, 5'-ethoxyphosphodiester, P-alkyloxyphosphotriester, methylphosphonate, and nonphosphorus containing linkages for example, carbonate, carbamate, silyl, sulfur, sulfonate, sulfonamide, formacetal, thioformacetyl, oxime, methyleneimino, methylenemethylimino, methylenehydrazo, methylenedimethylhydrazo and methyleneoxymethylimino linkages. Other examples of modified nucleotides, for example, modified ribonucleotides are described in http://rna-mdb.cas.albany.edu/RNAmods/cgi-bin/rnafind.cgi, the disclosure of which is incorporated herein by reference in its entirety.

Modified bases refer to nucleotide bases such as, for example, adenine, guanine, cytosine, thymine, and uracil, xanthine, inosine, and queuosine that have been modified by the replacement or addition of one or more atoms or groups. Some examples of types of modifications that can comprise nucleotides that are modified with respect to the base moieties, include but are not limited to, alkylated, halogenated, thiolated, aminated, amidated, or acetylated bases, in various combinations. More specific modified bases include, for example, 5-propynyluridine, 5-propynylcytidine, 6-methyladenine, 6-methylguanine, N,N,-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino)propyluridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides.

Modified nucleotides also include those nucleotides that are modified with respect to the sugar moiety, as well as nucleotides having sugars or analogs thereof that are not ribosyl. For example, the sugar moieties may be, or be based on, mannoses, arabinoses, glucopyranoses, galactopyranoses, 4-thioribose, and other sugars, heterocycles, or carbocycles. Sugar moieties can be modified such as, 2'-deoxypentofuranosyl sugar moiety, D-ribose, hexose, modification at the 2' position of the pentofuranosyl sugar moiety such as 2'-O-alkyl (including 2'-O-methyl and 2'-O-ethyl), i.e., 2'-alkoxy, 2'-amino, 2'-O-allyl, 2'-S-alkyl, 2'-halogen (including 2'-fluoro, chloro, and bromo), 2'-methoxyethoxy, 2'-O-methoxyethyl, 2'-O-2-methoxyethyl, 2'-allyloxy ($—OCH_2CH=CH_2$), 2'-propargyl, 2'-propyl, ethynyl, propenyl, CF, cyano, imidazole, carboxylate, thioate, $C_1$ to $C_{10}$ lower alkyl, substituted lower alkyl, alkaryl or aralkyl, $OCF_3$, OCN, O-, S-, or N-alkyl; O-, S, or N-alkenyl; $SOCH_3$; $SO_2CH_3$; $ONO_2$; $NO_2$, $N_3$; heterozycloalkyl; heterozycloalkaryl; aminoalkylamino; polyalkylamino or substituted silyl, as, among others.

As used herein, the term "target effector molecule" describes a molecule that can be selected from any biological molecule which is activated or inhibited by ligand binding to a recognition domain on the molecule. Target effector molecules encompassed by the present technology can include a diverse array of compounds including proteins, polypeptides, oligopeptides, polysaccharides and nucleic acids, including RNA and DNA. Exemplary proteins can include enzymes, transmembrane transporters, signal receptors and mediators, primary and secondary messengers, transcription and translation factors, and others. In a preferred method for practicing the technology isotopically labeled molecules are used for the target effector molecule, and substitute for the naturally occurring target effector molecule.

As used herein, the term "ligand" describes any naturally occurring or synthetic compound, or fragment thereof, that binds to the recognition domain of a target effector molecule. In some embodiments, the ligand can be a small organic molecule. Some of these small molecules are part of a larger collection of molecules found in combinatorial libraries. Ligands of the present technology also include members of combinatorial libraries of natural or synthetic small molecules, wherein the libraries contain tens, hundreds, thousands, hundreds of thousands, and millions of variant species. Recognition domains include both primary binding domains and regulatory domains. Ligands can thus be analogs of known substrates or inhibitors or regulators of biological activity. They can also be compounds with no previously identified biological effect. Inhibitor analogs, substrate analogs and regulator analogs can be covalently linked to one another or to any class of ligand to enhance activity by the process of this invention. Binding between ligand and target effector molecule can be any form that causes the desired activation or inhibition, and includes ionic bonding, hydrogen bonding, and Van der Waals association.

As used herein, the "recognition domain" of a target effector molecule describes the local site of the target effector molecule to which a ligand binds and promotes modification of the target effector molecule's biological activity. This modification can be described as agonist activity or antagonist activity, depending on the circumstances of a particular ligand binding event.

As used herein, "magnetic," "magnetic effect," and "magnetism" refer to the phenomena by which one material exert an attractive or repulsive force on another material. Although theoretically all materials are influenced to one degree or another by magnetic effect, those skilled in the art understand that magnetic effect or magnetism is only recognized for its detectability under the specific circumstance.

As used herein, a "permanent magnet" is a material that has a magnetic field without relying upon outside influences. Due to their unpaired electron spins, some metals are magnetic when found in their natural states, as ores. These include iron ore (magnetite or lodestone), cobalt, and nickel. A "paramagnetic material" refers to a material that attracts and repels like normal magnets when subject to a magnetic field. Paramagnetic materials include aluminum, barium, platinum, and magnesium. A "ferromagnetic material" is a material that can exhibit a spontaneous magnetization. Ferromagnetism is one of the strongest forms of magnetism and is the basis for all permanent magnets. Ferromagnetic materials include iron, nickel, and cobalt. A "superparamagnetic material" is a magnetic material that exhibits a behavior similar to that of a paramagnetic material at temperatures below the Curie or the Neel temperature.

An "electromagnet" is a type of magnet in which the magnetic field is produced by a flow of electric current. The magnetic field disappears when the current ceases. A simple type of electromagnet is a coiled piece of wire that is electrically connected. An advantage of an electromagnet is that the magnetic field can be rapidly manipulated over a wide range by controlling the electric current. In the embodiments of the invention, ferromagnetic or non-magnetic materials are used to form the electromagnets.

The term "microprocessor" generally relates to a processor on an integrated circuit (IC) chip. The processor may be one or more processor on one or more IC chip. The chip is typically a silicon chip with thousands of electronic components that serves as a central processing unit (CPU) of a computer or a computing device. A computer of the present invention may contain one or more microprocessors useful in the calculation of Fast Fourier Transforms, chemical shifts, various constraints using chemical shift data and other NMR data, for example, NOE, RDC, J-couplings, and residual chemical shift anisotropy RCSA's and their use in the determination of calculated structures of various biomolecules.

The term "analysis volume" refers to the internal volume space within a sample conduit that is actively interrogated in the NMR device, and more specifically, is the volume space that typically will hold the sample between the magnet and various RF coils which is used during the NMR interrogation to produce NMR of a selected biomolecule that is delivered to the analysis volume.

The term "polynucleotide sample" includes a polynucleotide or a certain quantity (e.g. a number of moles or a concentration of polynucleotide) of the polynucleotide, optionally dissolved in a solvent, wherein the polynucleotides in the polynucleotide sample has one singular nucleotide sequence. In some examples, the polynucleotides in the polynucleotide sample may only have the same nucleotide labeled with the one or more atomic labels, or the polynucleotide sample can consist of polynucleotides synthesized with different nucleotides labeled with one or more atomic labels.

As used herein, the term "NMR interaction(s)" refer to all isotropic and anisotropic NMR measurements including but not limited to chemical shifts. J couplings, dipolar couplings, and paramagnetic interactions.

I. Device and System for Determining Structural Information of a Biomolecule

In various embodiments, the present invention provides a NMR device or apparatus, operable to determine the 3-D atomic resolution structure of a biomolecule, for example, a polynucleotide, for example an RNA polynucleotide using low field NMR. In some embodiments, the NMR device comprises: (a) a housing; (b) a sample handling device operable to receive a sample comprising a biomolecule, for example, a protein, a polypeptide, a nucleic acid, or combinations thereof. In one embodiment, the biomolecule can include a polynucleotide, for example, an RNA polynucleotide; and (c) an NMR module comprising: (i) a sample conduit comprising an analysis volume operable to receive at least a portion of the sample from the sample handling device; (ii) a plurality of radiofrequency coils disposed proximately to the analysis volume, each coil operable to generate an excitation frequency pulse across the analysis volume to generate nuclear magnetic resonance of the nuclei of the polynucleotide in the analysis volume; (iii) at least one magnet operable to provide a static magnetic field across the analysis volume and the radiofrequency coils; wherein the NMR module has a spectrometer frequency of 300 MHz or less and the RF coils are operable to transmit the excitation frequency pulse to the analysis volume and detect signals from NMR produced by the nuclei of the polynucleotide contained in the analysis volume. Optionally, the NMR device comprises a heating and cooling device in thermal communication with the analysis volume.

In some embodiments, the components of the device can be integral or modular in form. In one embodiment, the device is a unitary design comprising a housing made of metal or a magnetically inert polymer material, such as a durable plastic and the like. The housing contains a sufficient dimension to accommodate the various components of the NMR device. In some embodiments, the housing can measure less than a meter wide by less than a meter long and less than a meter tall, which may conveniently sit on common laboratory benches.

In one embodiment, the device comprises a device, a NMR module, a sample heating and cooling unit, an analysis module and a user interface.

a. Sample and Liquid Handling

In some embodiments, the NMR device or apparatus used for biomolecule structure characterization can comprise a manual or automated, e.g. robotic, liquid dispensing device that is operable to transfer one or more samples containing the biomolecule to be interrogated using NMR from a sample storage device e.g. a cartridge based system, to the NMR module. In operation, the sample handling device transfers the biomolecule, e.g. a polynucleotide in the sample storage device to the sample conduit in the NMR module. In one embodiment, the sample handling device mechanically couples with the sample storage device. Then the sample handling device transfers a predetermined volume of reagent from one or more auxiliary agent containers to the sample storage device and transfers the sample containing the resuspended biomolecule, e.g. a polynucleotide directly to the sample conduit for NMR spectroscopy, or it may be transferred to a mixing chamber or other vessel for either heating such as in the process of annealing, or in the mixing chamber to be added to an auxiliary agent, for example a deuterated solvent, a standard for NMR recording, a perturbation agent, or a candidate/screening compound for binding studies. In some embodiments, when characterization of the target biomolecule involves perturbation assays with different pH solutions, different salt solutions or the target biomolecule is screened for binding to a candidate/screening compound e.g. against a library of combinatorial compounds, the sample handling device can also facilitate mixing and handling of auxiliary reagents. In an illustrative embodiment, the sample handling device can include one or more of fluidic systems from Protasis (MA, USA) Protasis Discovery Tower, optionally coupled with automation control software from Protasis (MA, USA) commercially available as OneMinute-NMR ("OM-NMR") web-based software.

In another example, the sample handling device can include a liquid handling robot from CTC (Swiss) marketed in the US by Leap Technologies, www.leaptec.com for the handling of microliter-volume samples. Optionally, the sample handling device can further include a mixing apparatus comprising a mixing chamber, and a liquid collection device, (e.g. a pipette, syringe or other liquid acquisition device). In one embodiment, the sample handling device can also include a heating or cooling device, for example a heat transfer device, a heating element, a thermoelectric device, for example a Peltier element and the like. In operation, the heating and cooling device can heat the sample containing the biomolecule of interest to a predetermined temperature prior to transferring the sample to a sample conduit, for example a NMR tube, a Shigemi NMR tube, or a capillary tube (for example a glass capillary tube measuring 2-15 cm in length and having an internal bore diameter of 0.001 mm to about 1 mm in diameter). In one such embodiment, a polynucleotide which may be single stranded or double stranded may be heated to a temperature of about 95° C. for 5 minutes, and then gradually reduce the heat until the polynucleotide has reached room temperature. The sample handling device can then transfer the annealed polynucleotide to the sample conduit of the NMR module using micro or macro fluidics, or other liquid delivery methods. In various embodiments, the auxiliary agents can also include buffers, deuterated solvent used for NMR spectroscopy, internal chemical shift reference standards, salts, chaotropic agents and other reagents commonly employed in NMR studies.

For screening purposes, the device may also comprise a mechanical interface to allow manipulation of microplates and microplate well fluid contents so that compound libraries may be easily manipulated and cataloged with the other components of the present device. In some embodiments, the sampling device comprises a means or mechanism that would draw a user-defined volume of solution containing the candidate or screening molecule from a high-throughput receptacle, such as a 96, 128, or 384, or 1536 well microplate, optionally, each microplate bearing a bar code for automated reading and identification. The solution could then be dispensed into a mixing chamber with the biomolecule of interest and then transferred to the sample conduit for NMR spectra recording. This type of interface can be used to screen many types of molecules of interest (small molecules, combinatorial compounds, RNAs, DNAs, analytes, peptides, metabolites etc.) for example, thousands or tens of thousands of screening or candidate compounds in high-throughput fashion. The mechanical interface could be similar to the stacker used in microplate readers and can be controlled through the user interface containing a software component operable to manipulate the device.

b. The NMR Module

The NMR module is a part of the NMR apparatus that focuses on the excitation of the nuclear spins, and detection of the NMR signal. The NMR module goes into the center of the magnetic field provided by one or two magnets, and the sample conduit is inserted into the NMR module to perform the NMR experiment. The NMR module contains the radiofrequency (RF) coils, tuned at specific frequencies, generally less than 300 MHz, for specific nuclei in a given magnetic field, The NMR module also contains the necessary hardware for example a heating and cooling device to control the sample temperature in the analysis volume within the NMR module.

In some embodiments, the NMR module provides at least two RF transmitting/receiving coils, herein called "RF coils". One RF coil can be placed closest to the sample (the inner coil), and another further from the sample (the outer coil). This allows the NMR module to deliver and respond to multiple frequencies, and to allow multi-nuclear NMR experiments. The nuclei that use the inner coil are detected with the highest sensitivity. Therefore, a NMR module can be provided with the inner-coil tuned to a "broadband" nucleus (i.e. $^{13}$C, $^{15}$N or $^{31}$P), for maximum sensitivity for these nuclei when used in a "direct" detection mode. An Inverse or Indirect Detection NMR module, can be provided such that the inner-coil is tuned for $^1$H (or $^1$H & $^{19}$F). These probes give the highest proton ($^1$H) sensitivity, with much lower sensitivity to directly observe lower frequency nuclei (such as $^{13}$C, $^{15}$N or $^{31}$P) and are called herein "indirect" detection mode.

The NMR module may accommodate various sizes of sample conduits. In general, larger volume sample conduits are best in cases where the sample is solubility (or concentration) limited. Larger volumes allow more sample to be contained in the coil. Smaller volume sample conduits allow the concentration of the sample to be increased when solubility is not a limiting factor Small volume probes (i.e. 3 mm, a Shigemi NMR tube, a Nanotube, or a capillary tube or capillary coil, for example a glass capillary tube measuring 2-100 cm in length and having an outer diameter measuring from about 4 mm to about 1.5 mm, and an internal bore diameter of 0.001 mm to about 2.0 mm in diameter) give the highest sensitivity when very small amounts of highly soluble materials are under study.

In some embodiments, the NMR module can comprise: (i) a sample conduit comprising an analysis volume operable to receive at least a portion of the liquid sample from the sample handling device; (ii) two or more radiofrequency coils disposed proximately to the analysis volume, each coil operable to generate a distinct excitation frequency pulse across the analysis volume to generate nuclear magnetic resonance of the nuclei of the polynucleotide in the analysis volume; (iii) one or more magnets operable to provide a static magnetic field across the analysis volume and the radiofrequency coils; and optionally, (iv) a heating and cooling device in thermal communication with the analysis volume.

In operation, the NMR module can provide a $^1$H Larmor frequency of about 300 MHz or less, or about 299 MHz or less, or about 250 MHz or less, or about 225 MHz or less, or about 200 MHz or less, or less than about 175 MHz, or less than about 150 MHz, or less than about 125 MHz, or less than about 100 MHz, preferably, ranging from about 20 MHz to about 300 MHz, or from about 20 MHz to about 299 MHz, or from about 50 MHz to about 275 MHz, or from about 75 MHz to about 250 MHz, or from about 75 MHz to about 225 MHz, or from about 75 MHz to about 200 MHz, or from about 75 MHz to about 175 MHz or from about 100 MHz to about 300 MHz, or from about 125 MHz to about 275 MHz, or from about 20 MHz to about 250 MHz, or from about 20 MHz to about 225 MHz, or from about 20 MHz to about 200 MHz, or from about 20 MHz to about 150 MHz, or from about 20 MHz to about 100 MHz, across the analysis volume. In some embodiments, the static magnetic field is 90° to the RF magnetic field created by the one or more RF coils. In some embodiments, the NMR module can include one or more permanent magnets or one or more electromagnets sufficient to produce magnetic field of $^1$H Larmor frequency of 300 MHz or less, or magnetic field strength of less than 7 Tesla (T), for example, 0.5 T to about 7 T, or from about 0.5 T to about 5 T, or from about 0.5T to about 3T.

In various embodiments, the magnet or two or more magnets provide a static magnetic field ($B_0$) that is perpendicular to the axis of the RF coils ($B_1$). In some embodiments a static magnetic field can be generated by a permanent magnet or the Halbach magnet array that comprises a material that has a magnetic field without relying upon outside influences. In some embodiments, the static magnetic field can be generated by an electromagnet that comprises ferromagnetic or non-magnetic materials. An electromagnet is a type of magnet in which the magnetic field is produced by a flow of electric current. The magnetic field disappears when the current ceases. A simple type of electromagnet is a coiled piece of wire that is electrically connected. An advantage of an electromagnet is that the magnetic field can be rapidly manipulated over a wide range by controlling the electric current. In some embodiments, the one or more permanent magnets or one or more electromagnets can be adjusted to provide a static magnetic field across at least a portion of the analysis volume in the sample conduit. Materials suitable for use as the permanent magnet or electromagnet include permanent magnetic materials, ferromagnetic materials, paramagnetic materials, and non-magnetic metals. When a ferromagnetic material is used for the magnet, an external magnetic field is used to magnetize the material. Further, when either a ferromagnetic or non-magnetic material is used for the magnet, an electrical current is applied to the material to create an electromagnet. In one embodiment of the invention, at least one of the magnets comprises one or more of iron, nickel, cobalt, a rare-earth material such as neodymium, copper, aluminum, and mixtures thereof. In some embodiments, a Neodymium-Iron-Boron type magnet can be used.

The NMR device of the present invention can provide NMR analysis of biomolecules that are selectively labeled with one or more isotopically labeled nuclei in a low static magnetic field. In some embodiments, the sample is excited using one or more resonant frequencies selected for the specifically labeled nuclei in the samples using NMR spectroscopy at $^1$H Larmor frequencies of 300 MHz or less, for example, ranging from about 20 MHz to about 300 MHz, and all frequencies, whether integer or fractional there between. In one embodiment, the static magnetic field, together with the excitation magnetic field generated by the RF coils, (for example a pair of micro-coils described in further detail below) is capable of creating nuclear magnetic resonance within a liquid sample contained in the analysis volume of the sample conduit. In this regard, the magnet is "associated" with the analysis volume for holding a liquid sample, meaning that the magnet is so situated that it will achieve the desired effect on the sample being interrogated and contained within the analysis volume. A number of factors will be considered when associating the magnet with the analysis volume, including whether the magnet is placed perpendicular, or parallel to a longest axis of the analysis volume in the sample conduit, the size of the magnet, the sizes and placement of the RF coils, the space provided by the RF coils, the desired strength of the static magnetic field, and the volume within which the desired NMR that is capable of detecting $^1$H, $^2$H, $^{13}$C, $^{15}$N, $^{19}$F and/or $^{31}$P chemical shifts of biomolecules, for example, polynucleotide samples interrogated, and is optionally compatible with existing automation solutions. In some embodiments, the NMR module can comprise an commercially available microflow NMR probe, wherein the microflow probe comprises a capillary sample conduit, in which sample is passaged through the capillary and through the analysis volume.

In one embodiment, the one or more magnets is/are placed near or adjacent to the analysis volume of the sample conduit for holding a liquid sample. The specific type, size, strength, and location of the one or more magnets in the device may be determined relative to the RF coils positioned around or adjacent to the sample conduit. Specific characteristics of the one or more magnets, including the magnetic field strength can be determined based on the specific analysis desired by a person skilled in the art.

In one embodiment, the one or more magnets is/are capable of generating a static magnetic field strength of from about 0.5 Tesla (T) to about 7 (T), or, $^1$H Larmor frequencies of about 20 MHz to about 300 MHz. As disclosed herein, for NMR, a static magnetic field strength of about 0.5 T-7 T may be required. Thus, in a specific embodiment, the magnet(s) is/are capable of generating a static magnetic field strength of from about 0.5 T to about 7 T. In another specific embodiment, the magnet is capable of generating a static magnetic field strength of from about 0.5 T to about 3.0 T, or from about 0.5 T to about 5T.

Positioned between or adjacent to the one or more magnets are at least two, or three, or four, or five RF coils whose function may include to provide an RF pulse of a specific frequency to cause resonance of various nuclei including $^1$H, $^2$H, $^{13}$C, $^{15}$N, $^{19}$F or $^{31}$P, and to transmit the NMR signal from the sample to a computer for further processing. In some embodiments, there are at least two RF coils placed around, or adjacent to an analysis volume of a sample conduit. In some embodiments, the RF coils can comprise two or more coils, one for high-frequency $^1$H and/or $^{19}$F pulses, and others for lower-frequency pulses sufficient to resonate nuclei having a different Larmor precession frequency (e.g. $^{13}$C, $^{15}$N, $^{31}$P). In some embodiments, a NMR module contains an inverse (i.e. optimized for proton detection) multi-resonance (multiple tuned to $^1$H, $^{13}$C, $^{15}$N, $^{31}$P) RF coil arrangement, for example a plurality of micro-coils. The frequency depends on the magnetic field strength and the gyromagnetic ratio of the nucleus. An indirect-detection or inverse NMR module has the high-frequency RF coil nearer the sample than the lower-frequency coil and as a result the probe provides superior sensitivity to $^1$H 1-D or $^1$H detected multi-dimensional NMR experiments such as a HSQC, whereas a direct-detection probe is reversed, such that the lower-frequency coil is closer to the sample and the probe provides superior sensitivity to nuclei other than $^1$H or $^{19}$F. All other things being equal, an inner coil will yield better sensitivity for observation of a given nucleus because the inner coil is more tightly coupled to the sample. In some embodiments, for the detection of polynucleotides, the RF coils in the NMR module are placed in an indirect-detection mode or inverse-NMR module mode.

In some embodiments, the NMR spectral analysis of the interrogated sample can include the use of RF coils known in the art as micro-coils. A micro-coil containing NMR module can employ better filling factor and mass-sensitivity than standard 5 or 3 mm sample conduits. In one example, sensitivity of micro-coil can extend 5 times more than when compared to standard 5 mm probe using a same amount of sample in different volumes (Extending the scope of NMR spectroscopy with micro-coil probes Schroeder FC, Gronquist M Angew Chem Int Ed Engl. (2006) November; 45:(43) 7122-31). The micro-coil containing NMR module would be ideal for liquid flow based automation and mass-limited and not-concentration-limited samples such as the polynucleotides examined in the present methods and interrogation systems of the present invention. In one embodiment of the invention, the micro-coil is a solenoid type coil. Solenoid type micro-coils are multiple spiral wire loops, which may or may not be wrapped around a metallic core. A solenoid type micro-coil produces a magnetic field when an electrical current is passed through it and can create controlled magnetic fields. In one embodiment of the invention, the solenoid type micro-coil can produce a uniform magnetic field in a predetermined volume of the space.

In some embodiments, the NMR spectral analysis can be performed using multiple magnets and micro-coils to handle multiple NMR samples with reasonable throughput at low magnetic fields. In some embodiments, multiple RF coils can be housed in a single NMR module to share transmitter/receiver channels and to measure multiple samples simultaneously. An eight-coil high-frequency NMR module design for high-throughput nuclear magnetic resonance spectroscopy is known in the art, for example, see Wang H, Ciobanu L., Edison A. S., Webb A. G., Journal of Magnetic Resonance. (2004) October; 170:(2) 206-12, and MacNaughtan M A, Hou T, Xu J, Raftery D., "High-Throughput Nuclear Magnetic Resonance Analysis Using a Multiple Coil Flow Probe" (2003), Analytical Chemistry; 75:5116-5123. (The disclosure of this reference is incorporated by reference herein in its entirety.)

In one embodiment, the NMR module may comprise a separate circuitry capable of detecting, processing, or analyzing the signals from the one or more RF coils positioned around or adjacent the analysis volume during and after the RF pulsing.

In some embodiments, the NMR module also contains an actively shielded PFG (pulsed-field gradient) coil to provide a field gradient pulse to the sample in the analysis volume. By adding another coil of wire in the NMR module, and running a direct current through it, one can create a magnetic field gradient across the sample. A pulsed-field gradient is required in some embodiments to suppress the dominant signal from a solvent, for example water.

In some embodiments, the NMR module can further include multiple heating and cooling devices that can serve to regulate the temperature of the one or more permanent magnets and the sample in the analysis volume, individually. In some embodiments, the heating and cooling devices can include a heat transfer device, a cooling unit, a heating element, a thermoelectric device, for example a Peltier element and the like.

The apparatus can further include a computer to perform mathematical and statistical calculations relevant and necessary for the acquisition of chemical shifts from NMR signals obtained during NMR interrogation. The analysis module can typically comprise of a processor, for example a microprocessor or computer processor or a computer having one or more microprocessors, one or more memory buffers, RAM, or ROM, a data storage device, and a means for inputting signals and/or data obtained from the Signal Processing device, for example, electronic or digital signals and/or data operable to record 1D, 2D, 3-D and 4D spectra, including 1D $^1$H, 1D $^{13}$C, 1D or 2D $^1$H—$^1$H TOCSY (correlation spectroscopy), 1D or 2D $^1$H—$^{13}$C HSQC (heteronuclear single quantum coherence), spin-state-selective HSQC, 1D or 2D $^1$H—$^{13}$C HMQC (heteronuclear multiple quantum coherence), 1D or 2D $^1$H—$^{15}$N HSQC, 1D or 2D $^1$H—$^{15}$N spin-state-selective HSQC, 1D or 2D $^1$H—$^{15}$N HMQC, and 1D NOE (nuclear Overhauser effect spectroscopy) difference, 2D $^1$H-$^1$H NOESY (nuclear Overhauser effect spectroscopy; mixing time=10-1000 msec), 1D, 2D, or 3-D $^{13}$C-editted and/or $^{15}$N-edited NOESY-HSQC or 1D, 2D, or 3-D $^{13}$C-editted and/or $^{15}$N-edited NOESY-HMQC spectra in D$_2$O and/or H$_2$O/D2O mixture to the analysis module.

Such spectra are sufficient to determine various standard structural NMR restraints, for example, chemical shift data, residual dipolar coupling (RDC)s, J coupling, NOE and the like. The computer or microprocessor comprises a central processing unit, a memory, memory bank, or a memory buffer, or program storage device, for example, RAM, ROM, a disc drive, a flash drive, or some other medium operable to store a computer program. In some embodiments, computer programs that can be employed to determine data or portions of data required to acquire a 3-D structure, or data related to the 3-D-structure of a polynucleotide can include: SHIFTS, SHIFTX, NUCHEMICS, RAMSEY, MC-Sym, ROSETTA, Topspin (Bruker), VNMRJ (Agilent), SPARTA, SPARKY. Other common communication input/output devices, such as a keyboard, mouse and the like. In some embodiments, the analysis module comprises one or more software programs operable to automate the liquid sample handling and NMR experimental set-up, regulate sample temperature, execute NMR electronics, acquire NMR FID (free induction decay) data, Fourier transform and processing the FID, pick peaks from a past or to be recorded NMR spectra, determination of internal reference peak, determination of chemical shift, peak intensity or volume, and peak splitting (J couplings and residual dipolar couplings), RNA structure prediction, perform molecular dynamics simulation and software to enable chemical shift directed polynucleotide structure determination, software to calculate binding affinities (or dissociation constant, $K_d$) of one or more compounds operable to bind with a selected polynucleotide.

In some embodiments, the NMR device can optionally also include a user interface having capabilities to interact with the software stored in the analysis module. In some embodiments, the user interface has electronic output signal capability or software instructions operable to interact with the device, including the sample handling device, the NMR module and the analysis module. The user interface can select for one or more samples to be withdrawn from one or more sample storage devices, for example, one or more cartridges, select the chemical environment of the sample, by further electing one or more auxiliary agents from the stored reagents in the NMR device.

In some embodiments, the user interface comprises a graphical user interface (GUI) for example, a touch screen interface that provides a series of options for further instructing the device of the present invention to perform one or more liquid sample manipulations, one or more NMR analyses and return one or more data values, images, computer generated graphics, data representations or compilation of data values, for example, one or more of the 2-D & 3-D structure of a polynucleotide of interest, assess heterogeneity of a polynucleotide sequence and whether it folds into one or multiple structural forms; structurally map out RNA/DNA-protein and RNA/DNA-ligand interactions; measure the binding affinities/specificities between the RNA/DNA and protein, ligand and other molecules; assign NMR resonances; screen a library of small molecules, biological, or other compounds for binding to the RNA/DNA; evaluate the similarities in the 2-D and 3-D structure of different nucleotide sequences; evaluate presence/absence of specific tertiary interactions; evaluate presence/absence of specific elements of secondary and 3-D atomic resolution structure; evaluate how changes in physiological conditions such as temperature and pH affect RNA/DNA structure; evaluate protonation/tautomer state of base-pairs; and evaluate structure of excited states (such as transient Hoogsteen base-pairs).

In various embodiments, the NMR device optionally comprises a sample storage device, for example, a cartridge having a proprietary insertion mechanism so that it is only fits the intended instrument or device. In various embodiments, the cartridge can contain a predefined isotopically labeled biomolecule, for example, a polynucleotide, wherein the selectively labeled biomolecule is then further processed using the NMR device defined herein. In some embodiments, the sample storage device comprises a microfluidics component operable to load a predefined volume of selectively labeled biomolecule into the sample conduit of the NMR device.

The NMR device of the present invention when using the methods described herein, is operable to provide information and or data related to the 2-D & 3-D structure of a polynucleotide of interest, assess heterogeneity of a polynucleotide sequence and whether it folds into one or multiple structural forms; structurally map out RNA/DNA-protein and RNA/DNA-ligand interactions; measure the binding affinities/specificities between the RNA/DNA and protein, ligand and other molecules; assign NMR resonances; screen a library of small molecules, biological, or other compounds for binding to the RNA/DNA; evaluate the similarities in the 2D and 3-D structure of different nucleotide sequences; evaluate presence/absence of specific tertiary interactions; evaluate presence/absence of specific elements of secondary and 3-D atomic resolution structure; evaluate how changes in physiological conditions such as temperature and pH affect RNA/DNA structure; evaluate protonation/tautomer state of base-pairs; evaluate structure of excited states (such as transient Hoogsteen base-pairs); and generate Dynamic Atomic-scale RNA drug targets and measurement of anisotropic properties useful in refining the structure determination using other NMR interactions.

Figure 1:
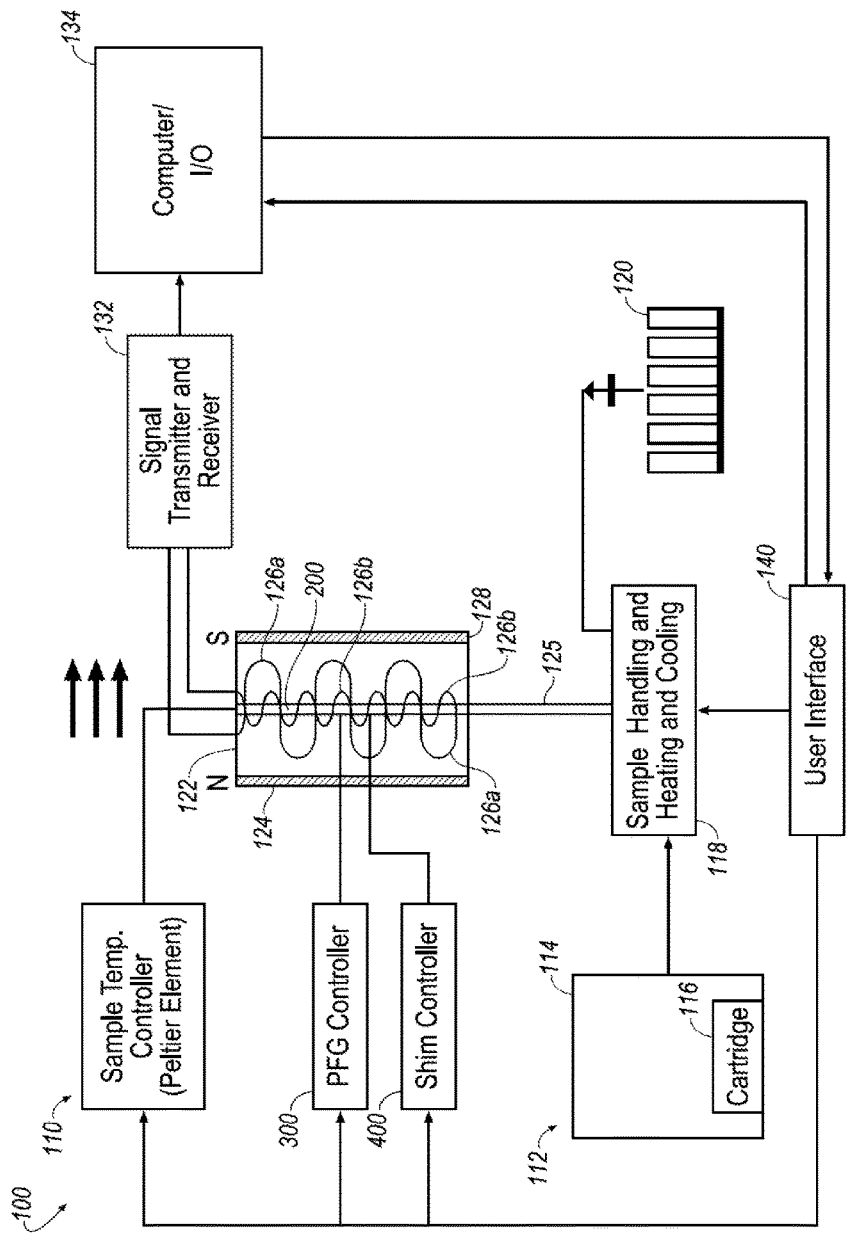
FIG. 1 depicts a schematic representation of the various components of the NMR device in accordance with the several embodiments of the present disclosure.

For the purpose of brevity, the following exemplary embodiments will illustrate the invention using a polynucleotide as a representative biomolecule. Other biomolecules such as proteins and polypeptides could also be used in the present invention as described for polynucleotides. With reference to FIGS. 1-6E, in one embodiment, a NMR device 100 of the present invention is shown in FIG. 1. User interface 140 provides the software and signal processing required to perform a plurality of chemical and biophysical analyses. User interface 140 captures the user selection for the analysis parameters, including the registration of one or more biomolecule samples, including the polynucleotide length, the amino acid or nucleic acid sequence of the biomolecule, the chemical environment of the biomolecule during analysis, the NMR interrogation parameters, the analysis type, and the user's output parameters. In one embodiment, the user interface device 140 sends signals to the computer 134 to perform an analysis of a biomolecule provided in sample storage device 114. In addition, the user interface 140 captures from the user, several analysis parameters such as shim adjustment via shim controller 400 and provide signals to the pulsed-field gradient controller 300 to generate a pulsed-field gradient across the analysis volume 200. In one embodiment, a sample storage device 114 can comprise a cartridge 116 containing one or more selected polynucleotides which may be selectively labeled with one or more isotopically labeled nucleotides. The cartridge 116 or the sample storage device 114 may also comprise a plurality of wells, or a microfluidic device or other mechanical means (not shown herein) to facilitate separation of one or polynucleotides. Typically, the polynucleotides are stored in the cartridge 116 in a lyophilized form. Cartridge 116 can then be inserted into an opening (not shown) of sample handling device 118. Under guidance from instructions provided from user interface 140, sample handling device 118 can add a reagent from auxiliary agents 120 into cartridge 116 to dissolve the polynucleotide. The dissolved polynucleotide can be added to any other reagent that may be deemed appropriate for the particular analysis invoked. Such reagents can be delivered from auxiliary agent 120. Other reagents may include: buffers, deuterated reagents, stabilizing agents, screening candidate compounds, inhibitors or agonists that interact with the polynucleotide during NMR interrogation.

In one embodiment, a device of the present invention can include a heating and cooling apparatus in thermal coupling with the sample to be analyzed in the sample handling device 118. In one embodiment, once the final chemical environment of the polynucleotide has been prepared, the sample can be heated in sample handling device 118 and annealed by heating the sample to a desired heating temperature, for example, 95° C. to facilitate annealing of the polynucleotide followed by a cooling routine, for example, return to room temperature prior to delivery to sample conduit 125. Such heating and cooling conditions can be inputted by the operator using the user interface 140 and can vary according to the biomolecule under analysis or the combination of reagents used to prepare the sample. Sample handling device 118 then transfers the polynucleotide sample to sample conduit 125 for NMR interrogation in the NMR module 122.

NMR module 122 comprises a sample conduit 125 containing the sample to be analyzed. Sample conduit 125 can include any liquid conduit such as a tube or capillary tube that can store the sample during the NMR interrogation. The purpose of this has been to confine most of the material of interest into the analysis volume 200 of the RF coils 126a and 126b, therefore gain highest possible sensitivity given the circumstances. In some embodiments, the sample conduit 125 is made from a material that can be heated and cooled from about −80° C. to about 150° C. In some embodiments, the sample conduit 125 can include commercially available NMR tubes, for example, tubes that are appropriate for use in NMR protocols involving spectrometer frequencies of 300 MHz or below, for example, 5 mm tubes, 3 mm tubes, containing ASTM Type 1 Class A, B Glass, Shigemi NMR tubes matched with an appropriate standard, (for example, $CDCL_3$, CDCL31, $CD_3OD$, DMSO-$d_6$, and $D_2O$) having outer diameters ranging from 5 mm to 2 mm, and capillary tubes for low field NMR (i.e. a $^1H$ Larmor frequency ranging from about 20 MHz to about 300 MHz) measuring 3-1.5 mm outer diameter×100 mm in length made from borosilicate glass or Pyrex®, commercially available from (CapNMR|, Protasis/MRM, Marlboro, Mass.) and Wilmad. In some embodiments, capillary NMR tubes are capable of sample volumes ranging from 1 μL-100 μL.

The NMR module 122 also comprises a pair of permanent magnets 124 and 128 which are disposed in axially (parallel) to the sample conduit 125, and are placed perpendicular to the direction of the magnetic field generated by the RF coils 126a, and 126b.

Figure 3:
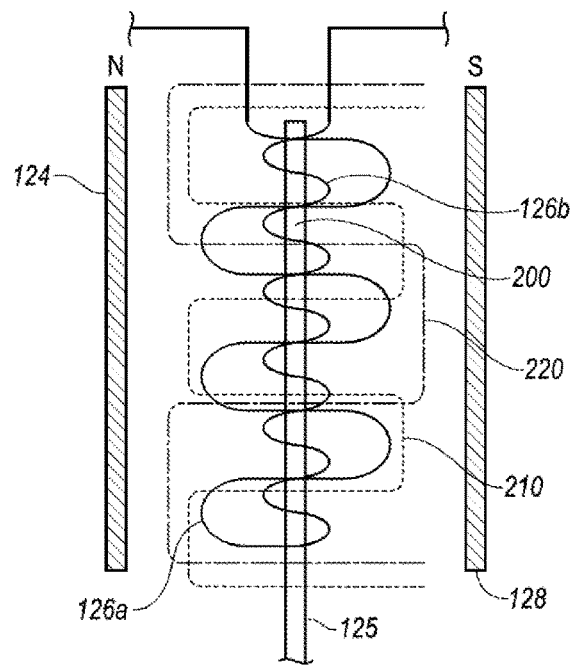
FIG. 3 depicts a side elevational view of an exemplary NMR module in accordance with the teachings of the present disclosure.

In operation, the NMR module 122 comprises one magnet shown illustratively in FIG. 1 as 124 and 128 and contains radiofrequency (RF) coil(s) 126a and 126b surrounding the sample to be interrogated in the analysis volume 200. During an NMR experiment, the RF coil(s) 126a and 126b transmit pulses originated from the signal transmitter and receiver 132 to the sample contained within the analysis volume 200, and receives the NMR signal from the sample and is directed back to the signal transmitter and receiver 132. A NMR module 122 of the present invention may include two or more RF coils, 126a and 126b, one for high-frequency $^1H$ and/or $^{19}F$ pulses shown illustratively in FIGS. 1 and 3 as 126b, and a second RF coil 126a for lower-frequency pulses (e.g. $^{13}C$, $^{15}N$, and $^{31}P$). The spectrometer frequency or $^1H$ Larmor frequency depends on the magnetic field strength and the gyromagnetic ratio of the nucleus, which in the present invention can range from about 20 MHz to 300 MHz. An indirect-detection or inverse configuration comprises an NMR module 122 configuration as shown in FIGS. 1 and 3, wherein the high-frequency coil 126b is placed closer to the sample in the analysis volume 200 of sample conduit 125 than the lower-frequency coil 126b. As a result, the NMR module 122 provides superior sensitivity to $^1H$ 1D or $^1H$ detected multi-dimensional NMR experiments such as a HSQC. In other embodiments, the NMR module 122 may comprise a direct-detection configuration in which the RF coils 126b and 126a are reversed, such that the lower-frequency coil 126a is closer to the analysis volume 200 and the RF coil 126b is placed outside of RF coil 126a. In this configuration, NMR module 122 provides superior sensitivity to nuclei other than $^1H$ or $^{19}F$. In some embodiments, other things being equal, an inner RF coil 126b will yield better sensitivity for observation of a given nucleus because the RF coil 126b is more tightly coupled to the sample.

In various embodiments, the NMR module 122 can be designed for various sample volumes contained within sample conduit 125. For solubility-limited samples, large volume sample conduits 125 allows a larger number of observed nuclei in the analysis volume 200 to be contained inside the RF coils 126b, and 126a, and provides more signal, or a higher signal to noise ratio (S/N) but for very small amount of highly soluble samples. In some embodiments, small volume sample conduits 125 (i.e. 3 mm, 1 mm, or capillary tube/coil) can in certain embodiments, provide the highest sensitivity. As shown in FIG. 1, in some embodiments, the sample contained within the analysis volume 200 can be thermally regulated by thermally interfacing a sample temperature controller 110 to the sample conduit 125 and analysis volume 200. With reference to FIG. 3, in some embodiments, the NMR module 122 can also include a pulse-filed gradient (PFG) coil 210 which surrounds axially, the RF coils 126a, and 126b and the analysis volume 200 containing the sample being interrogated using NMR, which allows coherence selection and filtering out unwanted signals such as water signal in the $H_2O$ samples. In some embodiments, the NMR module 122 may optionally also include one or more shim coils 220 which surrounds the analysis volume 200 of sample conduit 125, the RF coils 126a and 126b and the PFG coil 210 and compensates spatial inhomogeneities in the static magnetic field $B_o$. These inhomogeneities could be caused by the magnet design, materials in the probe, variations in the thickness of the sample tube, sample permeability, and ferromagnetic materials around the magnet. One or more shim coils 220 deployed herein can be designed to create a small magnetic field which will oppose and cancel out an inhomogeneity in the $B_o$ magnetic field. Because these variations may exist in a variety of functional forms (linear, parabolic, etc.), one or more shim coils 220 may be needed to create a variety of opposing fields.

Figure 4:
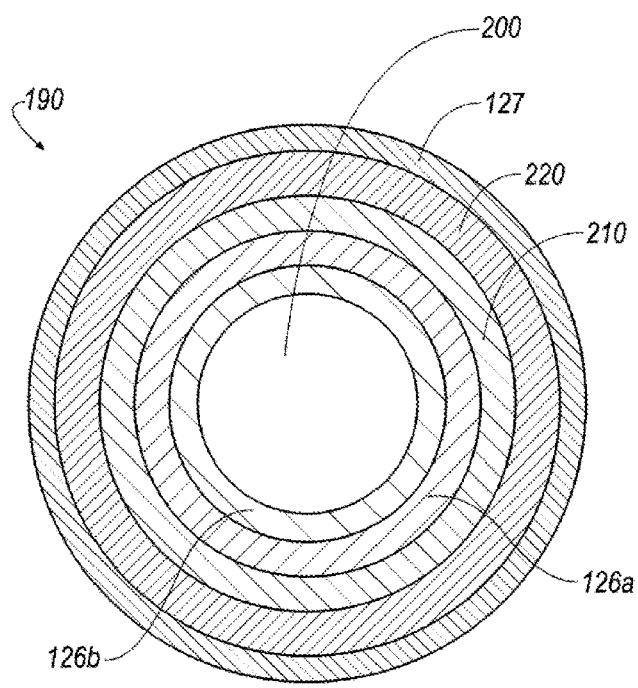
FIG. 4 depicts a cross-sectional view of an exemplary NMR module in accordance with the teachings of the present disclosure.

In some embodiments, NMR signals received from the analysis volume 200 as a result of NMR interrogation can be received by an additional RF coils (not shown) which may be in RF communication with NMR signals emitted from the sample in the analysis volume 200 after pulsing with the appropriate resonance frequency. In some embodiments, as shown in FIGS. 1 and 3-4, RF coils 126a and 126b may also emit pulsed RFs at the appropriate frequencies, and sense and receive NMR signals from the sample in the analysis volume 200. Thus, signals received from the RF coils 126a and 126b may be transmitted to an analog to digital converter (not shown) in signal transmitter and receiver 132. Signals thus obtained may also be amplified and sent to the computer 134 for further analysis and evaluation in accordance with the present methods described herein.

Figure 5:
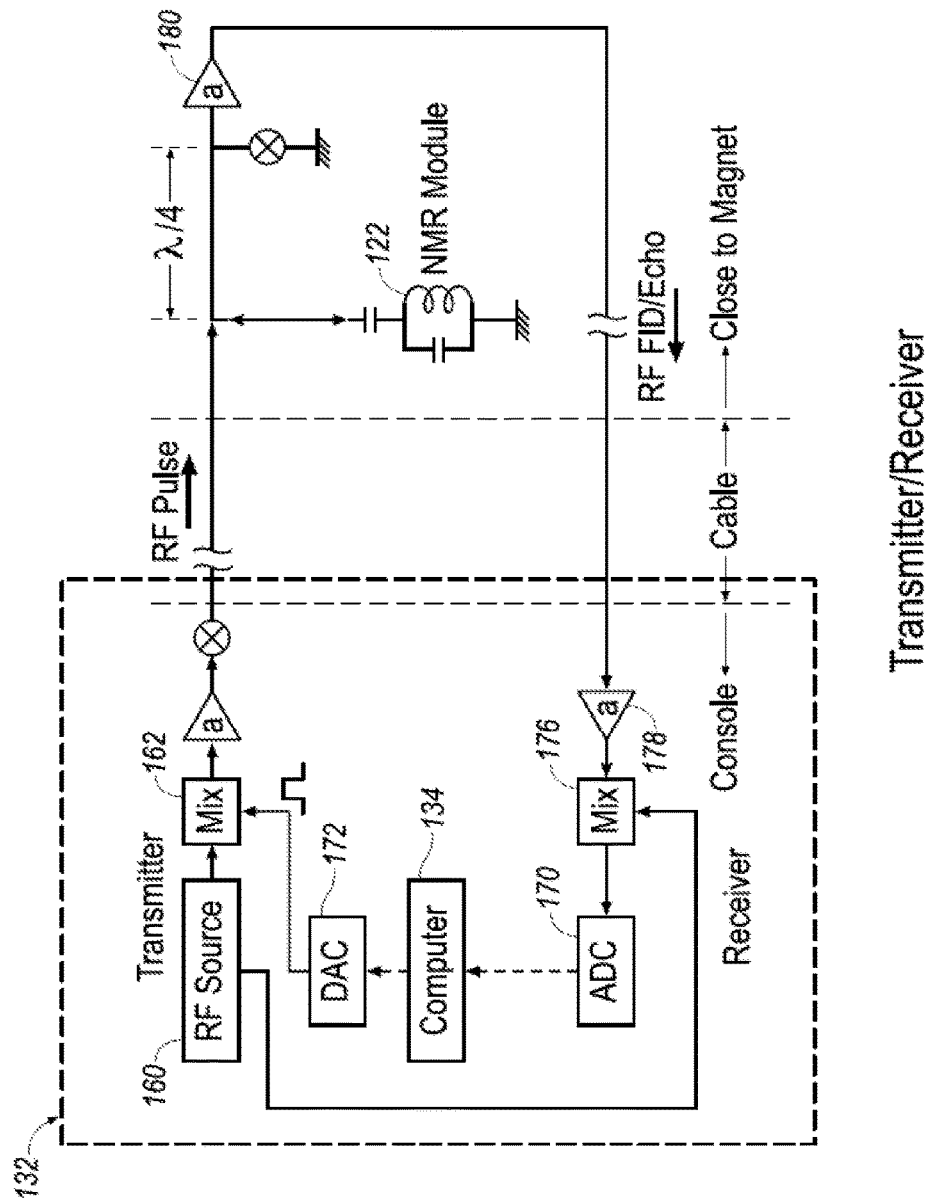
FIG. 5 depicts a schematic representation of the transmitter receiver component of the NMR device in electrical communication with the NMR module in accordance with the teachings of the present disclosure.

In one embodiment, with reference to FIGS. 1 & 5 an exemplary signal transmitter and receiver 132 is provided. The radio frequency source 160 is operatively connected to the computer 134 and may be programmable in accordance with NMR software useful in the NMR spectroscopy of organic molecules. The transmitter portion of signal transmitter and receiver 132 comprises a radio frequency (RF)

source 160 which may be operatively connected to the computer 134. RF source 160 may be programmable in accordance with NMR software useful in the NMR spectroscopy of organic molecules. In operation, a computer 134 which is operatively connected to user interface 140, receives an input from user interface 140 to commence an NMR pulse sequence. Computer 134 then sends a signal to digital to analog converter 172 to commence an RF frequency pulse to be emitted from RF source 160 and is mixed with mixer 162 connected to digital to analog converter 172 and amplified. The RF pulse thus emitted is then sent to the NMR module 122 and used to excite the nuclei at one or several spectrometer frequencies of 300 MHz or less. The RF coils 126a and 126b are tuned to receive NMR signals (free induction decay, FID, of the realigned magnetic fields of the nuclei excited with the radio frequency pulse). The signal thus detected is amplified one to several orders of magnitude using amplifier's 180 and 178. The output signal is then converted from analog to digital using converter 170 and the resultant electrical signals are Fourier transformed (FT) to provide a time-frequency transformation. In various embodiments, homonuclear and heteronuclear pulse sequences are Fourier transformed to obtain NMR spectroscopy multidimensional 2-D and 3-D chemical information.

In one embodiment, FIG. 4, provides an exemplary NMR module 122a comprising a permanent magnet apparatus referred to as a Halbach magnet. In this aspect, a Halbach magnet comprises a bore of sufficient diameter to enable the inclusion within such bore a sample conduit 125 (not shown) and an analysis volume that is placed within the bore of the permanent magnet 127. Magnet 127 can provide a bore measuring 1 mm-10 mm, preferably from about 1 mm to about 5 mm. In one embodiment, using an indirect RF coil configuration, coil 126b is immediately adjacent to the sample contained within the analysis volume 200. Extending outwards, RF coil 126b is encircled by RF coil 126a. Surrounding RF coils 126b and 126a is a pulsed-field gradient coil 210. Surrounding pulsed-field gradient coil 210 is one or more shim coils 220. Lastly, the analysis volume 200, RF coils 126b and 126a, pulsed-field gradient coil 210, and one or more shim coils 220 are all surrounded by permanent magnet 127 which provides a static magnetic field strength of 0.5 T to about 7 T and the NMR module itself provides a spectrometer frequency of 300 MHz or less. The static magnetic field ($B_0$) is perpendicular to the magnetic field generated by the RF coils 126b and 126a. In some embodiments, the NMR module 122 can be thermally regulated using heating and cooling devices 110, which can illustratively include a Peltier element in contact with the analysis volume 200, sample conduit 125 and magnet 127.

Figure 6A:
FIG. 6A-6D depicts a schematic representation of the synthesis of a flexible NMR device for use in one embodiment of the methods and devices in accordance with the teachings of the present disclosure.
Figure 6B:
Figure 6C:
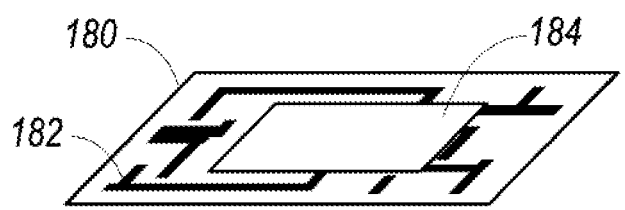
Figure 6D:
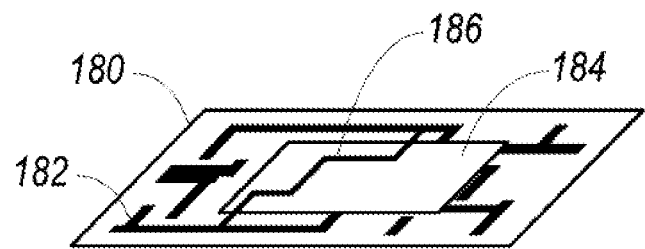
Figure 6E:
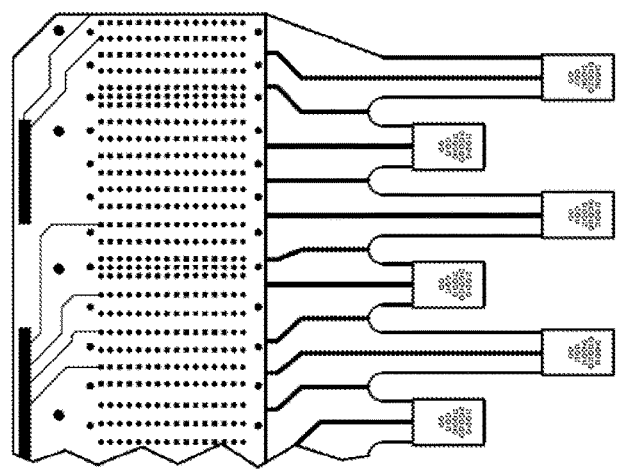
FIG. 6E depicts an elevation view of a flexible NMR module in accordance with the teachings of the present disclosure.

In some embodiments, a flexible NMR module 122a can be planarized and made into a flexible construct that may be circularized around a sample conduit 125 and analysis volume 200 and actuated with a magnetic field and pulsed RF pulses to perform NMR spectrometry on a sample within the NMR module 122a. In one embodiment, as shown in FIGS. 6a-6e, a NMR module 122 of the present invention can include a planar substrate 180 that is flexible can serve to mount all of the required RF coils, the planar substrate would then be circularized around the analysis volume 200 (not shown) to provide a RF coil. In one embodiment, the flexible planar substrate 180 can include a polymer material that can be heated and cooled to 0° C. to 60° C. without any alteration in tensile strength. In one embodiment, the planar substrate 180 can comprise a polyethylene terephthalate, film measuring 0.5-5 cm tail by 0.5 to 5 cm wide and 0.001 min to 5 mm thick. An insulator 184 can be overlaid over at least a portion of printed RE coil 182. One or more RE coil layer(s) 186 can then be printed between insulator 184. The insulator 184 can also be printed between a layer of pulsed-field gradient coil 210 (not shown) and or a layer of shim coil 220 (not shown) prior to printing the RF coil(s) 186. A completed NMR module 122 is shown in FIG. 6e, in some embodiments, the flexible NMR module 122a can be wrapped around a sample conduit 125 (not shown) and provide an analysis volume 200 (not shown) containing a sample for NMR interrogation. The flexible NMR module 122a can be connected to the appropriate signal transmitter and receiver 132 as shown in FIG. 5 and perform NMR spectroscopy on a desired sample within the NMR device 100.

c. The Computer

As shown in FIG. 1, the NMR device 100 of the present invention also includes a computer 134. The computer 134 can typically comprise of a processor, for example a microprocessor or computer processor or a computer having one or more microprocessors, one or more memory buffers, RAM, or ROM, a data storage device, and a means for inputting signals and/or data obtained from the signal transmitter/receiver 132, for example, electronic or digital signals and/or data operable to perform a plurality of Fourier transformations, record 1D, 2D, 3-D and 4D spectra, including 1D 1H, 1D 13C, 1D or 2D 1H-1H TOCSY (correlation spectroscopy), 1D or 2D 1H-13C HSQC (heteronuclear single quantum coherence), spin-state-selective HSQC, 1D or 2D 1H-13C HMQC (heteronuclear multiple quantum coherence), 1D or 2D 1H-15N HSQC, 1D or 2D 1H-15N spin-state-selective HSQC, 1D or 2D 1H-15N HMQC, and 1D NOE (nuclear Overhauser effect spectroscopy) difference, 2D 1H-1H NOESY (nuclear Overhauser effect spectroscopy; mixing time=10-1000 msec), 1D, 2D, or 3-D 13C-editted and/or 15N-editted NOESY-HSQC or 1D, 2D, or 3-D 13C-editted and/or 15N-editted NOESY-HMQC spectra in D2O and/or H2O/D2O mixture to the analysis module.

In some embodiments, the computer 134 can be programmed to perform routine tasks to acquire NMR signals and calculate chemical shifts of the various nuclei of the polynucleotide under study using one or more computer programs. Software stored on the computer 134 may be used to determine other NMR data in addition to chemical shifts for use in the methods of the present invention directly from the NMR spectrum. Such spectra are sufficient to determine various standard structural NMR restraints, for example, chemical shift data, residual dipolar coupling (RDC)s, J coupling, NOE and the like. The computer 134 may further comprise a motherboard containing a plurality of input/output devices, for example, a central processing unit, a graphics chip, a memory, memory bank, or a memory buffer, a program storage device, for example, RAM, ROM, a disc drive, a flash drive, or some other medium operable to store a computer program. In some embodiments, computer software programs that can be employed to determine data or portions of data required to determine a 2-D, 3-D or 4-D structure, or data related to the 3-D-structure of a polynucleotide can include: SHIFTS, SHIFTX, NUCHEMICS, RAMSEY MC-Sym, ROSETTA, Topspin (Bruker), VNMRJ (Agilent), SPARTA, SPARKY. Other common communication input/output devices, such as a keyboard, mouse and the like may also be connected or interfaced with computer 134. In some embodiments, the computer 134 comprises one or more software programs operable to automate the liquid sample handling and NMR experimental set-up, regulate sample temperature, execute NMR electronics, acquire NMR FID (free induction decay) data, Fourier transform and processing the FID, pick peaks from a past or to be recorded NMR spectra, determination of internal reference peak, determination of chemical shift, peak intensity or volume, and peak splitting (J couplings and residual dipolar couplings), RNA structure prediction, perform molecular dynamics simulation and software to enable chemical shift directed polynucleotide structure determination, software to calculate binding affinities (or dissociation constant, $K_d$) of one or more compounds operable to bind with a selected polynucleotide.

With reference to FIG. 1, the NMR device 100 can optionally also include a user interface 140 having capabilities to interact with the software stored in the computer 134. In some embodiments, the user interface 140 has electronic output signal capability or software instructions operable to interact with the computer 140, which in turn may be able to control and execute instructions for the sample handling device 118, the NMR module 122 and the sample temperature controller 110, PFG controller 300 and the shim controller 400. In some embodiments, the user interface 140 can select for one or more samples to be withdrawn from one or more sample storage devices 114, for example, one or more cartridges 116, select the chemical environment of the sample, by further electing one or more auxiliary agents from the stored reagents 112 in the NMR device 100.

In some embodiments, the user interface 140 comprises a graphical user interface (GUI) for example, a touch screen interface that provides a series of options for further instructing the device of the present invention to perform one or more liquid sample manipulations, one or more NMR analyses and return one or more data values, images, computer generated graphics, data representations or compilation of data values, for example, one or more of: the 2D & 3-D structure of a polynucleotide of interest, assess heterogeneity of a polynucleotide sequence and whether it folds into one or multiple structural forms; structurally map out RNA/DNA-protein and RNA/DNA-ligand interactions; measure the binding affinities/specificities between the RNA/DNA and protein, ligand and other molecules; assign NMR resonances; screen a library of small molecules, biological, or other compounds for binding to the RNA/DNA; evaluate the similarities in the 2D and 3-D structure of different nucleotide sequences; evaluate presence/absence of specific tertiary interactions; evaluate presence/absence of specific elements of secondary and 3-D atomic resolution structure; evaluate how changes in physiological conditions such as temperature and pH affect RNA/DNA structure; evaluate protonation/tautomer state of base-pairs; and evaluate structure of excited states (such as transient Hoogsteen base-pairs).

In various embodiments, the NMR device 100 optionally comprises a sample storage device, for example, a cartridge having a proprietary insertion mechanism so that it is only fits the intended instrument or device. In various embodiments, the cartridge can contain a predefined polynucleotide selectively isotopically labeled with a nucleotide, wherein the selectively labeled polynucleotide is then further processed using the device and methods defined herein. In some embodiments, the sample storage device comprises a microfluidics component operable to load a predefined volume of polynucleotide labeled sample into the device.

The NMR device 100 of the present invention when using the methods described herein, is operable to provide information and/or data related to the 2-D & 3-D atomic resolution structure of a polynucleotide of interest, assess heterogeneity of a polynucleotide sequence and whether it folds into one or multiple structural forms; structurally map out RNA/DNA-protein and RNA/DNA-ligand interactions; measure the binding affinities/specificities between the RNA/DNA and protein, ligand and other molecules; assign NMR resonances; screen a library of small molecules, biological, or other compounds for binding to the RNA/DNA; evaluate the similarities in the 2-D and 3-D structure of different nucleotide sequences; evaluate presence/absence of specific tertiary interactions; evaluate presence/absence of specific elements of secondary and 3-D atomic resolution structure; evaluate how changes in physiological conditions such as temperature and pH affect RNA/DNA structure; evaluate protonation/tautomer state of base-pairs; evaluate structure of excited states (such as transient Hoogsteen base-pairs; and generate); and generate pairs; evaluate structure of excited states (such as transient Hoogsteen base-pairs; and generate Dynamic Atomic-scale RNA drug targets (DARTs) and measurement of anisotropic properties useful in refining the structure determination using other NMR constraints/techniques (for example, residual dipolar couplings (RDCs), residual chemical shift anisotropy RCSA's and the like).

In some embodiments, the components of the device, i.e. the sample handling and heating and cooling device 118, the NMR module 122, or 122a, the signal transmitter and receiver 132, the computer 134, and the user interface 140 can all be combined into one integral device 100, or some of the components may exist as separately or some combination thereof. Similarly, optional components pulsed-field gradient controller 300 and shim controller 400 can also be combined into the integral device 100, or they may exist as separate components or some combination thereof.

(B) Method for Studying Selected Biomolecules

In discussion of the various methods of the present invention, the labeling techniques and the analysis of the labeled samples using NMR. In various embodiments, the methods for determining a 2-D structure and/or a 3-D atomic structure can utilize NMR devices having any commercially available spectrometer frequencies, for example, at a $^1$H Larmor frequency of about 900 MHz to about 20 MHz, or about 900 MHz, about 800 MHz, about 700 MHz, about 600 Mhz, about 500 MHz, about 400 MHz, about 300 MHz, about 200 MHz, about 100 MHz, about 75 MHz, about 50 MHz, or about 20 MHz, can be used to determine the structure of a biomolecule, for example, a polynucleotide. Solely for the purpose of convenience, the disclosure of the present methods will be exemplified with the use of polynucleotides, but the methods described herein are applicable to determine the interactions or structure of a protein or a polypeptide as the target or desired biomolecule of interest. Methods for selectively labeling proteins and polypeptides are known in the art. In some embodiments, the methods of the present technology can be performed using an NMR module operable to provide a $^1$H Larmor frequency of 300 MHz or less.

In one embodiment, a significant advantage of the present invention is the use of lower magnetic fields (for example, 300 MHz or less), which can significantly shorten the repetition delay and the total experimental time can be reduced to ¼-⅕ of that of high fields because the repetition delay depends on T1 relaxation time which is significantly shorter at low magnetic field (i.e. T1 relaxation time at 100 MHz is more than 6 times shorter than that of 600 MHz for molecules of correlation time of 4-8 ns (oligonucleotides of 25-50 bases)). This T1 relaxation time difference at between high and low magnetic fields becomes larger as molecular weight or size of a molecule increases. Within given time, 4-5 times more measurements can be repeated and added at low magnetic fields to yield signal-to-noise gain of factor of 2.

In one embodiment, the present invention provides a method for the synthesis of a uniformly labeled, stable isotope containing polynucleotide. In one embodiment, a method for determining the 3-D atomic resolution structure of a polynucleotide, the method comprises:
  (a) providing a polynucleotide sample comprising a plurality of polynucleotides, the plurality of polynucleotides having an identical nucleotide sequence, wherein each polynucleotide comprises at least one nucleotide isotopically labeled with one or more atomic labels selected from the group consisting of $^2H$, $^{13}C$, $^{15}N$, $^{19}F$ and $^{31}P$;
  (b) obtaining a NMR spectrum of the polynucleotide sample using a NMR device;
  (c) determining a chemical shift of the one or more atomic labels; and determining a 2-D or a 3-D atomic resolution structure of the polynucleotides from the chemical shifts determined in step (c).

As used herein a nucleic acid or polynucleotide can include DNA, RNA, and mimetic of DNA and RNA and DNA and RNA sequences comprising one or more modified nucleobases or nucleotides. In some embodiments, the DNA can be single or double stranded, genomic DNA, cDNA and variations thereof. In some embodiments, the RNA can include single or double stranded RNA, mRNA, mitochondrial RNA ribosomal RNA and variations thereof. Generally speaking, the term "nucleic acid" can encompasses polynucleotides, oligonucleotides, probes, modified polynucleotides, and so on. Typically, these nucleic acid constructs useful in the methods of the present invention can comprise from about 3 to about 500 base pairs or nucleotides (nt), preferably from about 5 to about 200 base pairs or nucleotides, more preferably from about 6 to about 100 base pairs or nucleotides. While the present methods, device and systems apply equally to DNA nucleic acids as it does to RNA nucleic acids, the methods exemplified and illustrated herein are described with RNA nucleic acids.

Figure 2:
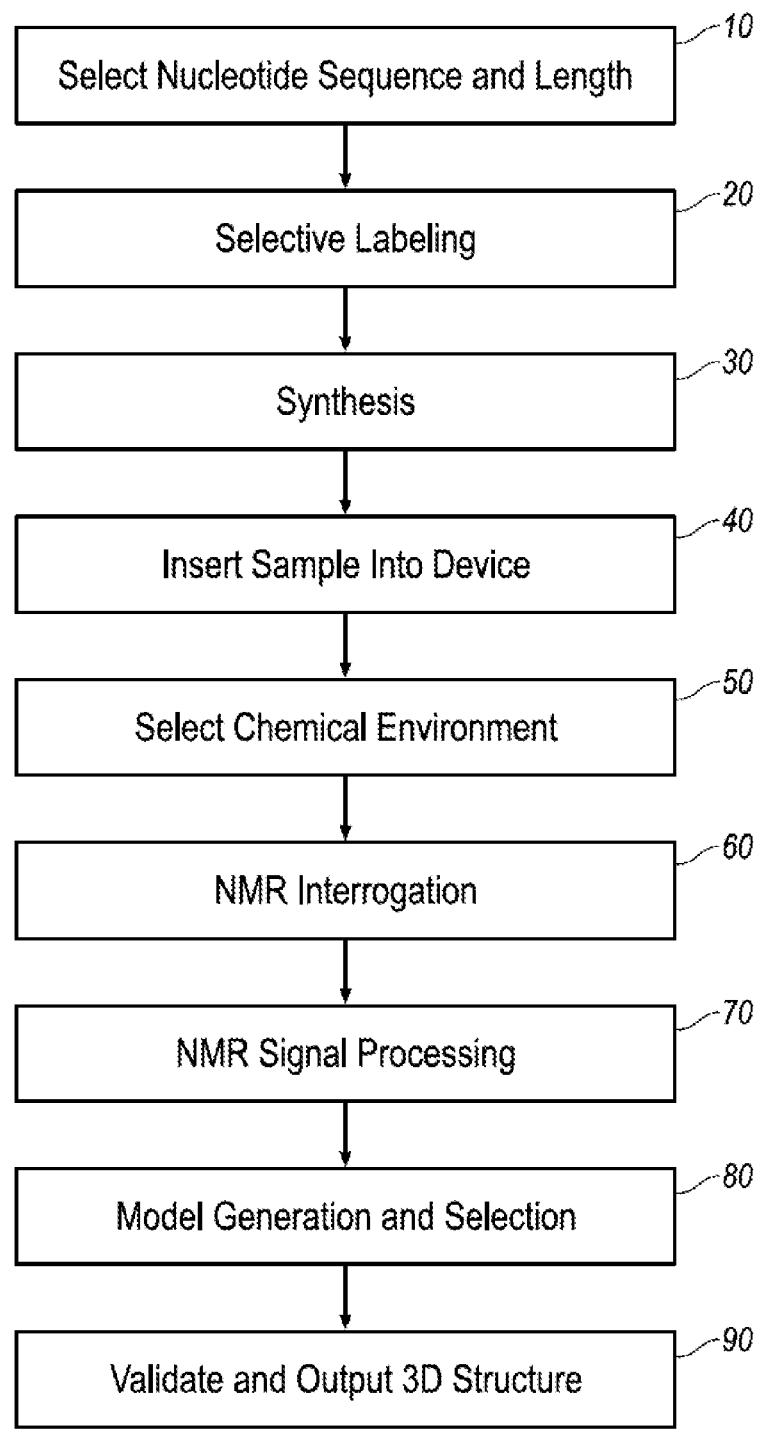
FIG. 2 depicts a bar flowchart of the various steps used in one embodiment in accordance with the teachings of the present disclosure.

With reference to FIG. 2 an exemplary method for determining the 3-D structure, dynamics, biophysical and biochemical characteristics of a biomolecule, for example a polynucleotide, for example, an RNA polynucleotide comprises: (10) selecting a nucleotide sequence, (20) selectively labeling one or more polynucleotides, (30) synthesizing the one or more labeled polynucleotides, (40) inserting the one or more polynucleotides into an NMR device, (50) selecting a chemical environment of the one or more labeled polynucleotides for the NMR interrogation procedure; (60) performing NMR analysis on the one or more labeled polynucleotides using the NMR device of the present invention, (70) process the NMR signals obtained for the one or more labeled polynucleotides, (80) generating one or more 3-D models and performing an analysis to select a 3-D model that best fits the experimental data and the predicted chemical shifts, and (90) validating the selected model with other NMR data and outputting the validated 3-D structure of the polynucleotide in the selected chemical environment.

In another embodiment a number of small molecule-bound bimolecular structures can be determined for uses comprising computer aided drug discovery efforts, which commonly rely on biomolecular structures determined when bound to a small molecule. Representative small molecules include aminoglycosides, flavin/flavonoids, intercalators (e.g. acridine orange, proflavine and the like), and tetracylines (e.g. tetracycline, doxycycline and the like). In order to identify which small molecules interact with the biomolecule, one could initially synthesize a uniformly isotopically labeled biomolecular sample, mix each small molecule at a ratio that one would expect to see changes in NMR signals for relatively tight binding small molecules (for a low µM $K_d$, a ratio of 2:1 or 4:1 could be used), collect the NMR data such as chemical shifts and/or NOEs, compare the NMR data of the biomolecule in the presence of the small molecule to the NMR data of the biomolecule in the absence of the small molecule, and select small molecules that cause significant changes in the NMR data (typically a change in one chemical shift line width or significant reduction in the NOE resonance intensity when comparing the biomolecule NMR data in the absence and presence of the small molecule is significant). Alternatively, the NMR data of the small molecule could be monitored and similar perturbations observed on addition of the biomolecule of interest, where the biomolecule could be non-isotopically labeled. The same solution conditions (e.g. buffer or solubilization solution) for each sample should be used to minimize random noise due to differences in solution environments.

In one embodiment, the present invention provides a method for determining the 3-D atomic resolution structure of a polynucleotide when bound to a small molecule, ligand or other chemical entity for purposes comprising computer-aided drug design, the method comprises:
  (a) providing a polynucleotide sample comprising a plurality of polynucleotides, the plurality of polynucleotides having an identical nucleotide sequence, wherein each polynucleotide comprises at least one nucleotide isotopically labeled with one or more atomic labels selected from the group consisting of $^2H$, $^{13}C$, $^{15}N$, $^{19}F$ and $^{31}P$;
  (b) admixing the polynucleotide sample with the ligand forming a plurality of bound complexes;
  (c) obtaining a NMR spectrum of the bound complexes using a NMR device;
  (d) determining a chemical shift of the one or more atomic labels; and
  (e) determining the 3-D atomic resolution structure of the polynucleotides from the chemical shifts determined in step (d).

In another embodiment, with reference to FIG. 2 an exemplary method for determining the 3-D structure and biochemical characteristics of a biomolecule, for example a polynucleotide, for example, an RNA polynucleotide when bound to a small molecule ligand comprises: (10) selecting a nucleotide sequence, (20) selectively labeling one or more polynucleotides, (30) synthesizing the one or more labeled polynucleotides, (40) inserting the one or more polynucleotides into the NMR device, (50) selecting a chemical environment of the one or more labeled polynucleotides for the NMR interrogation procedure, which comprises one or more small molecules that have the potential to bind the biomolecule of interest; (60) performing NMR analysis on the one or more labeled polynucleotides using the NMR device of the present invention, (70) process the NMR signals obtained for the one or more labeled polynucleotides, (80) generating one or more 3-D models and performing an analysis to select a 3-D model that best fits the experimental data and the predicted chemical shifts, and (90) validating the selected model with other NMR data and outputting the validated 3-D structure of the polynucleotide in the selected chemical environment.

1. Preparation of Selectively Labeled Polynucleotides for Structure Characterization The present methods for the determination of structural information of a biomolecule in part can be performed using any commercially available NMR spectrometer having a spectrometer or $^1$H Lamor frequency of about 900 MHz to about 20 MHz, there are several unexpected advantages using a low field NMR device, for example, an NMR device having a spectrometer frequency of 300 MHz or less. In some embodiments, the methods are derived from the surprising finding that low field NMR can be employed to obtain structurally detailed information concerning a complex structure, such as a polynucleotide, if the sample is appropriately labeled with one or more isotopically labeled nucleotides. Combining the use of low field NMR (i.e. a $^1$H Larmor frequency of 300 MHz or less) with selective labeling of the sample provides a sufficient resolution that permits NMR studies of complex 3-D structures using chemical shift information derived from innovative lab-benchtop NMR devices as described herein. Advantages offered by the presently described devices when used in the methods of the present invention can include: (i) Relaxation issues (shortened relaxation delay due to T1 benefit), (ii) improved NMR sensitivity (use of two or more microcoils tuned for different frequencies for mass-sensitivity), and (iii) selective labeling of nucleotides to derive a 3-D structure of the polynucleotide in question from background "noise". The present methods and device also provide customary information or NMR interactions that may be pertinent to the resolution and determination of 3-D atomic resolution structure of a biomolecule under study, such as residual dipolar couplings, nuclear Overhauser effect(NOE) data, measurement of residual chemical shift anisotropies (RCSA) and J-coupling or scalar coupling data.

In one embodiment, the present invention provides a method for determining one or more specific isotopic labeling positions of one or more nucleotides within a polynucleotide sequence for the determination of 3-D atomic resolution structure or collecting other NMR interaction data of a polynucleotide. In some embodiments, the method comprises: (a) providing one or more polynucleotides each of the one or more polynucleotides having an identical polynucleotide sequence, wherein each of the one or more polynucleotides comprises one or more nucleotides labeled with an isotopic label comprising, $^2$H, $^{13}$C, $^{15}$N, $^{19}$F or $^{31}$P; (b) generating a plurality of structures of the polynucleotide sequence using a computational algorithm (e.g. MC-Sym); (c) identifying one or more region(s) on each of the plurality of polynucleotide structures that exhibit a large structural variation using metrics comprising an $S^2$<0.8 and/or RMSF>0.5 Å; (d) calculating a plurality of chemical shifts from regions of the predicted structures having a large structural variation using a chemical shift predictor; such as Nymirum's Random Forest Predictors (RAMSEY), SHIFTS, NUCHEMICS, and QM methods from the predicted structures; and (e) determining one or more specific isotopic labeling positions on each of the polynucleotide sample(s) such that the chemical shift dispersion is maximized and/or the number of samples is minimized.

In some embodiments, the number of isotopically labeled polynucleotides synthesized for the polynucleotide sample is equal to the number of nucleotides in the polynucleotide, wherein each synthesized polynucleotide has a different nucleotide labeled with the one or more atomic labels. In some embodiments, the nucleotides labeled with one or more atomic labels can include nucleotides having a predicted or an experimentally determined structural heterogeneity or a predicted or an experimentally determined structural heterogeneous region. As used herein, a structural heterogeneous region, is defined as: one or more contiguous nucleotides in the polynucleotide sequence in which the polynucleotide 2-D structure of the one or more contiguous nucleotides is any one or more of:

(a) known or predicted to participate in labile or unstable base-pairs,
(b) exist in non-helical structures such as a bulge, internal loop, apical loop, or any other junction,
(c) exist in non-Watson-Crick base-pairs,
(d) are known or predicted to have a poorly defined secondary structure, or
(e) neighbor any of the polynucleotide structural elements defined in (a-d).

A structural heterogeneous region indicative of a large 2-D or 3-D structural hetereogeneity can be calculated using various metrics such as $S^2$ order parameters, root mean squared fluctuation (RMSF) etc. In calculation of 2-D structural heterogeneity, a set of putative 2-D structures (e.g 10 low energy predicted models from MC-Fold) can be used. For each nucleotide in the polynucleotide putative 2-D structure, one or more nucleotides can be identified as a base pair partner(s). The 2-D structural heterogeneity then can be defined as a real number for each base: [number of unique base pair partner(s)]/[total number of putative 2-D structures], where a larger number indicates a more heterogeneous 2-D structure of the particular nucleotide. In calculation of 3-D structural heterogeneity, a set of putative 3-D structures (e.g. 10 low energy predicted models from MC-Sym) can be used. The chosen structural parameter (e.g. $S^2$ or RMSF) can be calculated based on the putative 3-D structures. In some embodiments the putative structures can be superimposed using a common set of residues/atoms, for example all heavy atoms in the helical region(s) of the RNA of interest, prior to calculating the structural heterogeneity. In another embodiment, the structural heterogeneity metric can then be normalized to the residue with the highest predicted structural fluctuations. Those residues with the highest relative fluctuation can be selected for further investigation of predicted chemical shifts, which for example could be all residues with $S^2$<0.8 and/or RMSF>0.5 Å. The cutoffs used to determine the labels that will be isotopically labeled can vary according to the complexity and/or structural variability of the RNA of interest. The chemical shifts of atoms in the residues selected would be calculated using a chemical shift predictor such as Nymirum's Random Forest Predictors (RAMSEY), SHIFTS, NUCHEMICS, and QM methods and labeling positions on each of the polynucleotide sample(s) selected such that the chemical shift dispersion is maximized and the number of samples is minimized.

In one embodiment, one could use the $S^2$ order parameter, which varies from 1 to 0 for rigid and isotropic motions respectively, to determine the residues to isotopically label. In one embodiment, after superimposing the 10 low energy structures from MC-Sym predictions using a common set of residues/atoms, for example all heavy atoms in the helical region(s) of the RNA of interest, the $S^2$ order parameter can be calculated for chosen bonds of interest (e.g. N1H1/N3H3, C1'H1', C5H5, C6H6, C8H8, C2H2 etc.) using the equilibrium expression:

$$S_{eq}^2 = \frac{\langle 1/r^3 \rangle^2}{\langle 1/r^6 \rangle} \left[ \frac{3}{2} (\langle \hat{\mu}_x^2 \rangle^2 + \langle \hat{\mu}_y^2 \rangle^2 + \langle \hat{\mu}_z^2 \rangle^2) + (\langle \hat{\mu}_x \hat{\mu}_y \rangle^2 + \langle \hat{\mu}_z \hat{\mu}_x \rangle^2) - \frac{1}{2} \right]$$

where r is the bond length of the bond of interest, and $\mu_n$ is coordinate component of the bond of interest where n=x, y, or z direction. After calculation of $S^2$, one may select all residues with bonds have $S^2$ less than a cutoff value (e.g. $S^2$<0.8). Alternatively, one could independently normalize the $S^2$ values for each bond vector type such that the $S^2$ of the most flexible residue is 0. Then one could select the residues with the lowest $S^2$ values by selecting an internal cutoff (e.g. $S^2$<0.8). In another embodiment, one could calculate the center of mass for each residue and repeat the $S^2$ calculation using the center of mass rather than individual bond vectors of the residue(s).

In another embodiment, the RMSF, which is always greater than 0, can be used to determine a structural heterogeneous region or regions of a polynucleotide with a large structural variation. In one embodiment, after superimposing an exemplary set of 10 low energy structures from MC-Sym predictions using a common set of residues, for example, all heavy atoms in the helical region(s) of the RNA of interest, the RMSF can be calculated for chosen structural parameters of interest using the equation:

$$RMSF = \sqrt{\frac{1}{N}\sum_{i=1}^{N}(j_i - \bar{j}_i)^2}$$

where N is the number of polynucleotide structures under consideration and j is a structural feature such as atomic position, residue center of mass position etc., and $\bar{j}$ denotes the average of the structural feature averaged over the N structures. After calculation of RMSF, one may select all residues with RMSF greater than a cutoff value (e.g. RMSF>0.5 Å).

In one embodiment, to calculate the minimized chemical shift overlap (d), where d=min($|\delta_i-\delta_j|$) where $\delta_i$, $\delta_j \in \{\delta_{labeled\ positions}^{calculated}\}$, a sampling algorithm such as the Kennard-Stone algorithm (R. W. Kennard, L. A. Stone, Computer aided design of experiments, Technometrics 11 (1969) 137-148, the disclosure of which is incorporated herein by reference in its entirety) can be adopted to rank a list of possible combination of labeling positions on each of the polynucleotide sample. For example, each labeled position (e.g. an atomically labeled nuclei) is considered as a point in the Kennard-Stone algorithm. The algorithm works as follows: first find the two positions most dispersed or largest dispersion (d) in the trial set. For each candidate position, find the smallest dispersion (d) to any position already selected. Select that position for the training set which has the largest of these smallest dispersion. This algorithm always gives the same result, due to the two starting positions which are always the same. The results of the Kennard-Stone algorithm would provide the fewest number of necessary polynucleotides needed to be synthesized while maintaining maximum chemical shift dispersion.

In other embodiments, the Kennard-Stone algorithm could be used to select more than one residue to be isotopically labeled that does not maintain maximum chemical shift dispersion, thus affording less spectral resolution, with the goal of reducing the number polynucleotides to be synthesized.

In another embodiment, generation and selection of a structural model step (80) can include the steps:
1. select polynucleotide sequence of interest
2. predict 2-D structure using any 2-D structure predicting algorithm, for example, contrafold, Vienna RNA package, centroid-fold, RNAstructure, ContextFold, IPKnot, MC-Fold and the like;
3. generate a 3-D model using any 3-D structure predicting algorithm, for example, MC-Sym, NAB (distance geometry), Rosetta FARFAR, NAST, RNA builder, and the like;
4. determine the minimum energy conformation of the structure using molecular mechanics software, for example, NAB, NAMD, GROMACS, TINKER, CHARMM, AMBER, and the like;
5. calculate the regions of the RNA that exhibit large structural variation using metrics such as $S^2$ and/or RMSF, where large structural variation is defined as $S^2$<0.8 and/or RMSF>0.5 Å.
6. For regions of the RNA with large structural variations, calculate the chemical shifts from each structure using chemical shift calculation software, for example, Nymirum's Random Forest Predictors (RAMSEY), SHIFTS, NUCHEMICS, and QM methods;
7. Using a computational algorithm(s)/software, such as the Kennard-Stone algorithm, select one or more residues that will be isotopically labeled such that the chemical shift dispersion is maximized, or is as maximized as possible, and the number of samples is minimized.

In some embodiments, a structural heterogeneous region of a 3-D polynucleotide structure is defined as: one or more contiguous nucleotides in the polynucleotide sequence in which the polynucleotide 3-D structure of the one or more contiguous nucleotides is any one or more of:
(a) known or predicted to participate in labile or unstable base-pairs,
(b) exist in non-helical structures such as a bulge, internal loop, apical loop, or any other junction,
(c) exist in non-Watson-Crick base-pairs,
(d) are known or predicted to have a poorly defined tertiary structure using metrics such as an $S^2$<0.8, an RMSF>0.5 Å, or a root mean square deviation>2.0 Å, or
(e) a neighbor any of the polynucleotide structural elements defined in (a-d).

In some embodiments, an exemplary method for calculating a 2-D structural heterogeneous region can include an illustrative example using a set of putative 2-D structures (e.g 10 low energy predicted models from MC-Fold). For each nucleotide in the polynucleotide putative 2-D structure, one or more other nucleotides can be identified as a base pair partner(s). The 2-D structural variance then can be defined as a real number for each base: [number of unique base pair partner(s)]/[total number of putative 2-D structures], where a larger number indicates a more heterogeneous 2-D structure of the particular nucleotide.

In another illustrative example of how to calculate 2-D structural heterogeneous region involves the calculation of a 3-D structural heterogeneous region, wherein a set of putative 3-D structures (e.g. 10 low energy predicted models from MC-Sym) can be used. The chosen structural parameter (e.g. $S^2$ or RMSF) can be calculated based on the putative 3-D structures. In some embodiments the putative structures can be superimposed using a common set of residues/atoms, for example, all heavy atoms in the helical region(s) of the RNA of interest, prior to calculating the structural heterogeneity. In another embodiment, the structural heterogeneity metric can then be normalized to the residue with the highest predicted structural fluctuations. Those residues with the highest relative fluctuation can be selected for further investigation of predicted chemical shifts, which for example could be all residues with $S^2<0.8$ and/or RMSF>0.5 Å. The cutoffs used to determine the labels that will be isotopically labeled can vary according to the complexity and/or structural variability of the RNA of interest.

A large structural heterogeneous region in tertiary structure can be calculated using various metrics such as $S^2$ order parameters, root mean squared fluctuation (RMSF) etc. In some embodiments, the calculation of structural heterogeneity can include a set of putative structures (e.g. 10 low energy predicted models from MC-Sym). The chosen structural parameter can be calculated based on the set of putative structures. In some embodiments the putative structures can be superimposed using a common set of residues/atoms, for example all heavy atoms in the helical region(s) of the RNA of interest, prior to calculating the structural heterogeneous region. In another embodiment, the structural heterogeneity metric would then be normalized to the residue with the highest predicted structural fluctuations. Those residues with the highest relative fluctuation would be selected for further investigation of predicted chemical shifts, which for example could be all residues with $S^2<0.8$ and/or RMSF>0.5 Å. The cutoffs used to determine the labels that will be isotopically labeled can vary according to the complexity and/or structural variability of the RNA of interest. The chemical shifts of atoms in the residues selected would be calculated using a chemical shift predictor such as Nymirum's Random Forest Predictors (RAMSEY), SHIFTS, NUCHEMICS, and QM methods and labeling positions on each of the polynucleotide sample(s) selected such that the chemical shift dispersion is maximized and the number of samples is minimized.

In one embodiment, one could use the $S^2$ order parameter, which varies from 1 to 0 for rigid and isotropic motions respectively, to determine the residues to isotopically label. After superimposing the 10 low energy structures from MC-Sym predictions using a common set of residues/atoms, for example, all heavy atoms in the helical region(s) of the RNA of interest, the $S^2$ order parameter can be calculated for chosen bonds of interest (e.g. N1H1/N3H3, C1'H1', C5H5, C6H6, C8H8, C2H2 etc.) using the equilibrium expression:

$$S_{eq}^2 = \frac{\langle 1/r^3 \rangle^2}{\langle 1/r^6 \rangle}\left[\frac{3}{2}(\langle \hat{\mu}_x^2 \rangle^2 + \langle \hat{\mu}_y^2 \rangle^2 + \langle \hat{\mu}_z^2 \rangle^2) + (\langle \hat{\mu}_x \hat{\mu}_y \rangle^2 + \langle \hat{\mu}_z \hat{\mu}_x \rangle^2) - \frac{1}{2}\right]$$

where r is the bond length of the bond of interest, and $\mu_n$ is coordinate component of the bond of interest where n=x, y, or z direction. After calculation of $S^2$, one may select all residues with bonds have $S^2$ less than a cutoff value (e.g. $S^2<0.8$). Alternatively, one could independently normalize the $S^2$ values for each bond vector type such that the $S^2$ of the most flexible residue is 0. Then one could select the residues with the lowest $S^2$ values by selecting an internal cutoff (e.g. $S^2<0.8$). In another embodiment, one could calculate the center of mass for each residue and repeat the $S^2$ calculation using the center of mass rather than individual bond vectors of the residue(s).

In another embodiment, one could use the RMSF, which is always greater than 0, to determine regions of large structural variation. After superimposing the 10 low energy structures from MC-Sym predictions using a common set of residues, for example all heavy atoms in the helical region(s) of the RNA of interest, the RMSF can be calculated for chosen structural parameters of interest using the equation:

$$RMSF = \sqrt{\frac{1}{N}\sum_{i=1}^{N}(j_i - \bar{j}_i)^2}$$

where N is the number of polynucleotide structures under consideration and j is a structural feature such as atomic position, residue center of mass position etc., and $\bar{j}$ denotes the average of the structural feature averaged over the N structures. After calculation of RMSF, one may select all residues with RMSF greater than a cutoff value (e.g. RMSF>0.5 Å).

In one embodiment, to calculate the maximized chemical shift dispersion (d), where $d=\min(|\delta_i-\delta_j|)$ where $\delta_i$, $\delta_j \in \{\delta_{labeled\ positions}^{calculated}\}$, a sampling algorithm such as the Kennard Stone algorithm (R. W. Kennard, L. A. Stone, Computer aided design of experiments, Technometrics 11 (1969) 137-148) can be adopted to rank a list of possible combination of labeling positions on each of the polynucleotide sample. For example, each labeled position is considered as a point in the Kennard-Stone algorithm. The algorithm works as follows: first find the two positions most dispersed or largest dispersion (d) in the trial set. For each candidate position, find the smallest dispersion (d) to any position already selected. Select that position for the training set which has the largest of these smallest dispersion. This algorithm always gives the same result, due to the two starting positions which are always the same. The results of the Kennard-Stone algorithm would provide the fewest number of necessary polynucleotides needed to be synthesized while maintaining maximum chemical shift dispersion. Using the above referenced methodologies for identifying a region of a polynucleotide for selective labeling, the present invention provides a method for selectively labeling a polynucleotide for NMR analysis, the method comprising:

In other embodiments, the Kennard-Stone algorithm could be used to select more than one residue to be isotopically labeled that does not maintain maximum chemical shift dispersion, thus affording less spectral resolution, with the goal of reducing the number polynucleotides to be synthesized.

In some embodiments, illustrative methods for determining the position on the polynucleotide sequence for isotopically labeling one or more nucleotides with one or more atomic labels can include: (1) determining one or more 2-D or 3-D models of the polynucleotide sequence using a 2-D or 3-D structure predicting algorithm, respectively. As used herein, a 2-D structure prediction algorithm generally relates to an algorithm(s) employed in structure prediction software such as: MC-Fold, MC-Fold-DP, Mfold, CentroidFold, ContextFold, IPKnot, ContraFold, MaxExpect, ProbKnot, Sfold, or any other polynucleotide secondary structure prediction approach, and a 3-D structure prediction algorithm is defined as the algorithm(s) employed in software such as: MC-Sym, NAB, Rosetta FARFAR, NAST, RNA builder or any other 3-D RNA structural prediction approach. Methods and software for 2-D and 3-D structure prediction algorithms are described in: (MC-Fold): Parisien M, Major F. Nature 2008, 452(7183):51-55; (MC-Fold-DP): Höner zu Siederdissen, Christian, Stephan H. Bernhart, Peter F. Stadler, and Ivo L. Hofacker. 2011. Bioinformatics 27: 129-36; (Mfold): M. Zuker & A. B. Jacobson. RNA 4, 669-679, 1998; (CentroidFold): Sato K. et al. Nucleic Acids Research, 2009, Vol. 37, Web Server issue; (ContextFold): Shay Zakov, Yoav Goldberg, Michael Elhadad, and Michal Ziv-ukelson. Journal of Computational Biology. November 2011, 18(11): 1525-1542; (IPKnot): Sato K. et al. Bioinformatics (2011) 27 (13):i85-i93; (ContraFold): Chuong B. Do. et al. Bioinformatics (2006) 22 (14): e90-e98; (MaxExpect): Zhi John Liu et al. RNA (2009), 15:1805-1813; (ProbKnot): Bellaousov S. et al. RNA. 2010 October; 16(10): 1870-80; (Sfold): Ding, Y. et al. Nucleic Acids Res. 32 Web Server issue, W135-W141; (MC-Sym): Parisien M, Major F. Nature 2008, 452(7183):51-55; (NAB): http://casegroup.rutgers.edu/; (Rosetta FARFAR): Kladwang, W., VanLang, C. C., Cordero P., and Das, R. (2011) "A two-dimensional mutate-and-map strategy for non-coding RNA structure", Nature Chemistry 3: 954-962; (NAST): Jonikas M A, Radmer R J, Laederach A, Das R, Pearlman S, Herschlag D, Altman RB. Coarse-grained modeling of large RNA molecules with knowledge-based potentials and structural filters. RNA. 2009 February; 15(2):189-99; and (RNABuilder): Flores S. et al. Transactions in Computational Biology and Bioinformatics 8(5): 1247-57. (2011), the disclosure of all of these reference are incorporated herein by reference in their entireties. (2) identifying one or more structural heterogeneous regions on each of the one or more 2-D or 3-D models of the polynucleotide sequence. (3) calculating one or more chemical shifts from the one or more structural heterogeneous regions. (4) synthesizing a polynucleotide comprising one or more nucleotides having one or more atomic labels positioned at one or more nuclei which results in a polynucleotide having a minimized chemical shift overlap. As used herein, a chemical shift overlap can be computed by comparing the chemical shift values, using metrics such as Hz or ppm, of two or more chemical shift peaks and computing the area or volume that the two or more chemical shift peaks overlap. NMR spectral processing and analysis software can be used to compute the chemical shift overlap; examples of NMR spectral processing and analysis software include VNMRJ, NMRPipe, Sparky, or NMRView. A minimized chemical shift overlap would be measured for those chemical shift peaks that give rise to the smallest aforementioned area or volume. Computational methods, including software for determining a minimized or a maximized chemical shift overlap are illustratively found in the software applications: (VNMRJ): http://www.chem.agilent.com/en-US/products-services/Software-Informatics/VnmrJ-30/Pages/default.aspx; (NMRPipe): F. Delaglio, S. Grzesiek, G. W. Vuister, G. Zhu, J. Pfeifer and A. Bax: NMRPipe: a multidimensional spectral processing system based on UNIX pipes. *J. Biomol. NMR.* 6, 277-293 (1995); (Sparky): T. D. Goddard and D. G. Kneller; (SPARKY 3) University of California, San Francisco; and (NMRView): Johnson, B. A., and Blevins, R. A. (1994), Journal of Biomolecular NMR, 603, the disclosure of all of these software applications are incorporated herein by reference in their entireties.

In an illustrative example, minimized chemical shift overlap (d), where $d=\min(|\delta_i-\delta_j|)$ where $\delta_i, \delta_j \in \{\delta_{labeled\ positions}^{calculated}\}$, can be calculated using a sampling algorithm, such as the Kennard-Stone algorithm (R. W. Kennard, L. A. Stone, Computer aided design of experiments, Technometrics 11 (1969) 137-148) which can be adopted to rank a list of possible combination of labeling positions on each of the polynucleotides in the polynucleotide sample. For example, each labeled position is considered as a point in the Kennard-Stone algorithm. The algorithm works as follows: first find the two positions most dispersed or largest dispersion (d) in the trial set. For each candidate position, find the smallest dispersion (d) to any position already selected. Select that position for the training set which has the largest of these smallest dispersion. This algorithm always gives the same result, due to the two starting positions which are always the same. The results of the Kennard-Stone algorithm would provide the fewest number of necessary polynucleotides needed to be synthesized while maintaining maximum chemical shift dispersion. Other methods to calculate the chemical shift overlap include comparing the chemical shift peak positions and using metrics such as such as root-mean-squared-error, mean-absolute-error, weighted root-mean-squared-error, and weighted mean-absolute-error to compare different chemical shift peaks with the minimized chemical shift overlap being those peaks that give rise to the largest values root-mean-squared-error, mean-absolute-error, weighted root-mean-squared-error, or weighted mean-absolute-error values.

In another embodiment, generation and selection of a structural model step (80) can include the steps:
1. select polynucleotide sequence of interest
2. predict the 2-D structure (2°) using any structure predicting algorithm, for example, mc-fold, mfold or any other 2-D structure predicting algorithm;
3. generate a 3-D model using (2°) structure predicting algorithm: MC-Sym, nab (distance geometry), Rosetta FARFAR, NAST, RNA builder or any other RNA structural prediction approach;
4. determine the minimum energy conformation of the structure using molecular mechanics software: NAB, NAMD, GROMACS, TINKER, CHARMM, AMBER or any molecular modeling software;
5. calculate the regions of the RNA that exhibit large structural variation using metrics such as $S^2$ and/or RMSF, where large structural variation is defined as $S^2<0.8$ and/or RMSF$>0.5$ Å.
6. for regions of the RNA with large structural variations, calculate the chemical shifts from each structure using chemical shift calculation software, for example, Nymirum's Random Forest Predictors (RAMSEY), SHIFTS, NUCHEMICS, and QM methods;
7. Using a computational algorithm(s)/software, such as the Kennard-Stone algorithm, select one or more residues that will be isotopically labeled such that the chemical shift dispersion is maximized, or is as maximized as possible, and the number of samples is minimized.

With reference to FIG. 2, in some embodiments, the first step of the method comprises selecting a polynucleotide for further study. As used herein, information regarding a polynucleotide structure can be used to determine the 2-D & 3-D atomic resolution structure of a polynucleotide of interest, assess heterogeneity of sequence and whether it folds into one or multiple structural forms; structurally map out RNA/DNA-protein and RNA/DNA-ligand interactions; measure the binding affinities/specificities between the RNA/DNA and protein, ligand and other molecules; assign NMR resonances; screen a library of small molecules, biological, or other compounds for binding to the RNA/DNA polynucleotide in question; evaluate the similarities in the 2-D and 3-D structure of different nucleotide sequences; evaluate the presence and/or absence of specific tertiary interactions; evaluate presence and/or absence of specific elements of secondary and 3-D atomic resolution structure; evaluate how changes in physiological conditions such as temperature, pH and salt affect RNA/DNA structure; evaluate protonation/tautomer state of base-pairs; and evaluate structure of excited states (such as transient Hoogsteen base-pairs), among others.

Polynucleotide sequences of interest can be identified by performing a search of nucleotide sequence databases such as EMBL, Genbank, Ensembl, and others known to those of skill in the art which have identified polynucleotide sequences that can be manually searched.

In some embodiments, the next step in the generation of selectively labeled polynucleotides comprises step (20), synthesizing a selectively labeled polynucleotide.

In one embodiment, the polynucleotide is synthesized by synthesizing the polynucleotide with one residue individually labeled with uniform $^{13}C$ and/or $^{15}N$. In this embodiment, for a polynucleotide sequence having N-mer there will be N samples each containing a different nucleotide that is $^{13}C$ and/or $^{15}N$ enriched. In some embodiments, the polynucleotide can be synthesized by creating a polynucleotide having labeled an A and/or U selectively labeled with $^{13}C$ and/or $^{15}N$, or a G and/or C labeled with $^{13}C$ and/or $^{15}N$. In this embodiment, for a polynucleotide sequence having N-mer, the N-mer polynucleotide contains two labeled residues at a time such that each sample will contain an A and U (or T)A and C that is $^{13}C$ and/or $^{15}N$ enriched or a G and C or G and T or G and U that is $^{13}C$ and/or $^{15}N$ enriched, that is, one purine (A or G) and one pyrimidine (C or U or T) can be labeled as a pair. This method utilizes the well-separated chemical shifts of $^{1}H$, $^{13}C$, and $^{15}N$ nuclei in nucleic acid bases ($^{1}H=\sim1.6$, $^{13}C=\sim14$ for T; $^{1}H=\sim7.6$, $^{13}C=\sim153$ for A; $^{1}H=\sim12$, $^{15}N=\sim147$ for G; $^{1}H=\sim13$, $^{15}N=\sim160$ for U or T; $^{1}H=\sim5.5$, $^{13}C=\sim97$ for C; $^{1}H=\sim5.5$, $^{13}C=\sim103$ for U; units in ppm). For the case of $^{1}H$ chemical shift overlap, $^{13}C$ or $^{15}N$ chemical shifts can resolve the residue types by using a shortened version of 2D heteronuclear NMR spectra. Only 2 to 4 complex data points in the $^{13}C$ or $^{15}N$ dimension are sufficient to distinguish if the $^{13}C$ or $^{15}N$ chemical shift is higher or lower frequency than the center.

In another embodiment, the polynucleotide is synthesized and specifically labeled nucleotides are differentially added. In one example, for a given N-mer polynucleotide, multiple sites are $^{13}C$ and/or $^{15}N$ enriched. The final effective concentration for each residue that is $^{13}C$ and/or $^{15}N$ enriched will be varied according to a pre-determined mathematical function that can be dictated at the synthesis step by the inclusion of mixture of a $^{13}C$ and/or $^{15}N$ enriched phosphoramidite and a unlabeled phosphoramidite. This will afford assignment of a given residue according to the NMR resonance area/volume which will be directly proportional to the effective concentration of each $^{13}C$ and/or $^{15}N$ enriched residue.

For example, in a given Nmer-polynucleotide, there are two Gs in the polynucleotide sequence. In order to label both Gs, one G can be labeled with 100% $^{13}C$ and/or $^{15}N$ effective concentration and the second with 50% $^{13}C$ and/or $^{15}N$ effective concentration. Then, both G nucleotides labeled with $^{13}C$ and/or $^{15}N$ can be assigned at the same time according to the area/volume of the resonance. This could also be accomplished with multiple labels with varying effective concentrations following numerical pattern (e.g. residue 1 at 100%, residue 2 at 90%, residue 3 at 80% etc.).

In another example, selective labeling of a polynucleotide can be accomplished by modulating or altering the effective concentration of $^{13}C$ and/or $^{15}N$ enrichment at a given nucleotide so to that it varies according to a mathematical function such as Cos(w t) (where t is the different samples and w is some chosen frequency). In this approach, an NMR interrogated polynucleotide using an NMR device of the present invention can encode the resonance assignments according to the effective incorporation concentration and thus by applying a Fourier transform to the NMR signal, the analysis can provide a 2-D spectrum in which the first dimension provides chemical shift data and the second dimension provides the variation in concentration.

In another example, selective labeling of a polynucleotide sequence can include a 2-D structure based approach): Based on primary sequence, the selective labeling requires that the 2-D structure of the polynucleotide is predicted. Then the polynucleotide sequences of the top 10 or so 2-D structure predictions are aligned and then determine the sites that exhibit the greatest variance in 2-D structure. To selectively label the polynucleotide, the nucleotides that exhibit largest 2-D structural heterogeneity are labeled with an isotope for example, $^{2}H$, $^{13}C$, $^{15}N$, $^{19}F$ or $^{31}P$.

In another example, selective labeling of a polynucleotide can be accomplished by a 3-D atomic resolution structure based approach. In this embodiment, a 3-D atomic resolution structure prediction method can be used to generate a putative model of target RNA. For each residue or nucleotide, calculate the structural heterogeneity over the low energy models. To selectively label the polynucleotide, the nucleotides that exhibit largest structural heterogeneity are labeled with an isotope for example, $^{2}H$, $^{13}C$, $^{15}N$, $^{19}F$ or $^{31}P$.

In various embodiments, the present methods also include a synthesis step (30) for preparing isotopically selectively labeled polynucleotides for study using low field NMR. Step (30) can be for synthesizing target polynucleotides that contain one or more phosphoramidites labeled with one or more of $^{2}H$, $^{13}C$, $^{15}N$, $^{19}F$, or $^{31}P$ are known in the art. Generally, chemical methods for synthesizing polynucleotides using labeled or unlabeled phosphoramidites are relatively well known and are commercially available from Dharmacon (Thermo Fisher Scientific, Waltham Mass., USA). In some embodiments, methods for producing RNA oligonucleotides from labeled or unlabeled ribonucleoside phosphoramidites can include TOM-protected RNA phosphoramidite, tert-butyldimethylsilyl (TBDMS/TBS) based synthesis, ACE protecting group synthesis and others known in the art. (For a general reference, please see Scaringe, S. A. and Caruthers, M. H. "5'-O-Silyl Ethers in Conjunction with Acid-labile 2'-O-orthoesters for the Solid Phase Synthesis of RNA, Preparation of 5'-silyl-2'-orthoester ribonucleosides for use in oligoribonucleotide synthesis. Scaringe S A, Kitchen D, Kaiser R J, Marshall W S. Curr Protoc Nucleic Acid Chem. 2004; and Scaringe, S. A., Wincott, F. E. and Caruthers, M. H. "Novel RNA Synthesis Method Using 5'-Silyl-2'-Orthoester Protecting Groups," J. Am. Chem. Soc., 120, 11820-11821 (1998).).) These sets of protecting groups can then be used with standard phosphoramidite solid-phase synthesis technology ((a) Matteucci, M. D. and Caruthers, M. H. J; Xm. Chem. Soc. 103, 3185-3191 (1981). (b) Beaucage, S. L. and Caruthers, M. H. Tetrahedron Lett. 22, 1859-1862 (1981)) and Chattopadhyaya, J. et al., (1993), "*Deuteration of sugar protons simplify NMR assignments and structure determination of large oligonucleotide by the 1H-NMR window approach.*" Nucleic Acids Research, 21:5005-5011.) All of the above references and their disclosures are incorporated by reference herein in their entireties. Methods for purifying isolated and synthesized polynucleotides are known in the art, for example, purified labeled and unlabeled polynucleotides can be purified using HPLC, gel chromatography, polyacrylamide gel electrophoresis (PAGE), size-exclusion gel chromatography, and ion-exchange chromatography. In some embodiments, preferred methods of purifying RNA polynucleotides include non-polyacrylamide gel electrophoresis methods, for example, HPLC, affinity chromatography, size-exclusion gel chromatography and ion-exchange chromatography.

In various embodiments, methods for synthesizing an isotopically labeled ribonucleoside may generally follow one of three general approaches. The three approaches generally include biomass, enzymatic, and chemical synthesis of isotopically labeled nucleosides. Any of these methods can be employed in the synthesis of the presently described selectively labeled polynucleotides. The biomass method has been developed by Williamson et al., (for example: Batey, R. T., et al., "Preparation of Isotopically Enriched RNAs for Heteronuclear NMR", (1995), Methods in Enzymology, 261:13-32, and Batey, R. T., et al., "Preparation of isotopically labeled ribonucleotides for multidimensional NMR spectroscopy of RNA" (1992), Nucleic Acids Research, 20(17):4515-4523, which disclosures are incorporated herein by reference in their entireties).) The biomass method provides labeled ribonucleoside synthesis and purification using $^{13}$C-glucose, $^{13}$C methanol, $^{15}$N-ammonium sulfate, and $^{13}$C acetate substrates among others that are known, for isotopically labeled nucleoside production in different bacteria types.

In another embodiment, methods useful in the synthesis of labeled RNA nucleotides include those that involve an enzymatic reaction, for example, the enzymatic methods described in Summers, M. F., et al., "*Isotope labeling strategies for NMR studies of RNA*", (2010), Journal of Biomolecular NMR, 46:113-125; Schultheisz, H. L. et al., "*Pathway Engineered Enzymatic de Novo Purine Nucleotide Synthesis*", (2008), ACS Chemical Biology, 3(8):499-511, and Wijmenga, et al., "*Preparation of partially 2H/13C-labelled RNA for NMR studies. Stereo-specific deuteration of the H5*" in nucleotides: (2002), Nucleic Acid Research, 30(7):1639-1645. These references are incorporated herein by reference in their entireties.

In another embodiment, synthetic RNA or DNA nucleosides having a label selected from $^2$H, $^{13}$C, $^{15}$N, $^{19}$F, or $^{31}$P can be synthesized using conventional nucleoside analog phosphoramidite chemistry. Methods for synthesizing RNA phosphoramidites chemically using solid-phase and modified syntheses are described in Höbartner, Claudia and Wachowius, Falk, "Chemical Synthesis of Modified RNA, In "The Chemical Biology of Nucleic Acids, Ed. Mayer, G. (2010) published John Wiley & Sons, Ltd. The cited references disclosing methods for synthesizing labeled RNA ribonucleosides and ribonucleotides are incorporated herein by reference in their entireties. Commercially available RNA phosphoramidites incorporating a labeled $^2$H, $^{13}$C, $^{15}$N, $^{19}$F, or $^{31}$P nuclide can be obtained from Glen Research, SAFC, and others.

2. Acquisition of Chemical Shift for Determination of Polynucleotide Structure Using NMR In some embodiments, the method provides for the NMR interrogation of a target or polynucleotide of interest. In some embodiments, once the polynucleotide of interest is selectively labeled with one or more nucleotides, the polynucleotide is interrogated using low field NMR.

In some embodiments, the present invention provides a method for determining the 2-D or 3-D atomic resolution structure of a polynucleotide, the method comprising:
  (a) providing a polynucleotide sample comprising a polynucleotide, the polynucleotide comprising at least one nucleotide isotopically labeled with one or more atomic labels selected from the group consisting of $^2$H, $^{13}$C, $^{15}$N, $^{19}$F and $^{31}$P;
  (b) obtaining a NMR spectrum of the polynucleotide sample using a NMR device;
  (c) determining a chemical shift of the one or more atomic labels; and
  (d) determining a 2-D or a 3-D atomic resolution structure of the polynucleotide from the chemical shifts determined in step (c).

In some embodiments, the method to determine the 2-D or 3-D structure of a polynucleotide requires interrogation of multiple polynucleotides having the same nucleotide sequence, but differing from each other in that each polynucleotide is isotopically labeled on a different nucleotide. In other words, the method determines the chemical shifts of multiple polynucleotides, each polynucleotide having the identical nucleotide sequence as the first polynucleotide analyzed, and each polynucleotide is synthesized with a different nucleotide labeled with the one or more atomic labels. For example, if the polynucleotide has 5 nucleotides, the method would require 5 polynucleotide samples, each polynucleotide labeled with the one or more atomic labels on a different nucleotide. In this same 5 mer polynucleotide example, the method may utilize a smaller number of distinct polynucleotides that the number of nucleotides present in the nucleotide sequence, by strategically labeling one or more nucleotides in the polynucleotide with one or more atomic labels as described herein. In some embodiments, the polynucleotide sample has only one polynucleotide with one nucleotide labeling pattern. In other embodiments, the polynucleotide sample may contain two or more polynucleotides, each having a different nucleotide labeled with one or more atomic labels. For example, in a 5 mer that has the sequence AUUGC, the polynucleotide sample can include the polynucleotide sequence AUUGC with the first U at position 2 labeled with $^{13}$C. The method proceeds to determine the chemical shift of the isotopically labeled U. A different polynucleotide sample also having the polynucleotide sequence AUUGC with the G at position 4 being labeled with $^{15}$N. This is a different polynucleotide sample as compared to the first example. In a third example, the polynucleotide sample can contain a polynucleotide with the polynucleotide sequence AUUGC wherein the A nucleotide residue is labeled with $^1$H and the C nucleotide residue is labeled with $^{13}$C. In a fourth example, the polynucleotide sample can contain a polynucleotide with the polynucleotide sequence AUUGC wherein the G is isotopically labeled with $^{15}$N and $^{13}$C. In each instance, the method to determine the 2-D or 3-D structure of a biomolecule, for example a polynucleotide, requires one or more polynucleotide samples, each of the one or more polynucleotide samples containing a polynucleotide with the same nucleotide sequence and wherein one or more nucleotides of the polynucleotide are selectively labeled with one or more atomic labels. The determination of 2-D or 3-D atomic resolution structure of a polynucleotide can utilize the chemical shift data from the first example, or the chemical shift data from any combination of examples illustrated above, i.e. one polynucleotide sample or a plurality of polynucleotide samples.

In some embodiments, one or more of the polynucleotide samples contain an internal reference to aid in the identification of the labeled nuclei within the polynucleotide structure. In some embodiments, each polynucleotide in the polynucleotide sample is labeled at the same nucleotide with the same one or more isotopic labels comprising $^2$H, $^{13}$C, $^{15}$N, $^{19}$F or $^{31}$P for internal referencing. In an example, purely for the purpose of illustration, the 2-D or 3-D structure of a 5mer synthesized with the nucleotide AUUGC can be obtained by using internal references. In an illustrative example, the method can employ the use of two polynucleotide samples (both having the same nucleotide sequence AUUGC), one with A1 labeled with $^{13}$C and one with U2 labeled with $^{13}$C. In order to internal reference we can select to label C4 of G4 with $^{13}$C. This means in the first polynucleotide sample we would have A1 labeled with $^{13}$C and C4 of G4 labeled with $^{13}$C, and in the second sample we would have U2 labeled with $^{13}$C and C4 of G4 labeled with $^{13}$C. In this example C4 of G4 labeled with $^{13}$C would serve as the internal reference.

The method can utilize an NMR data acquisition wherein the biomolecule sample(s) (e.g. polynucleotide sample) are examined using an NMR device operable to provide a spectrometer frequency ranging from 20 MHz to about 900 MHz or any commercially available NMR device suitable for the analysis of biomolecules.

In some embodiments, the methods of the present invention also utilize a low field NMR. These methods illustratively include interrogation of the target or selected polynucleotide selectively labeled with one or more nucleotides using a static magnetic field and reference frequency of 300 MHz or less, or about 299 MHz or less, or about 250 MHz or less, or about 225 MHz or less, or about 200 MHz or less, or less than about 175 MHz, or less than about 150 MHz, or less than about 125 MHz, or less than about 100 MHz, preferably, ranging from about 20 MHz to about 300 MHz, or from about 20 MHz to about 299 MHz, or from about 50 MHz to about 275 MHz, or from about 75 MHz to about 250 MHz, or from about 75 MHz to about 225 MHz, or from about 75 MHz to about 200 MHz, or from about 75 MHz to about 175 MHz, or from about 100 MHz to about 300 MHz, or from about 125 MHz to about 275 MHz, or from about 20 MHz to about 250 MHz, or from about 20 MHz to about 225 MHz, or from about 20 MHz to about 200 MHz, or from about 20 MHz to about 150 MHz, or from about 20 MHz to about 100 MHz. Once the polynucleotide has been synthesized it will generally be placed in a cartridge in a lyophilized form. The cartridge may comprise a solid substrate in which the target polynucleotide is deposited. In some embodiments, the cartridge may also contain one or more channels, wells or microfluidic devices operable to store one or more polynucleotide samples. The cartridge can be shaped so that it can be inserted or connected with the sample handling device of the present NMR device described above. In some embodiments, the cartridge also comprises an opening in which one or more fluid handling components in the sample handling device can access and retrieve the stored one or more polynucleotides disposed in the cartridge. In some embodiments, step (40) may also include removing the target or selected one or more polynucleotides simultaneously or sequentially from the cartridge and into the sample handling device for further processing after resuspending the selected one or more polynucleotides with an appropriate solvent or solubulization liquid.

Step (50) of the exemplary method of FIG. 2 provides a step in which the user selects the chemical environment for the one or more polynucleotides to be interrogated using NMR. As used herein, the term "chemical environment" refers to the chemical composition of the solution in which the one or more polynucleotides will be analyzed with NMR in the analysis volume of the sample conduit. The chemical environment may include one or more solutions including, $H_2O$, $D_2O$, a salt, a buffer, a solubilizing agent, an analyte, a pH modifying agent, a screening candidate compound, a biomolecule, (for example, a DNA, RNA protein, polypeptide, lipid molecule or complex) or combinations thereof. In some embodiments, the buffer can include: Bis, Tris, Phosphate, HEPES, MOPS etc. In some embodiments, certain buffers useful in the present methods may or may not be uniformly deuterated so as to eliminate their signals from detection using $^1$H NMR experiments. In some embodiments, representative examples of salts can include: NaCl, $MgCl_2$, KCl, $MnCl_2$ etc.

In an illustrative embodiment, a first selectively labeled polynucleotide may be mixed with a first buffer in the sample device mixing chamber, and then delivered to the sample conduit to fill the analysis volume and interrogated by NMR. A second sample can be prepared using the first selectively labeled polynucleotide and first buffer but then further admixed with a potential RNA binding protein. The second sample is delivered to the sample conduit to fill the analysis volume and interrogated by NMR. In this example, the chemical environment of the same polynucleotide was altered by adding an additional agent that may affect the 3-D structure of the target polynucleotide.

In addition, the methods of the present invention can be used to determine whether binding between a protein and a polynucleotide has occurred, or determine the region of the polynucleotide involved in binding a particular agonist or antagonist agent. In other embodiments, the chemical environment can be selected such that a perturbation agent may be added to the target polynucleotide to study the 3-D atomic resolution structure of the polynucleotide in the presence of such perturbation agents. Note that this can be done in a titration manner according to any proportion of analyte: polynucleotide. In this case multiple chemical shifts for each resonance, each having a different chemical environment of analyte, can be recorded and used to determine parameters such as binding site, $K_d$, kinetics. A chemical shift that changes position or intensity/area/volume on addition of analyte may be indicative of a structural change at that site and/or interaction with the analyte, thus focusing on the nucleotides that have a changing chemical shift on addition of analyte, will allow one to determine the binding site, $K_d$, kinetics etc.

Without wishing to be limited to any one particular theory, it is believed that chemical shift positions can be input into functions such as the equation below for regression analysis in order to determine the $K_d$ in which AT and BT are total concentration (bound+free) of substrates A and B, respectively. Other equations can be used for determination of rate constants and other binding mechanisms.

$$AB = \frac{(A_T + B_T + K_D) - \sqrt{(A_T + B_T + K_D)^2 - 4(A_T B_T)}}{2}$$

In some embodiments, the sample containing the polynucleotide of interest which may be single stranded or double stranded may be heated to a temperature of about 95° C. for 5 minutes, and then gradually reduce the heat until the polynucleotide has reached room temperature to anneal the polynucleotide prior to NMR interrogation using an NMR device as described herein.

Step (60) of FIG. 2 provides the next step in the exemplified methods described herein. In step (60), in some embodiments, the method further includes interrogation of the selectively labeled polynucleotide using low field NMR. The interrogation of the selectively labeled polynucleotide can include structural determination of the 2D & 3-D structure of a polynucleotide of interest, assess heterogeneity of sequence and whether it folds into one or multiple structural forms; structurally map out RNA/DNA-protein and RNA/DNA-ligand interactions; measure the binding affinities/specificities between the RNA/DNA and protein, ligand and other molecules; assign NMR resonances; screen a library of small molecules, biological, or other compounds for binding to the RNA/DNA; evaluate the similarities in the 2-D and 3-D structure of different nucleotide sequences; evaluate presence/absence of specific tertiary interactions; evaluate presence/absence of specific elements of secondary and 3-D atomic resolution structure; evaluate how changes in physiological conditions such as temperature and pH affect RNA/DNA structure; evaluate protonation/tautomer state of base-pairs; and evaluate structure of excited states (such as transient Hoogsteen base-pairs).

In some embodiments, the NMR interrogation step (60) of the described methods can include 6 general steps. Although not all of the steps are required, or are performed in the order below, it is preferred to have all six steps performed prior to and during an interrogation of a biomolecule containing sample using NMR.

First, NMR interrogation step (60) can include a temperature regulation step. In this aspect, the liquid sample containing the polynucleotide of interest in the appropriate chemical environment is transferred to a sample conduit and fills the analysis volume with sample for NMR interrogation. Second, the sample in the sample conduit can be equilibrated at a selected temperature ranging from 0 to 60° C. Third, a tuning and matching step can be performed. This process adjusts the resonant circuit frequency and impedance until they coincide with the frequency of the pulses transmitted to the circuit and impedance of the transmission line (typically 50 ohm). For best signal-to-noise and minimal RF coil heating, the tuning and matching should be done for each sample. But with pre-adjustment during manufacturing process, minor or no adjustment is necessary for low field magnets. Fourth, a locking step is performed. In this process, the 2H signal is found from deuterated solvent for internal feedback mechanism by which magnetic field drift can be compensated. The $^2$H signal (for example, 30.7 MHz at 200 MHz spectrometer) being distant from $^1$H signal is acquired and processed independently. Lock signal also serves as chemical shift reference. Fifth, prior to acquiring NMR data on the sample being interrogated is a shimming step. In some embodiments, the interrogation step may require creating a homogeneous magnetic field at the analysis volume by controlling electric currents in a set of coils which generate small static magnetic fields of different geometries and strength and correct inhomogeneity of the $B_0$. For NMR interrogation of biomolecules of the present invention, it is preferred to have at least 50 ppb (part per billion) of field homogeneity when analyzing samples using NMR. Sixth, a sequence of precise pulses and delays are applied to $^1$H and $^{13}$C transmission lines connected to each resonant circuit around the analysis volume to manipulate spin quantum states of nuclei in the sample. As a result, only the desired signals such as $^1$H nuclei spins attached to $^{13}$C are selected and measured excluding all other $^1$H nuclei spins attached to other nuclei, or using shaped pulses (selective pulses) nuclei having certain chemical shift range are detected. Many different types of pulse sequences can be applicable for different purposes including a variety of HSQC, HMQC, COSY, TOCSY, NOESY, ROESY for structural determinations of biomolecules in 1-D, 2-D, and 3-D experimental settings. In some embodiments, after the pulse sequence, the same resonant circuits (including the 2 or more RF coils) are sensing fluctuation of magnetic field around analysis volume (called FID; free induction decay) as electric voltage which is digitized and recorded for predefined duration. To improve the signal-to-noise (S/N), a set of pulsing and recording steps are repeated multiple times and added with some delay in between, called relaxation delay which allow spin systems to return to initial state before starting pulsing.

3. NMR Signal Processing

As shown in FIG. 2, once the polynucleotide in the analysis volume has been interrogated using NMR, the signals emitted from the target nuclei are converted from an analog signal and converted to a digital signal. The next step in determining the chemical shifts of the various nuclei in the polynucleotide sample required for structure determination step (70) involves processing the NMR signals for determination of the chemical shifts of the various nuclei. The first step in such a determination comprises a Fourier transformation step. The acquired FID (free induction decay) in IUPAC JCAMP-DX or other proprietary format is read and converted to an internal data format. Standard processing techniques such as zero-filling, apodization (or window functions), and baseline correction applied along with Fourier transformation and phase correction for balancing between sensitivity and resolution can be employed. The next step can include a peak picking step. In this step, the Fourier transformed spectrum is analyzed to detect position (in Hz and ppm unit) and intensity (or height)/area under a peak/volume enclosing a peak (in 2-D and 3-D) (in arbitrary unit) of peaks using the fitness of spectral shape to 2-D or 3-D Gaussian, Lorentzian, or other shapes, which generates a list of peak positions and intensities (or heights), areas under peaks, and volume within enclosed peaks. Next, the NMR signal processing step (70) includes a chemical shift referencing step. In this step, the chemical shift of DSS (4,4-dimethyl-4-silapentane-1-sulfonic acid) or TSP (trimethylsilyl propionate) or other compounds at 0 ppm is used as reference for chemical shifts of other atoms. Using information of sample and internal reference concentration and $^2$H lock frequency, internal reference peak at around 0 ppm can be identified from the peak list and set as 0 ppm for reference purpose. In some embodiments, chemical shift assignments can also be facilitated through the use of two software programs SHIFTS and NUCHEMICS.

Next, with reference to FIG. 2, the methods of the present invention also provide a step involving the generation and selection of a structural model of the polynucleotide based on the chemical shift data and other NMR constraints obtained during the NMR interrogation step. In some embodiments, step (80) can employ any of the methods provided below for the determination of 3-D and 4-D atomic resolution structure using the chemical shift and other NMR interactions obtained during the NMR interrogation step.

In one embodiment, the user can generate using some conformational sampling method many candidate models for a nucleic acid of interest. For each model, the user can back-predict NMR data e.g. chemical shifts, NOE, J-coupling and RDC, collectively referred to as the theoretical NMR data. The user can then select the model or select number of models that best agree with experimental NMR data as the solved structure of the nucleic acid.

In another embodiment, the user can reference the experimental NMR data e.g. chemical shifts, NOE, J-coupling and RDC to generate structure restraints that can be incorporated into molecular dynamics (MD) simulations to generate a plurality of conformers or ensembles. The restraint MD simulation sample ensembles that best satisfy the experimentally derived restraints are then collected Finally, the ensemble or conformer generated during the MD simulation that best agrees with experimental NMR data is selected as the solved structure of the polynucleotide. In some embodiments, ensembles can be constructed using chemical shifts data using the sample and select (SAS) approach as described previously in U.S. patent application Ser. No. 13/120,064, published as U.S. Patent Application Publication No. 2011/0172981, the disclosure of which is incorporated herein by reference in its entirety. The ensembles can be selected by the use of a minimizing cost function, for example, using Monte Carlo procedures (see below), the cost function expressed in the following equation:

$$\chi_{CS}^2 = \frac{1}{L_{CS}} \sum_{i=1}^{N} \left( \delta_i^{pred} - \delta_i^{meas} \right)^2$$

Here $\delta_i^{pred}$ and $\delta_i^{meas}$ are the predicted and measured chemical shifts for the $i^{th}$ proton, respectively, and $L_{CS}$ is the total number of chemical shift, respectively. Each selection cycle is initiated from N randomly selected conformers. A Monte Carlo (MC) simulated annealing scheme is then used to minimize Eq. (2). Simulations were initiated at a high "temperature" (a parametric, effective temperature), where the MC acceptance probability was high (0.99), and slowly decreased until the MC acceptance probability was $10^{-5}$. At a given effective temperature $10^5$ MC steps were carried out. The effective temperature was then decreased according to the exponential schedule $T_{(n+1)} = 0.92\ T_n$. This selection is repeated e.g. 10-1000 times, generating in the range 10*N to 1000*N conformers that pool together used a representative dynamical ensemble.

In another embodiment, generation and selection of a structural model step (80) can include the steps:
1. predict 2-D structure using any structure predicting algorithm, for example, contrafold, Vienna RNA package, centroid-fold, RNAstructure, ContextFold, IPKnot, MC-Fold, MFold, and the like;
2. generate a 3-D model using 3-D structure predicting algorithm, for example, MC-Sym, NAB (distance geometry), Rosetta FARFAR, NAST, RNA builder, and the like;
3. determine the minimum energy conformation of the structure using molecular mechanics software, for example, NAB, NAMD, GROMACS, TINKER, CHARMM, AMBER, and the like;
4. back-calculate the chemical shifts from each model using chemical shift calculation software, for example, Nymirum's Random Forest Predictors (RAMSEY), SHIFTS, NUCHEMICS, and QM methods;
5. compare experimental and predicted chemical shifts for each model; and
6. select the model that exhibits the best agreement between experimental and predicted chemical shifts.

In some embodiments, the present invention provides a method for determining the 2-D or 3-D atomic resolution structure of a polynucleotide. In some examples, the method comprises: providing a polynucleotide sample comprising a plurality of polynucleotides, the plurality of polynucleotides having an identical nucleotide sequence, wherein each polynucleotide comprises at least one nucleotide isotopically labeled with one or more atomic labels selected from the group consisting of $^2H$, $^{13}C$, $^{15}N$, $^{19}F$ and $^{31}P$; obtaining a NMR spectrum of the polynucleotide sample using a NMR device; determining a chemical shift of the one or more atomic labels; and determining a 2-D or a 3-D atomic resolution structure of the polynucleotides from the chemical shifts determined in step (c).

In another embodiment, the present invention provides a method for determining the 3-D atomic resolution structure of a polynucleotide, once the polynucleotide in the analysis volume has been interrogated using NMR. In one embodiment, the signals emitted from the isotopically labeled nuclei are converted from an analog signal and converted to a digital signal. The next step in determining the chemical shifts of the various atomically labeled nuclei in the polynucleotide sample required for structure determination involves processing the NMR signals for determination of the chemical shifts of the various nuclei or the experimental chemical shifts. The method then proceeds by:
(a) generating a plurality of theoretical structural polynucleotide 2-D models using the nucleotide sequence and one or more 2-D structure predicting algorithms;
(b) generating a plurality of theoretical structural polynucleotide 3-D models using a 3-D structure predicting algorithm using the plurality of theoretical structural polynucleotide 2-D models;
(c) generating a predicted chemical shift set for each of the plurality of theoretical structural polynucleotide 3-D models;
(d) comparing the predicted chemical shift set to the chemical shift(s) of the one or more atomic labels; and
(e) selecting a theoretical structural polynucleotide 3-D model having the closest agreement between the respective predicted chemical shift set and the chemical shift(s) of the one or more atomic labels as the 3-D atomic resolution structure.

As used herein, an illustrative 2-D structure prediction algorithm is defined as an algorithm(s) employed in software such as: MC-Fold, MC-Fold-DP, Mfold, CentroidFold, ContextFold, IPKnot, ContraFold, MaxExpect, ProbKnot, Sfold, or any other polynucleotide secondary structure prediction approach. Exemplary software applications capable of 2-D structure prediction can include: (MC-Fold): Parisien M, Major F. Nature 2008, 452(7183):51-55; (MC-Fold-DP): Höner zu Siederdissen, Christian, Stephan H. Bernhart, Peter F. Stadler, and Ivo L. Hofacker. 2011. Bioinformatics 27: 129-36. Mfold: M. Zuker & A. B. Jacobson. RNA 4, 669-679, 1998; (CentroidFold): Sato K. et al. Nucleic Acids Research, 2009, Vol. 37, Web Server issue; (ContextFold): Shay Zakov, Yoav Goldberg, Michael Elhadad, and Michal Ziv-ukelson. Journal of Computational Biology. November 2011, 18(11): 1525-1542; (IPKnot): Sato K. et al. Bioinformatics (2011) 27 (13):i85-i93; (ContraFold): Chuong B. Do. et al. Bioinformatics (2006) 22 (14): e90-e98; (MaxExpect): Zhi John Liu et al. RNA (2009), 15:1805-1813; (ProbKnot): Bellaousov S. et al. RNA. 2010 October; 16(10): 1870-80; (Sfold): Ding, Y. et al. Nucleic Acids Res. 32 Web Server issue, W135-W141, each of these software applications and their use are incorporated herein by reference in their entirety.

As used herein, generating a predicted chemical shift set for each of the plurality of theoretical structural polynucleotide 3-D models, includes determination of a chemical shift set wherein, the algorithms present in the software, such as, Nymirum's Random Forest Predictors (RAMSEY), SHIFTS, NUCHEMICS, or quantum mechanics methodologies, all of which generally take as input the 3-D atomic coordinates of one or more theoretical polynucleotide 3-D models and output predicted chemical shifts for one or more atoms in the theoretical polynucleotide 3-D models. Such software and algorithms are provided in: (RAMSEY): Prediction of RNA 1H and 13C Chemical Shifts—A Structure Based Approach. Frank A T. Bae S H, Stelzer A C. J. Phys. Chem. B. 2013 September; (SHIFTS): http://casegroup.rutgers.edu/qshifts/qshifts html; (NUCHEMICS): Cromsigt J A, Hilbers C W, & Wijmenga S S (2001) Prediction of proton chemical shifts in RNA. Their use in structure refinement and validation. J Biomol NMR 21(1):11-29; and generally, as provided in "Quantum mechanics based": Fonville T M. et al. Chemistry. 2012 Sep. 24; 18(39):12372-87, the disclosures and use of the software and methods implementing their use is hereby incorporated herein by reference in their entirety.

In some of the above embodiments, generating the predicted chemical shift set comprises: calculating a polynucleotide structural metric comprising atomic coordinates, stacking interactions, magnetic susceptibility, electromagnetic fields, or dihedral angles from one or more experimentally determined polynucleotide 3-D structures; generating a set of mathematical functions or objects that describe relationships between experimental chemical shifts and the polynucleotide structural metric of the experimentally determined 3-D polynucleotide structures using a regression algorithm; calculating a polynucleotide structural metric for each of the theoretical structural polynucleotide 3-D models; inputting the polynucleotide structural metric for each of the theoretical structural polynucleotide 3-D models into the set of mathematical functions or objects to generate the predicted chemical shift set.

As used above, a polynucleotide structural metric can include a structure data comparator representing any one or more of: atomic coordinates, stacking interactions, magnetic susceptibility, electromagnetic fields, or dihedral angles from one or more experimentally determined polynucleotide 3-D structures. In some embodiments, a predicted chemical shift set is generated by comparing each theoretical structural polynucleotide 3-D model with a NMR-data polynucleotide structure database. A NMR-data polynucleotide structure database is a database that relates NMR data such as chemical shifts, residual dipolar couplings, scalar couplings, peak intensities, relaxation rates, NOEs, or any other data measured from NMR spectra to experimentally determined or computationally modeled 2-D or 3-D polynucleotide structures.

In one embodiment, the predicted and experimental chemical shifts can be compared using various metrics such as root-mean-squared-error (RMSE), mean-absolute-error (MAE), weighted root-mean-squared-error (wRMSE), and weighted mean-absolute-error (wMAE):

$$RMSE = \sqrt{\frac{1}{N}\sum_n (\delta_{n,exp} - \delta_{n,pred})^2}$$

$$MAE = \frac{1}{N}\sum_n |\delta_{n,exp} - \delta_{n,pred}|$$

$$wRMSE = \sqrt{\sum_i \sum_j w_i(\delta_{i,j,exp} - \delta_{ij,pred})^2}$$

$$wMAE = \sum_i \sum_j w_i |\delta_{i,j,exp} - \delta_{i,j,pred}|$$

in which $\delta_{exp}$ and $\delta_{pred}$ are experimental and predicted chemical shifts, respectively; i is the index for nuclei types (H1', H2', H3', H4', H5', H5", H2, H5, H6, H8, C1', C2', C3', C4', C5', C2, C5, C6, and C8); j is the index for the subset of chemical shifts data for each nucleus type i; iteration of i and j is equal to total number of chemical shifts, N; $w_i$ is a weight factor that equalize the differential prediction errors for different nuclei types.

The weight factor $w_i$ can be defined in various ways. For example, the weight factor can be defined using the Pearson coefficient R and RMSE:

$$w_i = \frac{R_i^2}{RMSE_i}$$

in which $R_i$ and $RMSE_i$ are the Pearson correlation coefficient and the root-mean-squared-error for the chemical shift prediction of nucleus type i, respectively. Other mathematical forms of weight factor can be used to equalize the differential prediction errors for different nuclei types.

In some embodiments, molecular dynamics simulations can be employed to refine the selected model. In one embodiment of this aspect, the following steps can be employed: 1. use experimental chemical shifts to predict dihedral angles. In some embodiments, the predicted dihedral angles can be determined using random forest, neural network or any other machine learning approach against a chemical shift and structure database; 2. generate dihedral constraints; 3. starting from a model generated using MC-Sym, NAB (distance geometry), Rosetta FARFAR NAST, RNA builder or any other RNA structural prediction approach, carryout restrained MD using dihedral constraints and any other available structure restraints software, for example, NAMD, XPLOR, GROMACS, CHARMM, TINKER. In some embodiments, the restrained MD is carried out in vacuum, followed by extensive simulation in implicit or explicit solvent. 4. extract models from MD trajectory; 5. back-calculate chemical shifts from each model; 6. for each model, compare experimental and predicted chemical shifts; and 7. select the model that exhibits the best agreement between experimental and predicted chemical shifts.

In another aspect of the molecular dynamics simulation approach, a structural model for the 3-D structure of a polynucleotide can be obtained by performing the molecular dynamics simulation de novo. In this aspect, the user: 1. obtains a predicted 2-D structure using mc-fold, infold or any other 2-D structure predicting algorithm; 2. uses 2-D structure to generate base pairing distance constraints; 3 uses the experimental chemical shifts obtained during the NMR interrogation step described above to predict dihedral angles, wherein the predicted models are generated dihedrals angles are generated using random forest, neural network or any other machine learning or regression approach against a chemical shift and structure database; 4. the user then generates dihedral constraints for the polynucleotide; 5. then starting from an ideal extended or random RNA structure, the user performs restrained MD simulations using distance and dihedral constraints and any other available structure restraints obtained during the NMR interrogation; In some embodiments, the restrained MD is carried out in vacuum, followed by extensive simulation in implicit or explicit solvent. 6. the user then extracts one or more models from the calculated MD trajectory; 7. the user then back-calculates the chemical shifts of selected nuclei from each model using chemical shift software, for example: Nymirum's Random Forest Predictors (RAMSEY), SHIFTS, NUCHEMICS, or QM methods; 8. for each model, experimental and predicted chemical shifts are compared; and 9. the user can select the model that exhibits the best agreement between experimental chemical shifts obtained and predicted chemical shifts.

In some embodiments, the last step shown in FIG. 2, a user may optionally validate and output the 3-D structure of the polynucleotide of interest as contained in the specific chemical environment selected. In one embodiment, the validation and outputting step 90 can be performed by using an input model that best agrees with the experimental chemical shifts determined during the experimental NMR interrogation. The user can back-calculate NMR relevant observables, for example, NOEs, J-coupling, RDCs etc. The theoretical model can be used to prepare predicted NMR data, for example, NOEs, J-coupling, RDCs etc. which can then be compared to the experimentally obtained data such as NOEs, J-coupling, RDCs etc. The model selected should exhibit reasonable agreement with experimental NOEs, J-coupling, RDCs etc. The selected model of the 3-D structure of the selective labeled polynucleotide with isotopically nuclei interrogated using low field NMR can then be outputted as a validated structure to the user.

In various aspects of the methods of the present invention, 3-D structures of polynucleotides that are solved using the devices and methods of the present invention can be uploaded into a proprietary network for future use by other users. In this aspect, solved or predicted 3-D structures of biomolecules, for example, polynucleotides, proteins and polypeptides can be cataloged and stored in memory banks for future use by a user having a similar or identical sequence or subsequence to facilitate structure prediction and determination. In addition to the 3-D structure of the submitted biomolecule, experimental and quantified NMR constraints such as chemical shifts, NOEs, J-coupling, RDCs etc can be associated with the submitted structure.

In one embodiment, the present invention provides an NMR system for determining the 3-D atomic resolution structure and dynamics of a polynucleotide. In one embodiment, the system or method employing the NMR device of the present invention comprises for determining a 2-D or 3-D atomic resolution structure of a biomolecule, for example, a polynucleotide, for example, an RNA polynucleotide comprises: providing a low-field NMR device having a spectrometer frequency of 300 MHz or less, the NMR device comprising a housing; a sample handling device operable to receive a sample containing the biomolecule; and a NMR module, wherein the NMR module comprises: a sample conduit comprising an analysis volume operable to receive at least a portion of the sample from the sample handling device; a first tuned coil surrounded by a second tuned coil with the first and the second tuned coil(s) disposed proximately to the analysis volume, wherein each of the first and the second tuned coil(s) being operable to generate a distinct excitation frequency pulse across the analysis volume to generate nuclear magnetic resonance of a plurality of isotopically labeled nuclei of the biomolecule in the analysis volume; and at least one magnet operable to provide a static magnetic field across the analysis volume and the first and said second tuned coil(s); placing an isotopically labeled biomolecule sample in the sample conduit; obtaining a NMR spectra of the biomolecule; determining a chemical shift of the one or more atomic labels; and determining a 2-D or a 3-D atomic resolution structure of the polynucleotides from the chemical shifts determined in step (d).

In some embodiments of the above system or method, obtaining a NMR spectra or spectrum of the biomolecule includes obtaining NMR spectra using a NMR spectrometer frequency of about 20 MHz to about 300 MHz, or from 20 MHz to about 250 MHz, or from 20 MHz to about 200 MHz, or from 20 MHz to about 150 MHz, or from 20 MHz to about 100 MHz, or from 20 MHz to about 75 MHz.

In various embodiments, the NMR device of the present invention for use in the above method may also require placing a biomolecule sample in the sample conduit and optionally heating or cooling the biomolecule in the sample conduit prior to or during obtaining a NMR spectra of the biomolecule. In some embodiments, the 2-D or 3-D atomic resolution structure of the polynucleotide under investigation is first annealed and then subsequently cooled to obtain a thermodynamically favorable structure. The availability of a heating and cooling element in the NMR device may also favorably prevent unwanted molecular movement, base pairing, self-binding and the like.

IN various embodiments of the present methods, obtaining a NMR spectra of the biomolecule further includes applying a pulsed field gradient during acquisition of experimental chemical shift data of the plurality of nuclei of the biomolecule.

In some examples of the present system or methods described herein, an exemplary method for determining the 3-D atomic resolution structure of the biomolecule further comprises: generating a plurality of theoretical structural biomolecule 2-D models using the biomolecule sequence and one or more 2-D structure predicting algorithms; generating a plurality of theoretical structural biomolecule 3-D models using a 3-D structure predicting algorithm using the plurality of theoretical structural biomolecule 2-D models; generating a predicted chemical shift set for each of the plurality of theoretical structural biomolecule 3-D models; comparing the predicted chemical shift set to the chemical shift(s) of the one or more atomic labels; and selecting a theoretical structural biomolecule 3-D model having the closest agreement between the respective predicted chemical shift set and the chemical shift(s) of the one or more atomic labels as the 3-D atomic resolution structure. In some embodiments, chemical shift data of the biomolecule can be gathered at spectrometer frequencies of 300 MHz or less, for example at about 20 MHz to about 100 MHz.

While the methods and systems described herein apply to polypeptides, proteins and polynucleotides, in some embodiments, the methods apply to the analysis of an isotopically labeled polynucleotide, for example, an isotopically labeled ribonucleic acid (RNA). In some of these embodiments, the biomolecule to be analyzed is labeled with one or more isotopic labels comprising: $^2H$, $^{13}C$, $^{15}N$, $^{19}F$ or $^{31}P$.

Specific examples for determining the 2-D or a 3-D atomic resolution structure of a polynucleotide can include the steps: generating a plurality of theoretical structural polynucleotide 2-D models using the polynucleotide sequence and one or more 2-D structure predicting algorithms; generating a plurality of theoretical structural polynucleotide 3-D models using a 3-D structure predicting algorithm using the plurality of theoretical structural polynucleotide 2-D models; generating a predicted chemical shift set for each of the plurality of theoretical structural polynucleotide 3-D models; and comparing the predicted chemical shift set to the chemical shift(s) of the one or more atomic labels; and selecting a theoretical structural polynucleotide 3-D models having the closest agreement between the respective predicted chemical shift set and experimental chemical shifts indicative of the 3-D atomic resolution structure.

In some of these exemplary methods and systems of the present invention, the predicted chemical shift set of the biomolecule, for example a polynucleotide can be generated by comparing each theoretical structural polynucleotide 3-D model with a database comprising a relationship between experimental chemical shifts and experimentally determined 3-D polynucleotide structures. In one related embodiment, generating the predicted chemical shift set can include the steps: calculating a polynucleotide structural metric comprising atomic coordinates, stacking interactions, magnetic susceptibility, electromagnetic fields, or dihedral angles from one or more experimentally determined polynucleotide 3-D structures; using a regression algorithm to generate a set of mathematical functions or objects that describe relationships between experimental chemical shifts and the polynucleotide structural metric of the experimentally determined 3-D polynucleotide structures; calculating a polynucleotide structural metric for each of the theoretical structural polynucleotide 3-D models; inputting the polynucleotide structural metric for each of the theoretical structural polynucleotide 3-D models into the set of mathematical functions or objects to generate the predicted chemical shift set. Several examples of regression algorithms are described herein. In one embodiment, the method uses a Random Forest algorithm.

In one embodiment, an exemplary method routine using a low-field NMR device described herein as shown in FIG. 2 is as follows. In one embodiment, the user wishes to determine the 3-D structure of a 25 nucleotide TAR RNA and to map out its interaction with a protein molecule, the following steps may be performed: 1. Load a cartridge into the device containing a selectively labeled 25 nucleotide TAR RNA using one or more nuclei selected from: $^2$H, $^{13}$C, $^{15}$N, $^{19}$F, or $^{31}$P. 2. Use the user interface with a graphical user interface to select the application of interest. In one example, it is "3-D structure determination". 3. The instrument records NMR spectra of the 25 nucleotide TAR RNA. It will use the device to transport the sample from the sample storage device (e.g. a cartridge) into the NMR module. This may be a microfluidic device or the sample may be in a micro-cartridge that fits into the NMR probe. 4. An NMR spectra is recorded of the sample in an automated manner. This can include 1-D, 2-D, 3-D . . . N-D heteronuclear or homonuclear experiments involving $^1$H, $^{13}$C, $^{15}$N, and $^{31}$P nuclei. 5. The computer executes a peak picking software program from memory, memory module or a program storage medium, wherein the software program is then used to measure the individual proton, carbon, nitrogen and phosphorus chemical shifts for all selectively labeled polynucleotide samples measured or stored in a memory module. 6. RNA structures are predicted based on sequence using existing structure predicting algorithm (such as MC-Sym). 7. The $^1$H, $^{13}$C, $^{15}$N, and $^{31}$P chemical shifts are then predicted for each candidate predicted RNA structures using in-house software. 8. The agreement between the predicted and measured chemical shifts is then used to select a starting seed structure. 9. Optionally, the seed structure is subjected to further refinement rounds using an energy function that includes the difference between measured and computed chemical shifts. 10. Cross validation statistics is then used to rigorously assess the accuracy of the determined structure. 11. The instrument then outputs one or more structures that satisfies the chemical shifts within prediction/measurement error. 12. The analysis module then performs a binding analysis. 13. On the user interface (for example a graphical user interface) user selects application "binding analysis" and selects the selectively labeled polynucleotide sample(s) on which he/she wishes to use to probe binding of the TAR to a protein molecule. 14. Device loads a protein sample into the device mixing chamber. 15. A microfluidic mixing device mixes the selectively labeled polynucleotide sample with the selected protein. 16. New RNA-protein sample is transferred to the NMR probe by the device. 17. The NMR module performs an NMR spectral analysis of the selectively labeled polynucleotide sample(s) containing the protein. 18. The chemical shifts are recorded on the selectively labeled polynucleotide sample(s) containing the protein and stored in the analysis module. 19. The analysis module calculates the difference between the TAR RNA chemical shifts measured in the absence or presence of the selected protein and is highlighted on the 3-D structure of the RNA on the GUI interface.

EXAMPLES

Example 1

Structure Determination of an Apical Loop Sequence of Human pre-miR 122 RNA

The apical loop sequence of human pre-miR 122 RNA sequence was investigated as an example.

Two base pairs at the 5'- and 3'-ends of the sequence were modified from the native pre-miR 122 sequence in order to stabilize the 24-mer stem loop construct for NMR studies (5'-GGCUUGUGUCUAAACUAUCAAGCC-3').

The 2-D structures predicted by the software program MFold suggest the possibility of a long stretch (up to 12 bases) of an apical loop which combined together with redundant adenine bases in the loop sequence prohibits conventional sequential assignment using uniformly non-selectively labeled RNA sample and thus requires selective labeling for unambiguous resonance assignment and 3-D structure determination. Four RNA oligonucleotides sequences are designed for selective labeling. Each has two selectively $^{13}$C/$^{15}$N isotope labeled residues. Labeling a pair of purine (A or G) and pyrimidine (C or U) in a single oligonucleotides reduces the number of samples by half and minimize potential spectral overlap between two labeled residues since two purines or two pyrimidines are more likely to overlap.

```
(i)    5'-GGCUUGUGUCUAAACUAUCAAGCC-3'    (U11/A12)

(ii)   5'-GGCUUGUGUCUAAACUAUCAAGCC-3'    (C10/A13)

(iii)  5'-GGCUUGUGUCUAAACUAUCAAGCC-3'    (A14/C15)

(iv)   5'-GGCUUGUGUCUAAACUAUCAAGCC-3'    (U16/A17)
```

The $^{13}$C/$^{15}$N labeled 2'-ACE® phosphoramidites (rA, rG, rC, rU) for chemical synthesis were prepared by Dharmacon from individual $^{13}$C/$^{15}$N labeled ribonucleosides (Chembridge Isotope Laboratories). Uniformly $^{13}$C/$^{15}$N labeled apical loop construct of the human pre-miR 122 (5'-GGC-UUGUGUCUAAACUAUCAAGCC-3') sequence was prepared by T7 in vitro RNA transcription using $^{13}$C/$^{15}$N labeled rNTPs (Chembridge Isotope Laboratories) and purified by polyacrylamide gel electrophoresis (PAGE). Four selectively $^{13}$C/$^{15}$N isotopes labeled RNA oligonucleotides (U11/A12, C10/A13, A14/C15, and U16A17) were chemically synthesized and PAGE purified by Dharmacon.

Samples of 200 µL volume were contained in a Shigemi NMR tube for NMR experiments.

Samples were dissolved in 200 µL of aqueous buffer of 15 mM phosphate, 25 mM NaCl, 0.1 mM EDTA, 90% $H_2O$/10% $D_2O$. Final RNA concentrations were 0.1-0.3 mM. 10% $D_2O$ was added for locking and 10 µM DSS (4,4-dimethyl-4-silapentane-1-sulfonuc acid) was added as internal chemical shift reference. The $^1$H signal of DSS was referenced to 0 ppm.

All NMR data were collected with a 600 MHz Agilent NMR spectrometer equipped with a HCN-triple resonance/z-gradient PFG probe at 4-30° C.

For the uniformly labeled polynucleotide sample, the assignment of the exchangeable imino proton and nitrogen resonances, 2D $^{15}$N—$^1$H HSQC (sweep width(Hz)=13020(H)×1215(N); complex data points=1024(H)×38(N); carrier frequency=water(H), 154 ppm(N)) and 2D $^1$H—$^1$H NOESY (sweep width (Hz)=13020(H)×13020(H); complex data points=1024×256; carrier frequency=water; NOE mixing time of 200, 300 msec) were acquired at 4° C. and 10° C. For assignment of the non-exchangeable aromatic and ribose proton and carbon resonances, 2D $^{13}$C—$^1$H HSQC(aromatic) (sweep width (Hz)=4808(H)×1734(C); complex data points=385×110; carrier frequency=water(H), 140.5 ppm (C)), 2D $^{13}$C—$^1$H HSQC(ribose) (sweep width (Hz)=4808 (H)×2715(C); complex data points=385×170; carrier frequency=water(H), 98 ppm(C)), 2D HCN(aromatic) (sweep width(Hz)=4808(H)×1823(N); complex data points=385(H)×64(N); carrier frequency=water(H), 140.5 ppm(C), 158 ppm(N)), 2D HCN(ribose) (sweep width(Hz)=4808(H)×1823(N); complex data points=385 (H)×64(N); carrier frequency=water(H), 98 ppm(C), 158 ppm(N)), and 3-D NOESY-13C-HSQC(ribose) (sweep width(Hz)=4807(H)×3000(H)×2413(C); complex data points=385(H)×34(H)×40(C); carrier frequency=water(H), 6 ppm(H), 98 ppm(C); NOE mixing time of 250 and 350 msec), 3-D NOESY-$^{13}$C-HSQC(aromatic) (sweep width (Hz)=4807(H)×3000(H)×1734(C); complex data points=385(H)×46(H)×28(C); carrier frequency=water(H), 6 ppm(H), 140 ppm(C); NOE mixing time of 200, 250 and 350 msec) were acquired at 20° C., 25° C. and 35° C.

For selectively labeled samples, a 2D $^{13}$C—$^1$H HSQC (aromatic) (sweep width (Hz)=4808(H)×3620(C); complex data points=385×64; carrier frequency=water(H), 146 ppm (C)), 2D $^{13}$C-1H HSQC(ribose) (sweep width (Hz)=2404 (H)×3318(C); complex data points=194×60; carrier frequency=water(H), 98 ppm(C)), 2D HCN(aromatic) (sweep width(Hz)=4808(H)×2000(N); complex data points=385(H)×32(N); carrier frequency=water(H), 140.5 ppm(C), 158 ppm(N)), and 2D HCN(ribose) (sweep width (Hz)=4808(H)×2000(N); complex data points=385(H)×32 (N); carrier frequency=water(H), 98 ppm(C), 158 ppm(N)) were acquired at 25° C.

All acquired NMR data were converted and processed by NMRPipe software available at (http://spin.niddk.nih.gov/NMRPipe/). Briefly, for each dimension, the converted FID was apodized by shifted cosine or Gaussian, zero-filled to double the size of acquired data points, Fourier transformed and phase corrected, and baseline adjusted. Processed 2-D and 3-D spectra were analyzed by Sparky software application version 3.113 available at (http://www.cgl.ucsf.edu/home/sparky/). Center of peak position (chemical shift) and volume of peak were obtained by numerical fitting of the processed peak shape to an analytical Gaussian function.

Chemical shift-Structure Database. A chemical shift-structure relation database was populated with experimental data of three dimensional atomic coordinates and chemical shifts taken from 18 RNA systems deposited in both PDB (Protein Data Bank; http://www.rcsb.org) and BMRB (Biological Magnetic Resonance Bank; http://www.bmrb.wisc.edu) (1LDZ(4226), 1YSV(6485), 1R7W(6076), 1KKA (5259), 1KKA(5256), 2JTP(15417), 1Z2J(6543), 1OW9 (5852), 1PJY(5834), 1NC0(5655), 1LC6(5371), 1R7Z (6077), 2KOC(5705), 2K41(15781), 2GM0(7098), 2K3Z (15780), 2JXS(15572), 2JXQ(15571); in each of 18 systems PDB identifier is followed by BMRB identifier in parenthesis). Prior to the calculation of the structure features, the average structure of the NMR ensemble was calculated and then energy minimized using the AMBER ff99XOL force field. Next, a set of features were selected to describe the local structure around a probe nucleus. Specifically, the local environment around a nucleus was described by feature vectors whose elements consist of the dihedrals of the residue on which a nucleus resides ($\alpha,\beta,\gamma,\delta,\epsilon,\zeta,v0,v1,v2,v3,v4$) and three binary descriptors indicating whether the residue is base-paired, stacked with the preceding residue in the sequence or stacked with the succeeding resides in the sequence. The combined feature vectors, together with measured chemical shifts, the identity of the carbon nucleus and associated residue name, comprised the completed chemical shift-structure relation database.

Generating Chemical Shift Predictor. Taking the complete chemical shift-structure relation database as input, the chemical shift predictors were generated using a machine learning approach. In particular, the random forest approach was used to generate individual C1', C2', C3', C4', C5', C2, C5, C6, C8, H1', H2', H3', H4', H5', H5", H2, H5, H6 and H8 chemical shift predictors. The random forest method was used as included in the random Forest library in the R statistical software package (http://www.r-project.org). Using the default settings in the random Forest package, the random forest approach was used to get a forest of "decision" trees that relate chemical shifts values to the value of the structure features in the database. Each predictor was trained using 1000 randomly constructed decision trees.

Generating Dihedral Angle Predictor. Individual $\alpha,\beta,\gamma,\delta,\epsilon,\zeta,v0,v1,v2,v3$ and $v4$ dihedral angle predictors were generated in a similar fashion. In this case, the forest of "decision" trees relate dihedral values to chemical shifts. A seed structure of the apical loop of the human pre-miR 122 RNA sequence was generated using the following approach. First, the 2-D structure was predicted from the primary structure (5'-GGCUUGUGUCUAAACUAUCAAGCC-3') using the software application MC-FOLD (http://www.major.iric.ca/MC-Fold/). Based on the 2-D structure, hydrogen-bonding constraints were generated for the 5 models with the lowest energy. Second, all dihedral angles were predicted using the chemical shift based dihedral angle predictors described above. The input for the predictors was the experimentally measured chemical shifts. The outputted predicted dihedrals were combined with the hydrogen-bonding constraint to generate 10 preliminary structural models using the software application XPLOR-NIH available at (http://nmr.cit.nih.gov/xplor-nih/). The standard simulated annealing protocol was used to generate the initial structural models. Each of the models was then further refined using restraint MD protocol in the software application NAMD available at: (http://www.ks.uiuc.edu/Research/namd/) In these simulations, MD simulations were carried out using the AMBER ff99XOL force field combined with the GBSA implicit solvent model. Restraints were setup to maintain and enforce the predicted hydrogen bonding and predicted dihedral angles over the course of the simulations. For each, 1ns constant temperature simulation was carried out at 300 K. The results of the structure determination of the human pre-miR 122 RNA sequence are shown in FIG. 7. FIG. 7 illustrates 5 outputted structural models of the human pre-miR 122 apical loop RNA using the methods of the present invention. Shown in FIG. 7 are cartoon representations of the five structural models that best agree with the experimental chemical shift data obtained. Below each, is the $^{13}$C and $^1$H chemical shift RMSD between measured and predicted.

For each restrained MD trajectory, the conformation that best satisfied the restraints were selected and then energy minimized. Using the chemical shift predictors described above, $^{13}C$ and $^{1}H$ chemical shifts were then back-calculated from each model. The RMSD (root-mean-square-deviation) between the measured and predicted chemical shifts were then calculated and top 5 structures were selected.

Example 2

Methods of Using $^{1}H$ NMR Chemical Shifts in Determining RNA Structure and Dynamics Methods and Materials Predicting RNA $^{1}H$ Chemical Shifts. A panel of 18 RNA structures (1ZC5, 2KOC, 1Z2J, 1XHP, 2QH2, 2KYD, 1JU7, 2JTP, 2FDT, 1N8X, 2L3E, 1L1W, 2JYM, 2L5Z, 1NC0, 1IDV, 2L1V, 1OW9) was used to evaluate $^{1}H$ chemical shift predictions using SHIFTS and NUCHEMICS. This panel represents RNA structures that have been determined by NMR following the introduction of SHIFTS and NUCHEMICS (2002-2011) for which $^{1}H$ chemical shift assignments were also available in the Biological Magnetic Resonance Bank (BMRB) (http://www.bmrb.wisc.edu/). Four additional structures (2QH3, 2QH4, 1YMO, 2JWV) were not included due to undocumented or incomplete chemical shift referencing. However, including these structures had little to no impact on the results presented here.

Molecular dynamics (MD) simulations. MD simulations of an RNA duplex (PBID:2KYD), UUCG tetra-loop (PBID: 2KOC), and pre-queosine-1 (preQ1) riboswitch (PDBID: 2LV1) were performed at 300 K and 500 K trajectories using GROMACS 4.5.1 and the AMER94 nucleic acid force field. Structures were subjected to 100 steps of steepest descent minimization and subsequently solvated with TIP3 water in a triclinical box and charge neutralized using sodium counterions. Harmonic constraints with a force constant of 1000 kJ mol-1 nm-2 were placed on the heavy atoms and simulated at 300 K for 1.4 ns. The harmonic constraints were then gradually released over 200 ps. Starting from the equilibrated coordinates two 4 ns trajectories were generated at 300 K and 500 K, respectively. Coordinates were saved every 2 ps.

Replica-exchange molecular dynamics (REMD) simulations were used to generate a broad conformational pool for the human HIV-1 TAR apical loop (shown above in Example 1) from which sets of non-overlapping reference ensembles could be constructed. Initial coordinates were obtained using Rosetta FARNA, a de novo structure determination software program for nucleic acids. Starting from the primary sequence, UAUCGAGCCUGGGAGCUCGAUA, 1000 candidate structures were generated applying base pairing constraints between residues U1 and A22, A2 and U21, U3 and A20, C4 and G19, G5 and C18, A6 and U17, G7 and C16, and C8 and G15. The conformation with the lowest energy was used as the initial coordinates for the REMD simulations. The initial structure was subjected to 100 steps of steepest descent minimization and then solvated with TIP3 water in an octahedron box and charge neutralized using sodium counterions. Harmonic constraints with a force constant of 1000 kJ mol$^{-1}$ nm$^{-2}$ were placed on the heavy atoms and simulated at 300 K for 1.4 ns. The harmonic constraints were then gradually released over 200 ps. Starting from the equilibrated coordinates at 300 K, 15 additional replicas of apical loop were prepared by slowing heating the system to 303, 306, 309, 312, 315, 319, 322, 325, 329, 332, 335, 339, 342, 346 and 350 K. REMD simulations were then initiated from these 16 replicas. Exchanges where attempted every 2 ps and coordinates were saved every 2 ps. Production trajectories 45 ns in length were generated. The 45,000 conformations were used as the representative conformation pool for the TAR apical loop.

Selecting Ensembles. Ensembles were constructed using chemical shifts, residual dipolar coupling (RDC) and chemical shift+RDCs data using the sample and select (SAS) approach. The ensembles were selected by minimizing the cost function, $$\chi^2 = K_{CS}\chi^2_{CS} + K_{RDC}\chi_{RDC}\chi^2_{RDC}$$

where $$\chi^2_{CS} = \frac{1}{L_{CS}}\sum_{i=1}^{N}\left(\delta_i^{pred} - \delta_i^{meas}\right)^2$$

and $$\chi^2_{CS} = \frac{1}{L_{RDC}}\sum_{ij=1}^{N}\left(D_{ij}^{pred} - D_{ij}^{meas}\right)^2$$

Here, $\chi 2$ is the total cost function to be minimized; $\chi 2_{CS}$ and $\chi 2_{RDC}$ are the chemical shift and RDC components of $\chi 2$, respectively; $K_{CS}$ and $K_{RDC}$ are coefficients that determine the contribution of each component to $\chi 2$; $\delta_{pred}$ and $\delta_{meas}$ are the predicted and measured chemical shifts, respectively, and $D_{ij}^{pred}$ and $D_{ij}^{meas}$ are the predicted and measured RDCs, respectively; $L_{CS}$ and $L_{RDC}$ are the total number of chemical shift and RDC data, respectively. For selections using chemical shifts only, $K_{CS}=1$ and $K_{RDC}=0$. For selection using RDCs only, $K_{CS}=0$ and $K_{RDC}=1$. For selections carried out using a combination of chemical shift and RDCs, $K_{CS}$ was varied until $\chi^2_{CS}$ and $\chi^2_{RDC}$ were near specified thresholds while $K_{RDC}=1$. Each selection cycle was initiated from N randomly selected conformers. A Monte Carlo (MC) simulated annealing scheme was then used to minimize Eq. 3. Simulations were initiated at a high-effective temperature, where the MC acceptance probability was high (0.99), and slowly decreased until the MC acceptance probability was 10$^{-5}$. At a given effective temperature 105 MC steps were carried out. The effective temperature was then decreased, with $T_{(i+1)}=0.92\ T_i$.

Generating HIV TAR apical reference ensembles: The ensemble were constructed when setting N=1, 2, 4, 6 and 8. At each N value multiple selection cycles were carried out and then all conformers pooled. For N=2, 4, 6 and 8 ensembles, 80, 40, 26 and 20 selection cycles were carried out so as to ensure that the total number of conformers selected were approximately equal. To generate synthetic 'experimental' datasets, $^{1}H$ chemical shifts were then calculated from the reference ensembles using SHIFTS. To simulate the presence errors in the dataset when carrying out chemical shift based selections, $^{1}H$ chemical shifts were calculated for pool conformers using NUCHEMICS; for the set of 18 benchmark RNAs studied here the mean square-difference (RMSD) between SHIFTS and NUCHEMICS chemical shifts ~0.24 ppm, which is comparable to the uncertainty in NUCHEMICS predictions (~0.30 ppm; see below). Using SHIFTS chemical shifts to generate the reference datasets and then NUCHEMICS chemical shifts to select ensembles therefore effectively simulates the presence ~0.24 ppm error in predictions. This approach to simulate the presence of errors in theoretical simulations is similar to that used by Vendruscolo and coworkers in their study validating the use of chemical shifts to characterize the dynamical ensemble of the protein RNase A.

Comparing Ensembles. To examine how well the generated ensembles reproduce the target reference ensembles, as S-matrix method was employed. In this approach one directly compares the distributions of the two ensembles. Specifically, the matrix was defined as $S=\{s_{ij}\}$, where $$s_{ij}=|\rho_r^{ij}-\rho_t^{ij}|$$

and $\rho_r^{ij}$ and $\rho_r^{ij}$ are the normalized distribution of the inter atomic distance between atoms i and j. $s_{ij}$ ranges between 0 and 2 and is 0 if and only if $\rho_r^{ij}=\rho_t^{ij}$. We constructed S-matrices using the C1' atoms and utilized a bin-size of 0.5 Å to discretize $\rho^{ij}$. Ensemble were compared on the basis of the average $s_{ij}=\langle s_{ij}\rangle_A$.

Accuracy of $^1$H RNA chemical shift predictions. The accuracy was first examined with which RNA $^1$H chemical shifts can be predicted using SHIFTS and NUCEHMICS based on an RNA structure. We note that to our knowledge, SHIFTS $^1$H chemical shift predictions have never been evaluated for RNA. For these benchmark studies, a panel of 18 RNA structures determined by NMR was used for which 1H chemical shift assignments (H1', H2, H5, H6 and H8) are available at the Biological Magnetic Resonance Bank (http://www.bmrb.wisc.edu/). This data set represents RNAs for which $^1$H chemical shifts and NMR structures were deposited in the BMRB and PDB respectively following the introduction of SHIFTS and NUCHEMICS. Thus, they were not used in the developmental of SHIFTS and NUCHEMICS. In all cases, the $^1$H chemical shifts were not used as constraints in RNA structure determination. An additional four data sets were excluded due to undocumented or incomplete chemical shift referencing (note however that including those data sets had little impact on the overall results but generally led to deterioration in the chemical shift predictions). RNAs with modified bases were excluded because they cannot be handled by either SHIFTS or NUCHEMICS.

SHIFTS and NUCHEMICS were used to compute $^1$H chemical shifts based on the NMR structure for our panel of 18 RNA structures. These structures are mainly stem-loop RNAs containing a diverse set of apical loops, ranging from four to twelve bases in size, and internal bulges of varying sequence and type. Most structures contain either single or multiple non-canonical base-pairs, and the set contains one pseudoknot riboswitch structure. The $^1$H chemical shifts were computed for every conformer in the NMR bundle. We then computed the root mean-square-difference (RMSD) between the measured and predicted chemical shifts ($CS^{RMSD}$) for each conformer. The lowest $CS^{RMSD}$ values obtained over the bundle of NMR conformers for each RNA structure were examined. SHIFTS and NUCHEMICS reproduce the observed H1', H2, H5, H6, H8 chemical shifts with an $CS^{RMSD}$ over all 18 structures of 0.32, 0.38, 0.28, 0.31 and 0.37 ppm and 0.29, 0.41, 0.30, 0.27 and 0.31 ppm, respectively and with an overall $CS^{RMSD}$ of 0.35 and 0.34 ppm respectively. These values compare reasonably well with the agreement reported originally for SHIFTS (0.28 ppm) and NUCHEMICS (0.16 ppm). These predictions also compare favorably with $^1$H chemical shift predictions in proteins (typically range between 0.15-0.6 ppm).

In addition to limitations in the $^1$H chemical shift predictions, the agreement between measured and predicted $^1$H chemical shifts could be affected by uncertainties in the NMR structure. While the three structures (PDBID: 2KOC, 2FDT, 1XHP) that yield the best agreement using NUCHEMICS ($CS^{RMSD}=0.19$, 0.19 and 0.21 respec- tively) also have the largest numbers of RDCs constraints per residue (~2.2 as compared to ~0.91 across all structures), a similar trend is not observed for SHIFTS. However, the overall $CS^{RMSD}$ did decrease from 0.35 to 0.32 ppm and from 0.34 to 0.27 ppm for SHIFTS and NUCHEMICS respectively when subjecting the NMR structures to energy minimization prior to chemical shift prediction using the Generalized Born with surface area (GB/SA) implicit solvent model. This improvement is observed across all RNA structures and suggests that some uncertainty in the NMR structure does contribute to the observed $CS^{RMSD}$.

The agreement between measured and predicted 1H chemical shifts is likely also affected by motional averaging, which is not accounted for during the calculation of $^1$H chemical shifts. For example, for pseudoknot preQ RNA, the poor $CS^{RMSD}$ value (0.64 ppm) improves when using the X-ray structure (0.36/0.38 pm when using SHIFTS/NUCHEMICS respectively) or when excluding highly flexible residues (0.32 ppm when residues with a root-mean-square fluctuation (RMSF)>2.0 Å are excluded). However, improved agreement was not observed when averaging the predicted CS data over the entire NMR bundle of structures ($CS_{RMSD}=0.37$ ppm and 0.35 ppm for SHIFTS and NUCHEMICS respectively).

Resolving power of $^1$H chemical shifts.

Next, examination of how well $^1$H chemical shifts can be used to resolve differences between competing RNA conformations was determined. For these studies, experimental $^1$H chemical shifts were used for three RNAs in a panel that contain representative RNA motifs and whose structures were determined with the use of RDCs. These include (i) a 32 nt RNA duplex structure ("duplex") containing a canonical A-form helix determined with a large number of RDC and residual chemical shift anisotropy (RCSA) data; (ii) a 14 nt hairpin containing a UUCG tetraloop ("tetraloop") for which a high resolution NMR structure has recently been reported based on an unprecedented amount of NMR input experimental data: nuclear Overhauser effect (NOE), derived-distances, torsion-angle dependent homonuclear and heteronuclear scalar coupling constants, cross-correlated relaxation rates and RDC; and (iii) a 36 nt preQ$_1$ riboswitch RNA structure determined with the aid of RDCs that contain a pseudoknot motif ("pseudoknot"). These structures fit the $^1$H chemical shifts with variable agreement ($CS^{RMSD}=0.30/0.28$, 0.28/0.21, 0.56/0.58 ppm for duplex, tetraloop, pseudoknot when using SHIFTS/NUCHEMICS respectively). The three RNAs have a similar density of $^1$H experimental chemical shifts (~2.8, 2.6 and 2.8 CS per residue for duplex, 14mer and pseudoknot respectively).

Examination of how well the agreement between the measured and predicted $^1$H chemical shifts for use to distinguish between related RNA conformations. For each of the three RNA structures, a broad distribution of 8000 conformations spanning native and denatured conformations was used by carrying out high temperature MD simulations (see Methods). The resulting pool of conformations superimpose with native structure with an average heavy atom RMSD of 6.0±4.2, 3.5±2.6, and 5.6±3.0 Å for duplex, tetraloop, and psuedoknot, respectively. $^1$H chemical shifts were then calculated for each conformer within each pool using SHIFTS and NUCHEMICS. The $CS^{RMSD}$ value was then computed for each conformer and this compared to the heavy atom root-mean-square deviation between the conformer and the native conformation (structures$_{RMSD}$).

The value of $CS^{RMSD}$ generally decreases with decreasing structure$^{RMSD}$ particularly for structure$^{RMSD}>4$ Å. These data suggest that the CS data can resolve RNA structures to within 4 Å. The continued decrease of $CS^{RMSD}$ for structure$^{RMSD}$<4 Å for UUCG suggests an even stronger structure resolving power. This is likely due to the compact and well known high stability of the UUCG structure, in which fluctuations away from the native structure tend to involve coordinated movements of several bases that can lead to large changes in ring current effects and therefore the predicted chemical shifts. By contrast, motions in duplex and pseudoknot may preserve aspects of stacking interactions and therefore affect the chemical shift data to a lesser extent.

Our analysis suggests that $^1$H chemical shifts can resolve RNA structure to <4 Å resolution. Out of the broad conformational pool that was generated for our three target RNAs, the conformation that best satisfies the measured $^1$H chemical shifts according to SHIFTS/NUCHEMICS (i.e. conformation that yields the lowest $CS^{RMSD}$) superimposes with the native structures with structure$^{RMSD}$ of 2.3/1.9, 1.4/1.4, and 2.9/3.7 Å for duplex, tetraloop and psuedoknot, respectively. Although smaller agreement is observed for pseudoknot, the structureRMSD improves significantly when excluding flexible regions (structure$^{RMSD}$=1.7 and 2.2 Årelative to the X-ray and NMR). Taken together, the presented results strongly suggest that $^1$H chemical shifts can already be implemented as powerful constraints in RNA structure determination.

Use of $^1$H chemical shifts in constructing RNA dynamic ensembles. In solution, chemical shifts are time-averaged over all conformations that are sampled at timescales faster than milliseconds. Studies on protein systems have established the ability to extract this dynamics information from measured chemical shift data Experiments were developed to examine whether $^1$H chemical shifts can facilitate the determination of dynamic ensembles of RNA using the SAS approach, which was previously used to construct ensembles of RNA with the use of RDCs. Here, ensembles with increasing size are constructed in an attempt to find the smallest member ensemble (N) that can satisfies the time-averaged $^1$H chemical shifts. In this approach, N conformers are randomly selected from a pool typically generated using MD simulations, and the agreement between measured and predicted $^1$H chemical shift data is computed. Next, one conformer is randomly replaced with another conformer from the pool, and the agreement with measured $^1$H chemical shift data is re-examined and the newly selected conformer is either accepted or rejected based on the Metropolis criteria. Using such a Monte-Carlo based approach, several iterations are carried out until convergence is reached, defined as achieving agreement between measured and calculated data to within the specified error (see below).

Next, the utility of $^1$H chemical shifts in constructing RNA dynamic ensembles using simulated chemical shift and a known target "reference" ensemble was examined A replica-exchange molecular dynamics (REMD) simulations was used to generate a broad conformation pool for the TAR hexa-nucleotide apical loop construct containing an 8-base-paired stem region. The TAR apical loop has previously been shown to undergo complex motions at multiple timescales and therefore provides a good model system for testing this approach. We then generated 21 reference ensembles that feature different levels of dynamics by randomly selecting a reference conformer from the 45,000 membered pool and then randomly selecting 100 conformers that are within 2, 3 and 4 Å of the reference conformer. In so doing, a total of 21 reference ensembles were generated. The resulting ensembles were skewed to minimize overlap with the selection pool by replicating conformers that under-represented in the reference pool. For each ensemble, 'experimental' ensemble-averaged H1', H2, H5, H6 and H8 chemical shifts were computed using NUCHEMICS. To simulate errors in predicting chemical shifts, the program "SHIFTS" was used to compute the chemical shifts when constructing the ensembles. (See FIG. 3B). This corresponds to ~0.24 ppm prediction error, as judged based on comparison of the average $CS_{RMSD}$ between SHIFTS and NUCHEMICS for the 18 benchmark RNAs studied here. One bond C—H RDCs were also computed assuming a fixed alignment tensor determined experimentally in Pf-1 phage. The RDCs were noise corrupted by adding random white noise with standard deviation of 2.0 Hz corresponding to the uncertainty in RDC measurements in elongated RNA.

In all cases, convergence was achieved for the chemical shift based selections at N=2 ($CS^{RMSD}$=0.13, 0.11 and 0.10 ppm for the 2, 3 and 4 Å reference ensembles; Table 1).

TABLE 1

Back-predicting chemical shifts and RDCs from chemical shift based ensembles.

| | CS: RMSD (ppm)/R | | | RDC: RMSD (Hz)/R | | |
|---|---|---|---|---|---|---|
| N | 2Å | 3Å | 4Å | 2Å | 3Å | 4Å |
| 1 | 0.24/0.97 | 0.25/0.97 | 0.26/0.97 | 25.5/0.77 | 28.1/0.73 | 25.9/0.78 |
| 2 | 0.13/0.99 | 0.11/0.99 | 0.10/0.99 | 15.8/0.89 | 14.1/0.91 | 14.1/0.91 |
| 4 | 0.10/0.99 | 0.09/0.99 | 0.08/0.99 | 15.4/0.89 | 12.6/0.92 | 13.2/0.92 |
| 6 | 0.09/0.99 | 0.08/0.99 | 0.08/0.99 | 14.7/0.90 | 12.2/0.92 | 12.5/0.92 |
| 8 | 0.09/0.99 | 0.08/0.99 | 0.07/0.99 | 14.4/0.90 | 11.3/0.92 | 12.3/0.92 |

Increasing the value of N for chemical shift selections was found to not lead to significant improvements in the chemical shift predictions (Table 1). By comparison, N~8 was required to achieve convergence for RDC and chemical shift+RDC selections; the $RDC^{RMSD}$ for the 2, 3 and 4 Å ensemble was 1.71, 1.72 and 1.72, and 1.73, 1.73 and 1.66 Hz, respectively. Next, experiments were prepared to investigate whether the chemical shift ensembles were able to recapitulate the reference ensembles RDCs. For the N=2 ensemble the $RDC^{RMSD}$=15.8, 14.1, and 14.1 Hz for the 2, 3 and 4 Å ensembles, respectively, and increasing N did not result in any significant improvement in RDC agreement (Table 1). The chemical shift ensembles therefore were unable to satisfy the RDCs to within the 2.0 Hz error thresholds; a similar trend was observed when back-predicting RDCs from ensemble constructed using experimental chemical shift (data not show) In contrast, the RDC ensembles predicted the chemical shifts to within the 0.24 ppm threshold ($CS^{RMSD}$=0.25, 0.24 and 0.23 for the 2, 3 and 4 Å ensembles, respectively).

To further interrogate the chemical shift ensembles, were used to the S-matrix method (Methods) to determine their structural overlap with the reference ensembles. We observed that for N=2 the $<S_{ij}>_A$ was 0.88, 0.78 and 0.84 for the 2, 3 and 4 Å reference ensembles (Table 2). Increasing N did not result in any significant enhancement in the overlap between the chemical shift and reference ensembles (Table 2).

TABLE 2

Overlap between chemical shifts based ensembles and reference ensembles.

| N | 2 Å | 3 Å | 4 Å |
| --- | --- | --- | --- |
| 1 | 1.47 | 1.59 | 1.56 |
| 2 | 0.88 | 0.78 | 0.84 |
| 4 | 0.76 | 0.64 | 0.65 |
| 6 | 0.75 | 0.61 | 0.56 |
| 8a | 0.75/0.44/0.44 | 0.59/0.44/0.41 | 0.53/0.43/0.39 |
| random | 1.06 | 0.93 | 0.78 |

By comparison, the $<S_{ij}>_A$ for randomly ensembles was 1.06, 0.93 and 0.78, indicating there was better correspondence between chemical shift and reference ensembles than the random and reference ensembles. However, the RDC, as well as the, chemical shift+RDC ensembles, exhibited much better overlap with the reference ensembles; for the N=8, $<S_{ij}>_A$ for 2, 3 and 4 Å ensembles was 0.44, 0.44 and 0.43, and 0.44, 0.41 and 0.39, respectively.

Taken together, the chemical shift based ensembles exhibited greater resemblance to the reference ensembles than the randomly constructed ensembles, they were unable to achieve the same degree of overlap as the RDC and chemical shift+RDC, and consequently were unable to adequately predict the reference ensemble RDCs. These effects can be attributed to the comparatively larger error threshold used to define convergence for chemical shift (threshold is ~22% of chemical shift total range) as compared to RDCs (threshold is ~2.5% of the RDC range). Indeed, repeating the simulations with zero error resulted in chemical shift ensembles that exhibited enhanced overlap with the reference ensembles, and thus, better predicted reference ensembles RDC (data not shown). The ability of a chemical shift ensemble to recover the reference ensemble is therefore limited by the accuracy of chemical shifts predictions. Currently, SHIFTS and NUCHEMICS predict $^1$H chemical shifts to within ~0.30 ppm, slightly higher than the 0.24 ppm error threshold used to determine convergence in the theoretical simulations.

Conclusions. NMR structure determination of nucleic acids has traditionally been challenging due to the paucity of inter-proton NOE-derived distance constraints, extended nature of the structure, and high degree of flexibility. There has been a long-standing quest to measure different sources of structural information, and indeed, the measurement of RDCs has revolutionized the ability to determine the structure and dynamics of nucleic acids. There is now renewed interest in utilizing NMR chemical shift to solve RNA structure, as they are the most accessible and accurately measured NMR observable. In this report the inventors have demonstrated that $^1$H chemical shifts can be used to resolve RNA structure, allowing discrimination of native structure from non-native states. The inventors show that using the programs SHIFTS and NUCHEMICS, which on average predict $^1$H chemical shifts to within 0.30 ppm, that $^1$H chemical shifts can be used to resolve with to within ~4 Å resolution. In time, as more accurate 1H chemical shift prediction methods emerge the resolution limit should decrease well below 4 Å. When combined with improvements in RNA structure prediction, it can be anticipated that methodologies such as CS-ROSETTA will evolve that allow high-resolution RNA structure determination based on chemical shift data alone.

Additional studies were performed to investigate whether $^1$H chemical shifts could be used to generate accurate dynamic ensembles of RNAs. Using theoretical simulation on the hexa-nucleotide HIV-1 TAR apical loop our results indicate that though ensembles constructed using $^1$H chemical shifts exhibited greater structural overlap with known reference ensembles than randomly constructed ensembles, they failed to achieve the same degree of overlap as the corresponding RDC ensembles. This result hinted to an inherent degeneracy in the chemical shifts ensembles and in fact, the chemical shift based ensembles were unable to reproduce the RDCs back-calculated from the reference ensembles. Here again, more accurate $^1$H chemical shifts prediction methods should enable more accurate ensembles to be generated, as should the incorporation of chemical shifts from other nuclei e.g. $^{13}$C and $^{15}$N.

Example 3

Predicting RNA $^{13}$C Chemical Shifts using Random Forests

The recent realization of the significant role played by ribonucleic acids (RNA) in orchestrating key cellular processes', as well as the recognition that many of these processes are accompanied by significant structural changes, has brought to the fore the need for efficient methods to determine tertiary structures of RNA, under a variety of experimental conditions. Nuclear magnetic resonance (NMR) spectroscopy has proven to be a value tool in RNA structure determination, Of particular interest to the field is the potential to utilize chemical shifts to aid in structure determination; chemical shifts, as source of structural information, are attractive as they are the most accurately measured NMR observable and are obtained before the typical NMR derived restraints (e.g. NOEs, J-Coupling and RDCs). Typically, acquisition of these NMR derived restraints, which are used in conventional structure determination to solve RNA structure, is both time and labor intensive. The ability to utilize chemical shifts in RNA structure determination will therefore represent a significant step forward that would improve efficiency, thus reducing the turnaround between chemical shift assignment and RNA structure determination Currently, however, chemical shifts are unutilized in RNA structure determination. This is in contrast to proteins, where chemical shifts are now routinely used to help predict, refine and validate structures and have been used to characterize ensemble of proteins including intrinsically disorder proteins. The success of these methods rely on the ability to rapidly and accurately predict protein chemical shifts from coordinates of structural models. In contrast to proteins, however, there is a paucity of methods for predicting RNA chemical shifts from structural models. This lack has significantly hampered the use of chemical shifts in RNA structure determination. This, in spite of accumulation of evidence that, especially in the case of $^{13}$C shifts, point to the existence of certain shift-structure relationships (see below).

The inventors describe what, to the best of their knowledge, is the first attempt to generate empirical models to predict $^{13}$C chemical shifts in RNA (RAMSEY). One approach to generate empirical methods to predict $^{13}$C chemical shifts would be to start from physically motivated mathematical models describing how the magnetic shielding around a carbon nucleus depends on its local environment, and then parameterize these models using a shift-structure database that map measured chemical shifts to calculable structural features. Here an alternate, data centric approach is taken. The assumption begins that with a few, easily calculated structural features, it can be used to adequately describe this structure around a carbon nucleus. No functional relationships between these features and chemical shifts are assumed. Instead, a supervised learning approach is used to reveal any internal structure in a shift-structure database and this data structure is then used to predict chemical shifts. To this end, a shift-structure database was compiled. A key concern when compiling a chemical shift database is whether or not the deposited shifts are consistently referenced. Recently, Aeschbacher et. al. surveyed all the RNA carbon chemical shifts deposited in the Biological Magnetic Resonance Bank (BMRB: www.bmrb.wisc.edu) and found that some entries were improperly referenced or contained inconsistencies. Here the database was populated with measured chemical shift data taken from 20 RNA systems that were identified in that study to have $^{13}C$ chemical shifts deposited in the BMRB that were properly and consistently referenced. In order to calculate the structures features (see below) needed to populate the structure portion of the database, structural models for each of the 20 RNAs where obtained from the PDB. Prior to calculation of the structure features, the first model from the PDB structure file was extracted and then energy minimized using AMBER ff99XoL force field.

Next, a set of features was selected to describe the local structure around a carbon nucleus. RNA $^{13}C$ chemical shifts have been shown to be sensitive to the torsion angles in the parent residue of the carbon nucleus, in particular, the glycosidic torsion angle $\chi 5$, and the exocyclic torsion angle $\gamma$. Additionally, $^{13}C$ shifts appear to be sensitive to ring puckering effects which are explicitly be described by torsion angles v0, v1, v2, v3, and v4 of the ribose sugar. (See FIG. 8). In addition, the local contact strength (Ci) surrounding i. was computed. The contact strength Ci, which describes the steric environment around i, is calculated using:

$$C_i = \sum_j e^{-r_{ij}}$$

where rij is the distance between the carbon i and a heavy atom j that is within 20 Å of i. Finally, it has been demonstrated that 13C shifts can be calculated using bond polarization theory (BPT) model, highlighting the importance of accounting for polarizing effects of the electrostatic cloud surrounding the carbon nucleus. To account for the local electrostatic environment around the carbon nucleus the difference in electrostatic potential ($\Delta Vij=Vi-Vj$) between i, and the atom j with which it shares a bond was calculated. The electrostatic potential centered at atom i is calculated using:

$$V_i = \sum_i \frac{q_k}{r_{ik}}$$

where $q_k$ and $r_{ik}$ are the charge of the atom k within 20 Å of atom i and the corresponding distance between them, respectively. The AMBER ff99 partial charges were used for these calculations. The local structure for every carbon in the database was therefore encoded by a feature vector with elements {$\chi$i, $\gamma$i, vi0, vi1, vi2, vi3, vi4, Ci, Vi1, Vi2, Vi3, Vi4}. These feature vectors, together with measured chemical shifts, the identity of the carbon nucleus and associated residue name, comprised the completed shift-structure database. The final database consisted of 2425 entries. The database was then split into training and validation sets. The training set consisted of 75% of the complete database and the validation set, the remaining 25%.

Using the shift-structure training set, the random forest (RF) method was used to generate empirical models to predict $^{13}C$ chemical shifts. Despite its underlying simplicity, the Random Forest approach has shown the ability to generate highly accurate predictors. To carryout random forest regression the randomForest library in the R-package is used. RF training was independently applied to the C1', C2', C3', C4', C5', C2, C5, C6 and C8 nuclei. As such, separate C1', C2', C3', C4', C5', C2, C5, C6 and C8 predictors (collectively referred to as RAMSEY predictors) were generated. In each Random Forest training session, 500 random trees were grown, and during the tree building process, four of the structure features were randomly chosen to determine the split at each node in the tree. Shown in FIG. 9a are the correlation plots between measured and RAMSEY predicted C1', C2', C3', C4', C5', C2, C5, C6 and C8 shifts in the validation set. The root mean square difference between predicted and measured chemical shifts ($CS_{RMSD}$) was 1.02 ppm and the corresponding $R^2$ was 0.988, indicating excellent agreement between measured and predicted shifts. The $CS_{RMSD}$ value of 1.02 ppm is comparable that obtained for the predictions of $^{13}C$ chemical shifts in proteins. PROSHIFT and SHIFTX2, for example, predict $^{13}C$ chemical shifts with an accuracy ~1.3 ppm and 0.4-1.0 ppm, respectively.

As a demonstration of the utility of the RAMSEY predictors, attempts were made to use the predicted shifts to resolve native RNA structure from a pool consisting of native and decoy models. As a model system, the UUCG tetra-loop containing 14mer stem-loop RNA was used. This 14mer RNA is a good model system since, in addition to the availability of a complete set of chemical shifts, a high-resolution structure has been recently solved (PDBID: 2KOC). It should be noted that the shift-structure data for the 14mer was excluded from the training set used to generate RAMSEY predictors. Decoy models of 14mer RNA, exhibiting 4 2-D structure arrangements (1 native; 3 decoys), were built using the MC-Sym webserver. For each 2-D structure arrangement, the 20 lowest energy models were selected and combined with the 20 models taken from the 2KOC. From each model in the combined pool, the matrix of structure features were generated, the shifts predicted using RAMSEY, and then the $CS_{RMSD}$ computed.

FIG. 9a shows the correlation between $CS_{RMSD}$ between measured and RAMSEY predicted chemical shifts, and the heavy atom structural RMSD (structure$_{RMSD}$) relative to model 1 in 2KOC. The plot reveals a strong and positive correlation between $CS_{RMSD}$ and structure$_{RMSD}$ (Pearson correlation coefficient R~0.73). As a consequence of this correlation, structures with small $CS_{RMSD}$ also exhibit small structure$_{RMSD}$. Encouragingly, the set of structures taken from the high resolution NMR ensemble exhibited the lowest $CS_{RMSD}$ (FIG. 10a; red), while the MC-Sym models generally exhibited higher $CS_{RMSD}$. However, all but one of the decoy structures with $CS_{RMSD}$<1.55 ppm were within 3.0 Å of the native structure, with the structure with the lowest $CS_{RMSD}$ (1.44 ppm) having a structure$_{RMSD}$ of 1.43 Å (FIG. 10b). In contrast, the decoy structure with the largest $CS_{RMSD}$ (2.05 ppm) had a structure$_{RMSD}$ of 3.97 Å (FIG. 10b). In accord with these finding the 2-D structure of the models with the lowest $CS_{RMSD}$ recapitulated the 2-D structure of the native 14mer RNA (FIG. 10b) while the structure with the largest $CS_{RMSD}$ did not. These results clearly demonstrate that the RAMSEY predicted $^{13}C$ chemical shifts capture sufficient structural detail to be able to resolve RNA structure with near atomic accuracy, and more fundamentally suggest that ability to incorporate measured $^{13}C$ shifts within the RNA structure prediction/determination workflow.

The inventors present herein the first empirical models believed to predict $^{13}C$ chemical shifts in RNA. In spite of the small dataset used, and the simplicity of i) the structural features used to describe the local structure surrounding a given carbon nucleus, and ii) the random forest regression approach employed, the models were able predict $^{13}C$ chemical shifts with a $CS_{RMSD}$=1.02 ppm and with an $R^2$=0.988 (FIG. 9a). Encouragingly, predicted $^{13}C$ shifts were used to resolve RNA structure of the benchmark 14mer stem loop RNA to ~1.4 Å of the native structure, explicitly demonstrating for first time the utility of incorporating $^{13}C$ shifts within the RNA structure determination and prediction process.

Example 4

Determination of RNA Structure Using 300 MHz NMR

The inventors performed an experiment acquiring 2-D $^{13}C$—$^1H$ HMQC (heteronuclear multiple quantum correlation) NMR spectra at 300 (dark grey) and 600 (light grey) MHz NMR spectrometers. The samples analyzed using the methods of the present invention consisted of with a 24-mer stem loop construct originated from human pre-miR 122 RNA (5'-GGCUUGUGUCU$_{11}$A$_{12}$AACUAUCAAGCC-3') in which only U11 and A12 residues are $^{13}C/^{15}N$ labeled (0.17 mM RNA in >99% D$_2$O) Utilizing the methods of the present invention, accurate chemical shifts were reliably obtained without spectral overlap even at $^1H$ Larmor frequency of 300 MHz or less by using position specific labeling of nucleotides as described herein. The NMR data were collected at 25° C. For the acquisition of 300 MHz NMR data, a Bruker 300 MHz NMR spectrometer (Department of Chemistry, Penn State University, University Park, Pa.) equipped with a DPX console and a dual probe ($^{13}C$, $^1H$) without z-gradient pulsed field gradient (PFG) was used. For the acquisition of 600 MHz data, an Agilent 600 MHz NMR spectrometer (Nymirum Inc., Ann Arbor Mich.) equipped with a DirectDrive console and a HCN-triple resonance room temperature probe with z-gradient PFG being turned off was used. Spectral widths for the $^1H$ and $^{13}C$ dimensions were 8 and 24 ppm and carrier frequencies for the $^1H$ and $^{13}C$ channels were set at 4.8 (HDO) and 146 ppm, respectively. A total 16 (300 MHz) and 18 (600 MHz) complex data points were acquired for $^{13}C$ dimension. Numbers of scans were 128 and 1024 for 600 and 300 MHz, respectively. Overlaps of the assigned data points are provided in FIG. 11.

The embodiments and the examples described herein are exemplary and not intended to be limiting in describing the full scope of compositions and methods of the present technology. Equivalent changes, modifications and variations of some embodiments, materials, compositions and methods can be made within the scope of the present technology, with substantially similar results.

What is claimed is:

1. A method for determining the 3-D atomic resolution structure of a polynucleotide, the method comprising:
   (a) providing a low-field NMR device having a spectrometer frequency of 300 MHz or less, the NMR device comprising a housing; a sample handling device operable to receive a sample containing the polynucleotide; and a NMR module, wherein the NMR module comprises: a sample conduit comprising an analysis volume operable to receive at least a portion of the sample from the sample handling device; a first tuned coil surrounded by a second tuned coil with the first and the second tuned coil(s) disposed proximately to the analysis volume, wherein each of the first and the second tuned coil(s) being operable to generate a distinct excitation frequency pulse across the analysis volume to generate nuclear magnetic resonance of a plurality of isotopically labeled nuclei of the polynucleotide in the analysis volume; and at least one magnet operable to provide a static magnetic field across the analysis volume and the first and said second tuned coil(s);
   (b) placing an isotopically labeled polynucleotide sample in the sample conduit, wherein the polynucleotide sample comprises a plurality of polynucleotides, having an identical nucleotide sequence, and wherein one or more nucleotides of each polynucleotide is isotopically labeled with one or more atomic labels selected from the group consisting of $^2H$, $^{13}C$, $^{15}N$, $^{19}F$ and $^{31}P$;
   (c) obtaining an NMR spectrum of the polynucleotide sample using a spectrometer frequency of about 20 MHz to about 100 MHz;
   (d) determining a chemical shift of the one or more atomic labels; and
   (e) determining a 3-D atomic resolution structure of the polynucleotide from the chemical shifts determined in step (d) by:
      (i) generating a plurality of theoretical structural polynucleotide 2-D models using the nucleotide sequence and one or more 2-D structure predicting algorithms;
      (ii) generating a plurality of theoretical structural polynucleotide 3-D models using a 3-D structure predicting algorithm using the plurality of theoretical structural polynucleotide 2-D models generated in (i);
      (iii) generating a predicted chemical shift set for each of the plurality of theoretical structural polynucleotides 3-D models generated in (ii);
      (iv) comparing the predicted chemical shift set of each of the plurality of theoretical structural polynucleotide 3-D models to the chemical shift(s) determined in (d); and
      (v) selecting a theoretical structural polynucleotide 3-D model based on the agreement between the respective predicted chemical shift set and the chemical shift(s) determined in (d) as the 3-D atomic resolution structure.

2. The method according to claim 1, wherein at least one of the isotopically labeled nucleotides has a predicted or an experimentally determined structural heterogeneous region.

3. The method according to claim 1, wherein at least one isotopically labeled nucleotide consists of one isotopically labeled purine nucleotide and one isotopically labeled pyrimidine nucleotide.

4. The method according to claim 1, wherein the isotopically labeled polynucleotide sample is prepared by:

(a) determining one or more 2-D or 3-D models of the nucleotide sequence using a 2-D or 3-D structure predicting algorithm, respectively;

(b) identifying one or more structural heterogeneous regions on each of the one or more 2-D or 3-D models of the nucleotide sequence;

(c) calculating one or more chemical shifts from the one or more structural heterogeneous regions; and (d) isotopically labeling one or more nucleotides of the polynucleotide at one or more nuclei, wherein the one or more isotopically labeled nucleotides and one or more nuclei are selected to minimize chemical shift overlap.

5. The method according to claim 1, wherein the predicted chemical shift set generated in (iii) is generated by comparing each theoretical structural polynucleotide 3-D model with a database comprising a relationship between experimental chemical shifts and experimentally determined 3-D polynucleotide structures.

6. The method according to claim 5, wherein generating the predicted chemical shift set comprises:

(f) calculating a polynucleotide structural metric comprising atomic coordinates, stacking interactions, magnetic susceptibility, electromagnetic fields, or dihedral angles from one or more experimentally determined polynucleotide 3-D structures in the NMR-data polynucleotide structure database;

(g) generating a set of mathematical functions or objects that describe relationships between experimental chemical shifts and the polynucleotide structural metric of the experimentally determined 3-D polynucleotide structures using a regression algorithm;

(h) calculating a polynucleotide structural metric for each of the theoretical structural polynucleotide 3-D models; and (i) inputting the polynucleotide structural metric for each of the theoretical structural polynucleotide 3-D models into the set of mathematical functions or objects from (g) to generate the predicted chemical shift set.

7. The method according to claim 6, wherein the regression algorithm is a Random Forest algorithm.

8. The method according to claim 5, wherein determining the chemical shift of the one or more atomic labels comprises modeling the chemical shift set using an NMR spectrometer frequency of 300 MHz or less.

9. A method for determining the 3-D atomic resolution structure and dynamics of a biomolecule, the method comprising:

(a) providing a low-field NMR device having a spectrometer frequency of 300 MHz or less, the NMR device comprising a housing; a sample handling device operable to receive a sample containing the biomolecule; and a NMR module, wherein the NMR module comprises: a sample conduit comprising an analysis volume operable to receive at least a portion of the sample from the sample handling device; a first tuned coil surrounded by a second tuned coil with the first and the second tuned coil(s) disposed proximately to the analysis volume, wherein each of the first and the second tuned coil(s) being operable to generate a distinct excitation frequency pulse across the analysis volume to generate nuclear magnetic resonance of a plurality of isotopically labeled nuclei of the biomolecule in the analysis volume; and at least one magnet operable to provide a static magnetic field across the analysis volume and the first and said second tuned coil(s);

(b) placing an isotopically labeled biomolecule sample in the sample conduit, wherein the biomolecule sample comprises a plurality of biomolecules having an identical biomolecule sequence, and wherein each biomolecule is isotopically labeled with one or more atomic labels selected from the group consisting of $^2$H, $^{13}$C, $^{15}$N, $^{19}$F and $^{31}$P;

(c) obtaining an NMR spectra of the biomolecule using a spectrometer frequency of about 20 MHz to about 100 MHz;

(d) determining a chemical shift of the one or more atomic labels; and (e) determining a 2-D or a 3-D atomic resolution structure of the biomolecule from the chemical shifts determined in step (d) by:

(i) generating a plurality of theoretical structural biomolecule 2-D models using the biomolecule sequence and one or more 2-D structure predicting algorithms;

(ii) generating a plurality of theoretical structural biomolecule 3-D models using a 3-D structure predicting algorithm using the plurality of theoretical structural biomolecule 2-D models generated in (i);

(iii) generating a predicted chemical shift set for each of the plurality of theoretical structural biomolecule 3-D models generated in (ii);

(iv) comparing the predicted chemical shift set of each of the plurality of theoretical structural biomolecule 3-D models to the chemical shift(s) determined in (d); and (v) selecting a theoretical structural biomolecule 3-D model based on the agreement between the respective predicted chemical shift set and the chemical shift(s) determined in (d) as the 3-D atomic resolution structure.

10. The method according to claim 9, wherein placing a biomolecule sample in the sample conduit further comprises heating or cooling the biomolecule in the sample conduit prior to or during obtaining an NMR spectra of the biomolecule.

11. The method according to claim 9, wherein obtaining an NMR spectra of the biomolecule further comprises applying a pulsed field gradient during acquisition of experimental chemical shift data of the plurality of nuclei of the biomolecule.

12. The method according to claim 9, wherein the biomolecule is an isotopically labeled polynucleotide.

13. The method according to claim 12, wherein the isotopically labeled polynucleotide is an isotopically labeled ribonucleic acid (RNA).

14. The method according to claim 12, wherein the predicted chemical shift set generated in (iii) is generated by comparing each theoretical structural polynucleotide 3-D model with a database comprising a relationship between experimental chemical shifts and experimentally determined 3-D polynucleotide structures.

15. The method according to claim 14, wherein generating the predicted chemical shift set comprises:

(f) calculating a polynucleotide structural metric comprising atomic coordinates, stacking interactions, magnetic susceptibility, electromagnetic fields, or dihedral angles from one or more experimentally determined polynucleotide 3-D structures in the database;

(g) using a regression algorithm to generate a set of mathematical functions or objects that describe relationships between experimental chemical shifts and the polynucleotide structural metric of the experimentally determined 3-D polynucleotide structures;
(h) calculating a polynucleotide structural metric for each of the theoretical structural polynucleotide 3-D models; and
(i) inputting the polynucleotide structural metric for each of the theoretical structural polynucleotide 3-D models into the set of mathematical functions or objects to generate the predicted chemical shift set.

16. The method according to claim 15, wherein the regression algorithm is a Random Forest algorithm.

* * * * *